United States Patent
Sun et al.

(10) Patent No.: US 11,033,658 B2
(45) Date of Patent: *Jun. 15, 2021

(54) INTERPENETRATING NETWORKS WITH COVALENT AND IONIC CROSSLINKS

(71) Applicants: President and Fellows of Harvard College, Cambridge, MA (US); Seoul National University Industry Foundation, Seoul (KR)

(72) Inventors: Jeong-Yun Sun, Cambridge, MA (US); Xuanhe Zhao, Durham, NC (US); Widusha R. K. Illeperuma, Cambridge, MA (US); Kyu H. Oh, Seocho-gu (KR); Joost J. Vlassak, Lexington, MA (US); Zhigang Suo, Lexington, MA (US); Jianyu Li, Cambridge, MA (US); David J. Mooney, Sudbury, MA (US)

(73) Assignees: President and Fellows of Harvard College, Cambridge, MA (US); Seoul National University Industry Foundation

( * ) Notice: Subject to any disclaimer, the term of this patent is extended or adjusted under 35 U.S.C. 154(b) by 0 days.

This patent is subject to a terminal disclaimer.

(21) Appl. No.: 16/459,907

(22) Filed: Jul. 2, 2019

(65) Prior Publication Data
US 2020/0000967 A1  Jan. 2, 2020

Related U.S. Application Data

(63) Continuation of application No. 15/172,549, filed on Jun. 3, 2016, now Pat. No. 10,383,980, which is a continuation of application No. 14/370,451, filed as application No. PCT/US2013/020518 on Jan. 7, 2013, now Pat. No. 9,387,276.

(60) Provisional application No. 61/694,039, filed on Aug. 28, 2012, provisional application No. 61/583,586, filed on Jan. 5, 2012.

(51) Int. Cl.
| | |
|---|---|
| *A61L 27/16* | (2006.01) |
| *A61L 27/20* | (2006.01) |
| *A61L 27/48* | (2006.01) |
| *A61L 27/50* | (2006.01) |
| *A61L 27/52* | (2006.01) |
| *A61L 27/60* | (2006.01) |
| *A61L 27/26* | (2006.01) |
| *C08J 3/075* | (2006.01) |
| *C08J 3/24* | (2006.01) |
| *C08L 5/04* | (2006.01) |
| *C08L 33/26* | (2006.01) |
| *C08L 71/02* | (2006.01) |

(52) U.S. Cl.
CPC .............. *A61L 27/52* (2013.01); *A61L 27/16* (2013.01); *A61L 27/20* (2013.01); *A61L 27/26* (2013.01); *A61L 27/48* (2013.01); *A61L 27/50* (2013.01); *A61L 27/60* (2013.01); *C08J 3/075* (2013.01); *C08J 3/246* (2013.01); *C08L 5/04* (2013.01); *C08L 33/26* (2013.01); *C08L 71/02* (2013.01); *C08J 2333/26* (2013.01); *C08J 2405/04* (2013.01); *C08L 2201/54* (2013.01); *C08L 2203/02* (2013.01); *C08L 2205/04* (2013.01)

(58) Field of Classification Search
None
See application file for complete search history.

(56) References Cited

U.S. PATENT DOCUMENTS

| | | | |
|---|---|---|---|
| 3,611,732 A | 10/1971 | Epstein | |
| 5,334,640 A | 8/1994 | Desai et al. | |
| 5,644,049 A | 7/1997 | Giusti et al. | |
| 6,030,634 A | 2/2000 | Wu et al. | |
| 6,271,278 B1 | 8/2001 | Park et al. | |
| 6,960,617 B2 * | 11/2005 | Omidian | A61K 9/0065 521/102 |
| 8,293,510 B2 * | 10/2012 | Detamore | A61L 27/38 435/178 |
| 9,987,221 B2 * | 6/2018 | Richard | A61K 9/10 |
| 2003/0232895 A1 | 12/2003 | Omidian et al. | |
| 2008/0317818 A1 | 12/2008 | Griffith et al. | |
| 2010/0055184 A1 * | 3/2010 | Zeitels | A61L 27/26 424/484 |

FOREIGN PATENT DOCUMENTS

| | | |
|---|---|---|
| FR | 2938544 A1 | 5/2010 |
| WO | 1998/52543 A1 | 11/1998 |
| WO | 2010/093528 A2 | 8/2010 |

OTHER PUBLICATIONS

U.S. Appl. No. 14/370,451, filed Jul. 2, 2014, now U.S. Pat. No. 9,387,276.
U.S. Appl. No. 15/172,549, filed Jun. 3, 2016, now U.S. Pat. No. 10,383,980.
Haug et al., The Effect of Divalent Metals on the Properties of Alginate Solutions. II. Comparison of Different Metal Ions. Acta Chemica Scandinavica. 1965;19;341-51.
Leo et al., Effects of sterilization treatments on some properties of alginate solutions and gels. Biotechnol Prog. Jan-Feb. 1990;6(1):51-3.
Omidian et al., Elastic, superporous hydrogel hybrids of polyacrylamide and sodium alginate. Macromol Biosci. Sep. 15, 2006;6(9):703-10.
Tsujino et al., A new unsaturated uronide isolated from alginase hydrolysate. Nature. Dec. 9, 1961;192:970-1.

\* cited by examiner

*Primary Examiner* — Tae H Yoon
(74) *Attorney, Agent, or Firm* — McCarter & English, LLP; Maria Laccotripe Zacharakis; Wei Song

(57) ABSTRACT

The invention features a composition comprising a self-healing interpenetrating network hydrogel comprising a first network and a second network. The first network comprises covalent crosslinks and the second network comprises ionic or physical crosslinks. For example, the first network comprises a polyacrylamide polymer and second network comprises an alginate polymer.

12 Claims, 52 Drawing Sheets

FIG. 9A
Alginate
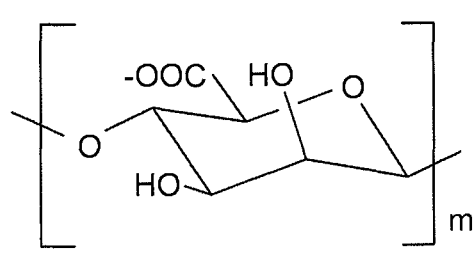
PAAm
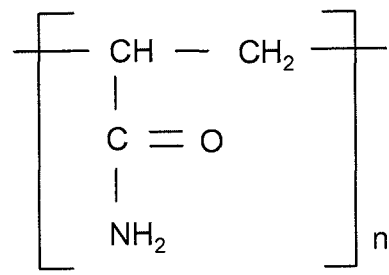
PAAm/Alginate
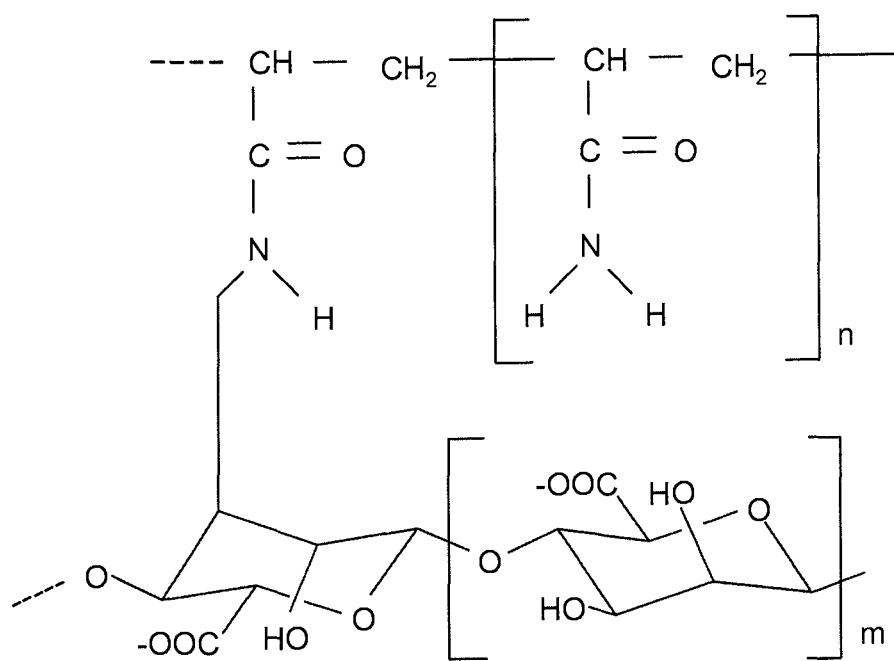

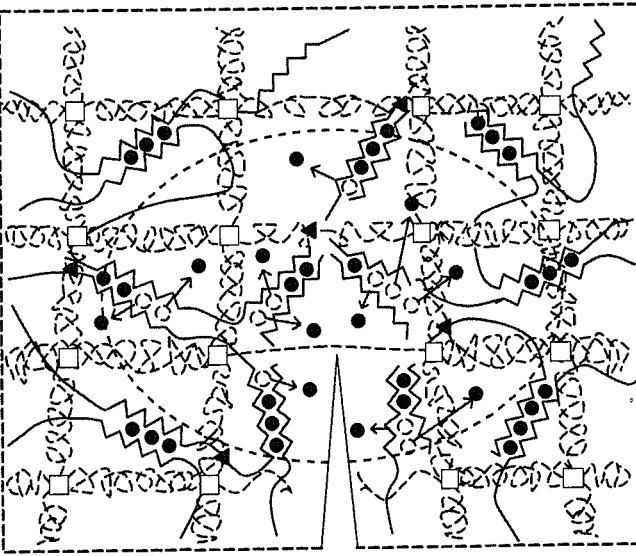
FIG. 21C  Hybrid gel
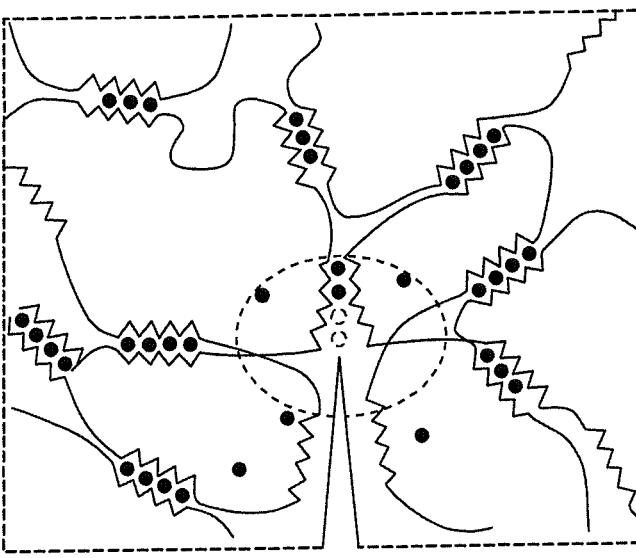
FIG. 21B  Alginate gel
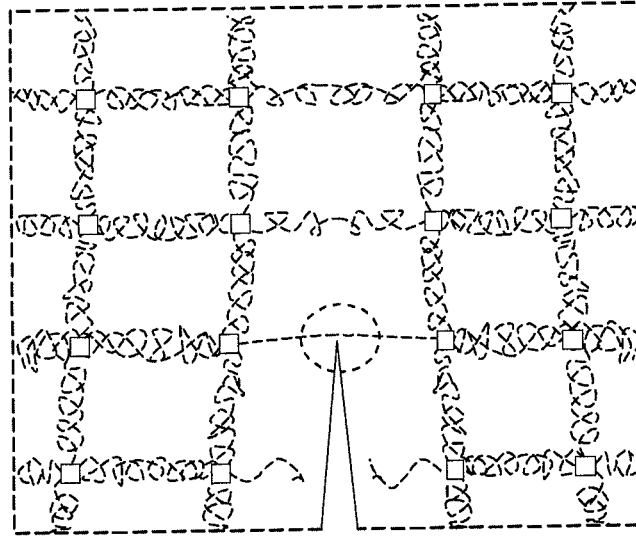
FIG. 21A  Polyacrylamide gel
- - - Plastic zone near the crack tip

MBAA

*Initial elastic modulus measured*

| 20C | 35C | 42C | 50C |
|-----|-----|-----|-----|
| 46  | 73  | 59  | 28  |

INTERPENETRATING NETWORKS WITH COVALENT AND IONIC CROSSLINKS

RELATED APPLICATIONS

This application is a continuation of U.S. patent application Ser. No. 15/172,549, filed Jun. 3, 2016 and now U.S. Pat. No. 10,383,980; which is a continuation of U.S. patent application Ser. No. 14/370,451, filed Jul. 2, 2014 and now U.S. Pat. No. 9,387,276; which, in turn, is a national stage application of International Patent Application No. PCT/US2013/020518, filed Jan. 7, 2013; which claims the benefit of priority to U.S. Provisional Patent Application No. 61/583,586, filed Jan. 5, 2012, and to U.S. Provisional Patent Application No. 61/694,039, filed Aug. 28, 2012. Each of the aforementioned applications is incorporated herein by reference in its entirety.

FIELD OF THE INVENTION

The invention relates to hydrogels.

BACKGROUND OF THE INVENTION

Hydrogels have applications in many areas including tissue engineering, diapers, contact lenses, media for electrophoresis etc. However, the soft, weak, and brittle behaviors of hydrogels have limited the applications where mechanical properties are important.

SUMMARY OF THE INVENTION

The compositions and methods of the invention provide a solution to many of the drawbacks of earlier hydrogels. Due to improved mechanical and chemical properties, the hydrogels are useful in applications for which existing hydrogels have failed. Performance in existing applications is improved with the hydrogels described herein. For example, the improved hydrogels described herein are useful in applications where existing hydrogels lacked sufficient mechanical strength, e.g., in the replacement of biological tissue such as joint cartilage, spine discs, ligaments, tendons, blood vessels, heart valves, muscle, and skin. The improved hydrogels described herein are also useful in soft robotics, multilayer systems, and impact protectors.

The invention features a composition comprising a self-healing interpenetrating networks (IPN) hydrogel comprising a first network and a second network. The first network comprises covalent crosslinks and the second network comprises a non-covalent, e.g., ionic or physical, crosslinks. In a preferred embodiment, the first network and the second network are covalently coupled. The nature of the bonds between first and second networks is determined using Fourier Transform Infrared (FTIR) spectra or Thermogravimetric analysis (TGA). The interpenetrating network hydrogel comprises enhanced mechanical properties selected from the group consisting of self-healing ability, increased fracture toughness, increased ultimate tensile strength, and increased rupture stretch. The IPN hydrogel is made by mixing covalently crosslinked first network and ionically crosslinked second network.

The covalently crosslinked first network and ionically crosslinked second network are mixed at the molecular level. This mixing leads to enhanced mechanical properties of the IPN hydrogels. For example, the fracture toughness was enhanced by following mechanism. The covalently crosslinked network bridge the crack and stabilize deformation in the background, the chemical interactions between two networks transfer the load over a large zone, and the ionic bonds between ionically crosslinked network break and provide inelastic deformation over this large zone around the root of the notch.

The interpenetrating polymer network comprises between about 30% and 90% water, e.g., about 35%, about 45%, about 50%, about 55%, about 60%, about 65%, about 70%, about 75%, about 80%, or about 85% water. However, despite the high water content of the gel, it is characterized by superior toughness, e.g., at least an order of magnitude tougher than earlier gels.

For example, the first network comprises a polyacrylamide polymer and second network comprises an alginate polymer. Covalently cross-linked network components include polyacrylamide, poly(vinyl alcohol), poly(ethylene oxide) and its copolymers, polyethylene glycol (PEG), and polyphosphazene. Also, any polymer that is methacrylated (e.g., methacrylated PEG) could be used in a similar manner. Ionically or physically cross-linked network components include alginate, chitosan, agarose, self-assembling polypeptides, peptide amphiphiles (all form reversible cross-links due to ionic, hydrophobic or other secondary interactions). A preferred component of the ionically crosslinked network includes alginate, which is comprised of (1-4)-linked b-D-mannuronic acid (M) and a-L-guluronic acid (G) monomers that vary in amount and sequential distribution along the polymer chain. Alginate is also considered a block copolymer, composed of sequential M units (M blocks), regions of sequential G units (G blocks), and regions of alternating M and G units (M-G blocks) that provide the molecule with its unique properties. Alginates have the ability to bind divalent cations such as $Ca^{+2}$ between the G blocks of adjacent alginate chains, creating ionic interchain bridges between flexible regions of M blocks. Other examples include polymers that contain alginic acid, pectinic acid, carboxymethyl cellulose, hyaluronic acid, or chitosan. Covalent crosslinking agents include N,N-methylenebisacrylamide (MBAA), methacrylate, carbodiimide crosslinkers [e.g., N, N'-Dicyclohexylcarbodiimide (DCC), 1-Ethyl-3-(3-dimethylaminopropyl) carbodiimide (ECC)], N-hydroxysuccinimide and N-hydroxysulfosuccinimide, glutaraldehyde, and transglutaminases. Crosslinking agents that promote ionic crosslinks include $CaCl_2$, $CaSO_4$, $CaCO_3$, hyaluronic acid, and polylysine.

Unlike earlier double network (DN) hydrogels, neither network of the IPN hydrogels described herein is sacrificed upon the application of energy to the network.

The interpenetrating polymer network comprises a fracture toughness that is about 900 times higher compared to a hydrogel consisting of alginate alone. For example, the fracture toughness is about 800, about 850, about 900, about 950, or about 1,000 times higher compared to a hydrogel consisting essentially of alginate polymer alone. Alternatively, the interpenetrating polymer network comprises a fracture toughness that is about 90 times higher compared to a hydrogel consisting essentially of acrylamide polymer alone, e.g., about 80, about 85, about 95 or about 100 times higher compared to a hydrogel consisting of acrylamide alone.

For example, the interpenetrating polymer network comprises a fracture toughness value of between 10 $J/m^2$ and 9000 $J/m^2$. The interpenetrating polymer network comprises a fracture toughness value of at least 1000 $J/m^2$, e.g., at least 1500 $J/m^2$, at least 2000 $J/m^2$, at least 3000 $J/m^2$, or at least 4000 $J/m^2$. In preferred embodiments, the interpenetrating polymer network comprises a fracture toughness value of at least 5000 J/m², at least 6000 J/m², at least 7000 J/m², at least 8000 J/m², or at least 9000 J/m². In one aspect, the fracture toughness of the network hydrogel is enhanced as follows: the covalently-crosslinked network bridges the crack and stabilizes deformation in the background, while the chemical interactions between the two networks transfer the load over a large zone, and the ionic bonds between ionically crosslinked networks break and provide inelastic deformation over this large zone around the root of a notch, i.e., a defect such as a crack, tear, or a knife-cut notch.

In order to increase the fracture toughness of the interpenetrating polymer network, the hydrogel is cured at a temperature of between 20° C. and 100° C., e.g., between 40° C. and 90° C., between 60° C. and 80° C., or about 70° C. For example, the hydrogel is cured at a temperature of between 20° C. and 36° C., e.g., 21° C., 22° C., 23° C., 24° C., 25° C., 26° C., 27° C., 28° C., 29° C., 30° C., 31° C., 32° C., 33° C., 34° C., or 35° C. In other examples, the curing is carried out at about 50° C. This thermal treatment is performed before free radical polymerization. The mixture of alginate and acrylamide is cured at a selected temperature for at least 10 min., 20 min., 30 min., 45 min., 60 min, 90 min., 120 min. Typically, the curing or thermal treatment is done for one hour. This optional step facilitates the formation of covalent bonds between the covalently linked acrylamide network and the ionically linked alginate network.

The interpenetrating polymer network comprises an ultimate tensile strength that is about 43.3 times higher compared to a hydrogel consisting of alginate alone, e.g., about 30, about 35, about 40, about 45, or about 50 times higher compared to a hydrogel consisting of alginate alone. Alternatively, the interpenetrating polymer network comprises an ultimate tensile strength that is about 13.8 times higher compared to a hydrogel consisting of acrylamide alone, e.g., about 5, about 10, about 15, or about 20 times higher compared to a hydrogel consisting of acrylamide alone.

The interpenetrating network hydrogel also comprises a high stretch value, e.g., about 21. Thus, the hydrogels are extremely stretchable and tough compared to conventional hydrogels.

In some cases, the interpenetrating polymer network is un-notched, and the network hydrogel comprises a rupture stretch that is about 19.2 times higher compared to a hydrogel consisting of alginate alone, e.g., about 10, about 15, about 20, about 25, or about 30 times higher compared to a hydrogel consisting of alginate alone. Alternatively, the interpenetrating polymer network is un-notched, and the network hydrogel comprises a rupture stretch that is about 3.4 times higher compared to a hydrogel consisting of acrylamide alone, e.g., about 2, about 3, about 4, or about 5 times higher compared to a hydrogel consisting of acrylamide alone. For example, the interpenetrating polymer network hydrogel is un-notched, and the network hydrogel comprises a rupture stretch of about 2 to about 25. In some cases, the interpenetrating polymer network hydrogel is notched, and the network hydrogel comprises a critical crack propagation stretch of about 2 to about 17. Stretch value ($\lambda$) is determined by providing the measured length (under stress, e.g., stretched) divided by the undeformed gauge length.

The polymer ratio between said polyacrylamide polymer and said alginate polymer is between about 66.67 wt. % and 94.12 wt. %, e.g., about 88.89 wt. % or about 85.71 wt. %. In some cases, the ratio between $CaSO_4$ and alginate is between about 3.32 wt. % and 53.15 wt. %, e.g., about 13.28 wt. %. The interpenetrating polymer network comprises a N,N-methylenebisacrylamide(MBAA)/acrylamide weight ratio of between about 0.031 wt. % and 0.124 wt. %.

The interpenetrating polymer network hydrogel comprises a Young's modulus of about 10.0 kPa to about 300 kPa, e.g., about 25, about 50, about 75, about 100, about 125, about 150, about 175, about 200, about 225, about 250, about 275 or about 300 kPa and up to the megaPa range. For example, the interpenetrating network hydrogel comprises an elastic modulus of about 10.0 kPa with a 2.7 kPa standard deviation. In another example, the IPN hydrogel is characterized by a Young's modulus of about 5 megaPa, making it therefore suitable for cartilage repair and replacement.

In contrast to earlier DN hydrogels, the present network comprises the property of self-healing. Earlier double network (DN) gels included a strong network that required a high level of stress to break and a loose, stretchy network. Upon application of stress, the strong network eventually breaks and is sacrificed, i.e., once it is broken, it cannot be restored. The present interpenetrating network hydrogels are self-healing, because neither polymer network (ionically crosslinked network or covalently crosslinked network) is sacrificed. Thus, the hydrogel is self-healing, i.e., it is characterized by a mechanical cycling restoration property, wherein about 30% to 80% energy density of a first loading is recovered after a time period of rest, e.g., about 35%, about 40%, about 45%, about 50%, about 55%, about 60%, about 65%, about 70%, about 75%, or about 80% energy density of a first loading is recovered after a time period of rest.

The time period of rest comprises a time period greater than 1 millisecond. For example, the rest period comprises a period of greater than about 10 seconds and less than 1 day, e.g., about 1 minute, about 10 minutes, about 30 minutes, about 1 hour, about 2 hours, about 4 hours, about 8 hours, about 12 hours, or about 16 hours, or about 24 hours. For example, a time period of rest comprises storage at a temperature greater than 20° C. and less than 80° C., e.g., a storage temperature of about 80° C. In this manner, the mechanical strength and flexibility properties can be restored an indefinite number of times (e.g., 2, 3, 10, 25, 50, or 100 times or more) by alternating periods of stress application with rest periods. The interpenetrating polymer networks hydrogel also fully recovers its original length after unloading.

The interpenetrating polymer network comprises a constant ratio of 0.1 between loss modulus and storage modulus at a frequency of 0.01 Hz to 20 Hz In some examples, the interpenetrating polymer network is homogenous throughout the entire hydrogel, e.g., at a micron level and at a millimeter level. In other examples, the polymers and or crosslink density if variable throughout the hydrogel, e.g., forming a gradient of polymer concentration or crosslink density.

Finally, the interpenetrating network described herein is defect resistant, i.e., the durable gel is not prone to development of tears. The improved hydrogels of the invention are resistant to defects, and even if a defect occurs, the gel maintains its toughness and does not fail. Preferably, the crosslinking density of the polyacrylamide polymer is between about 0.031 and 0.124 wt.-%, e.g., about 0.062 wt.-%.

An advantage of the interpenetrating network hydrogels described herein is that they are not cytotoxic to cells over long periods of time, e.g., 3 days, 7 days, 14 days, 28 days 56 days, 112 days, or 224 days.

The biocompatible gels described herein offer significant advantages, particularly in medical applications. For example, drug delivery hydrogels or cell delivery hydrogels that are used for muscle generation or regeneration are subject to application of energy/stresses. Since the hydrogels described herein are more mechanically robust, more durable, and are characterized by a higher fracture resistance, they are more suitable for such applications involving muscle tissue. Other applications are also improved with the use of the tough hydrogels. For example, materials used in surgical procedures (e.g., wraps, meshes), cartilage replacement, joint replacement, orthopedic/orthochondral defect repair (e.g., bone or cartilage fillers), spinal procedures (e.g., nuclear propulsus spinal surgery), ophthamological uses (e.g., optically-clear, flexible, durable lenses, contact lens or implantable lens), as well as non-medical uses (e.g., fillers in cosmetic surgical procedures).

In addition to clinical uses such as tissue repair and replacement, the IPN hydrogels are also useful in non-medical settings, e.g., in fabrication of soft robotics that swim, crawl, fly, or squeeze through small spaces without breaking. The IPN hydrogels are also useful to make actuators. Other examples include artificial muscles, tunable lenses, actuators and skins for soft robotics, encapsulate protecting layers, stretchable membranes for dielectric actuator, loud speaker membranes, multilayer systems, fiber reinforced tough hydrogel, particle reinforced tough gel as well as durable filtration systems.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIG. 1A is a photograph showing a strip of the hydrogel between two grips. FIG. 1B is a photograph showing the hydrogel stretched 21 times its initial length. FIG. 1C is a photograph showing a 2 cm long crack introduced into the hydrogel in the undeformed state. FIG. 1D is a photograph showing that the crack does not advance when the hydrogel is stretched 17 times its initial length. The ratio of the weights of AAm and alginate is 8:1, and water content is 86 wt. %.

FIG. 3A is a schematic showing the tearing method to measure the fracture toughness. The fracture tests were generally performed with 75 mm wide (L), 5 mm long ($h_0$), 3 mm thick (t) samples. The crack was initiated by a single 40 mm-long knife-cut notch. The stretch rate ($\lambda°$) was kept constant as 2/min. FIG. 3B is a line graph showing the stress-strain curves for uniaxial tensile test (red) and fracture test (blue). The fracture sample has $c_0/L=0.47$ initial notch. The circle in the fracture graph represents onset crack propagation stretch ($\lambda_c$). The energy density per unit volume (W) was calculated by integrating the under area of the tensile graph upto the critical stretch ($\lambda_c$). FIG. 3C is a line graph showing the effects of the weight ratio of AAm network to the whole polymer network on stress-strain curves in tensile test. Numbers on the curves in C denote the value of weight % of AAm monomer to the whole polymer in gel. FIG. 3D is a line graph showing the effects of the weight ratio of AAm network to the whole polymer network on and toughness. The value at zero and 100 wt. % are for the alginate and PAAm SN gels, respectively. Samples: PAAm-$x_1$-0.06/Alginate-$x_2$-13.28 IPN gels with a constant water content 86 wt.-%.

FIG. 4A shows a schematic scenario for the formation of tough gel. The PAAm network has a long enough chain to be stretched to the critical stretch of IPN gel, but the PAAm network is brittle because it has significant stress concentration near the initial flaws and small plastic zone (dark yellow area) size. When the ionically crosslinked alginate networks are added to the PAAm back bone networks, the alginate network will help to dissipate the energy as a plastic deformation without breaking the alginate chain itself. As a result, the plastic behavior of ionically cross-linked alginate assist to broaden the plastic zone size and delay the fracture of the PAAm/alginate IPN gel. FIG. 4B is a line graph showing stress-strain curves for PAAm/Alginate IPN gels with calcium ions (red) and without calcium ions (blue) under uniaxial tension, curves are plotted with PAAm SN gel (dark yellow). Calcium ions, the crosslinker for alginate network, improved the stretchability and stiffness of PAAm/Alginate IPN gel. Red: PAAm-13.55-0.06/Alginate-2.26-13.28 IPN gel (water content: 86 wt.-%); blue: PAAm-13.55-0.06/Alginate-2.26-0 IPN gel (water content: 86 wt.-%); dark yellow: PAAm-13.55-0.06 SN gel (water content: 88 wt.-%). FIG. 4C is a line graph showing the loading-unloading curves for PAAm, Alginate SN gels and PAAm/Alginate IPN gel under uniaxial tension. Hysteresis is the dependence of a system not only on its current environment but also on its past environment. Covalently crosslinked PAAm gel shows no hysteresis. Ionically crosslinked alginate gel has huge hysteresis and remains plastic deformation after unloading. PAAm/Alginate IPN gel also shows hysteresis and plastic deformation like alginate gel which can dissipate the energy during the loading. Maximum stretch and stretching rate were fixed as $\lambda=1.2$ and $\lambda°=2$/min, respectively. Blue: PAAm-14.05-0.06 SN gel (water content: 88 wt.-%); dark yellow: Alginate-1.76-13.28 SN gel (water content: 97 wt.-%); red: PAAm-14.05-0.06/Alginate-1.76-13.28 IPN gel (water content: 86 wt.-%).

In FIGS. 5A-C, samples were first loaded to $\lambda=7$ (black), and unloaded to the initial length (black) with a stretch rate $\lambda°=2$/min. The samples are stored in isothermal hot bathes with the temperatures of (A) 20° C., (B) 60° C. and (C) 80° C. The second loadings are followed after keeping the samples in the hot bath for 10 secs (olive), 10 mins (violet), 1 hour (dark yellow), 4 hours (blue) and 1 day (red). FIG. 5D is a dot plot showing the energy density of $2^{nd}$ loading is plotted as a function of self-healing time with various healing temperature 20° C. (square), 60° C. (triangle) and 80° C. (inverted triangle). The energy density of $1^{st}$ unloading is plotted as a dashed line also. Samples: PAAm-13.55-0.06/Alginate-2.26-13.28 IPN gel (water content: 86 wt.-%).

FIG. 6A is a line graph showing the effects of the weight ratio of MBAAm on stress-strain curves in a tensile test. Numbers on the curves in (A) denote the value of $y_1$, the crosslinker (MBAAm) concentration in wt.-% with respect to the PAAm network. FIG. 6B is a line graph showing the effects of the weight ratio of MBAAm on critical stretch in fracture test. FIG. 6C is a line graph showing the effects of the weight ratio of MBAAm on toughness. Samples: PAAm-14.37-$y_1$/Alginate-1.44-26.57 IPN gels with a constant water content 86 wt.-%.

FIG. 7A is a line graph showing the effects of the weight ratio of $CaSO_4$ on stress-strain curves in a tensile test. Numbers on the curves in (A) denote the value of $y_2$, the crosslinker ($CaSO_4$) concentration in wt.-% with respect to the alginate network. FIG. 7B is a line graph showing the effects of the weight ratio of $CaSO_4$ on critical stretch in fracture test. FIG. 7C is a line graph showing the effects of the weight ratio of $CaSO_4$ on toughness. Samples: PAAm-14.37-0.06/Alginate-1.44-$y_2$ IPN gels with a constant water content 86 wt.-%.

FIG. 8A is a line graph showing the effects of the weight ratio of AAm network to the whole polymer network on stress-strain curves in a tensile test. Numbers on the curves in (A) denote the value of weight % of AAm monomer to the whole polymer in gel. FIG. 8B is a line graph showing the effects of the weight ratio of AAm network to the whole polymer network on critical stretch in fracture tests. FIG. 8C is a line graph showing the effects of the weight ratio of AAm network to the whole polymer network on toughness. The value at zero and 100 wt. % are for the alginate and PAAm SN gels, respectively. Samples: PAAm-$x_1$-0.06/Alginate-$x_2$-13.28 IPN gels with a constant water content 86 wt.-%.

FIGS. 9A-B are a series of chemical structures and a graph. FIG. 9A is a series of chemical structures of Alginate and PAAm, and the suggested structure of PAAm/Alginate copolymer. FIG. 9B is a graph showing the FTIR spectra of PAAm (blue), Alginate (dark yellow), and PAAm/Alginate copolymer (red).

FIG. 10A is a graph showing the loading-unloading curves under various tensile deformations. The stretching rate were fixed as $\lambda°=2$ min$^{-1}$. FIG. 10B is a graph showing the plastic strain after unloading with respect to maximum applied strain as a function of maximum applied stretch. The plastic strain ratio was not changed much by changing applied stretch, and only 15% plastic deformations were remained after unloading even after extreme stretch $\lambda=13$. FIG. 10C and FIG. 10D are a series of line graphs showing repeated tensile test and fracture test for second cycle, demonstrating self-healing properties of PAAm/Alginate IPN gels. FIG. 10C is a line graph showing repeated tensile tests of IPN gels. Samples were loaded up to the maximum stretch ($\lambda_{max}$) of first cycle and unloaded to the initial stretch (dark yellow), followed by an immediate second loading (blue) or second loading after 1 day (red). FIG. 10D is a line graph showing the toughness of second loading of IPN gels as a function of maximum stretch of first cycle. Samples: PAAm-13.55-0.06/Alginate-2.26-13.28 IPN gels (water content: 86 wt.-%).

FIGS. 21A-C are diagrams showing synergy between alginate and polyacrylamide. A, In the polyacrylamide gel, for the notch to turn into a running crack, only the polyacrylamide chains crossing the crack plane need to break, and chains elsewhere remain intact. B, In the alginate gel, for the notch to turn into a running crack, only the ionic crosslinks for the chains crossing the crack need to break, and ionic crosslinks elsewhere remain intact. C, In the hybrid gel, the polyacrylamide chains bridge the crack and stabilize deformation in the background, the chemical interactions between the networks transfer the load over a large zone, and the ionic crosslinks between alginate chains break and provide inelastic deformation over this large zone around the root of the notch.

FIGS. 27A and 27D are schematics of an alginate gel depicting the G blocks on different polymer chains forming ionic crosslinks through Ca2+. FIGS. 27B and 27E are schematics of a polyacrylamide gel depicting the polymer chains forming covalent crosslinks through MBAA. FIGS. 27C and 27F are schematics of an alginate-polyacrylamide hybrid gel depicting the two types of polymer networks intertwined.

DETAILED DESCRIPTION

Figure 1A:
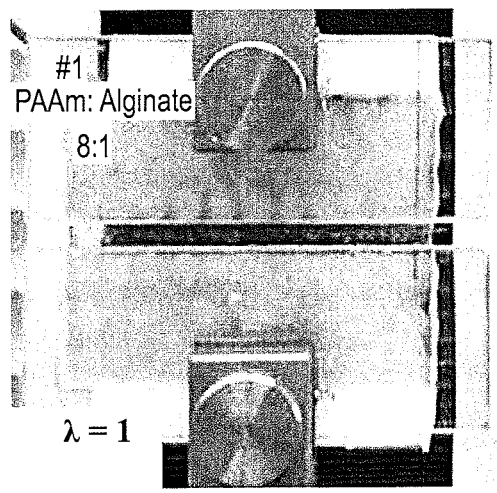
FIGS. 1A-D are a series of photographs showing that a polyacrylamide (PAAm)-alginate hydrogel is extremely stretchable and tough.

Hydrogels serve as an excellent material which has the potential to be used as natural tissues. However prior to the invention, hydrogels were limited in their usefulness due to their softness, brittleness, or lack of strength.

Conventional hydrogels do not exhibit high stretchability; for example, an alginate hydrogel ruptures when stretched to about 1.2 times its original length. Some synthetic elastic hydrogels have achieved stretches in the range 10-20, but these values are markedly reduced in samples containing notches. Described herein is the synthesis of hydrogels from polymers forming ionically and covalently crosslinked networks. Although such gels contain ~90% water, they can be stretched beyond 20 times their initial length, have fracture energies of ~9,000 J m$^2$, and are characterized by Young's modulus values in the megaPascal range. Even for samples containing notches, a stretch of 17 is demonstrated. The gels' toughness is attributed to the synergy of two mechanisms: crack bridging by the network of covalent crosslinks, and hysteresis by unzipping the network of ionic crosslinks. Furthermore, the network of covalent crosslinks preserves the memory of the initial state, so that much of the large deformation is removed on unloading. The unzipped ionic crosslinks cause internal damage, which heals by re-zipping.

Such tough gels are useful in clinical and non-clinical applications. However prior to the invention, most of the currently available hydrogels lacked strength, toughness, and frictional properties. For example, cartilage, which contains around 75% water, has a fracture toughness value around 1000 J/m$^2$. In contrast, most of the conventional hydrogels have the toughness in the range of 1~100 J/m$^2$. In the case of actuators and artificial muscles, strong gels are ideal candidates to serve as muscle-like materials because they should be mechanically strong to carry a significant load. Also, strong gels are needed in drug delivery to change the design and use of capsules and patches. Implantable long-term drug delivery devices also need gels with enhanced mechanical properties.

There is an increasing demand for hydrogels with enhanced mechanical properties, but conventional hydrogels have poor mechanical properties. High toughness of naturally occurring gels is an indication that it is possible to enhance the mechanical performance of synthetic hydrogels. Inspired by this fact, many attempts were taken along with recent innovations in synthetic chemistry such as triblock copolymers (M. E. Seitz, D. Martina, T. Baumberger, V. R. Krishnan, C. Hui, K. R. Shull, Soft Matter, 2009, 5, 447-456), Nanocomposite hydrogels (K. Haraguchi, T. Takehisa, Adv. Mater., 2002, 14, 1120-1124), slide-ring gels (K. Ito, Current Opinion in Solid State and Materials Science, 2010, 14, 28-34), Tetra-Poly (ethylene glycol) (PEG) gels (T. Sakai, T. Matsunaga, Y. Yamamoto, C. Ito, R. Yoshida, S. Suzuki, N. Sasaki, M. Shibayama, Ung-il Chung, Macromolecules, 2008, 41, 5379-5384), silica nanoparticles with Poly (dimethylacrylamide) (PDMA) (W-C. Lin, W. Fan, A. Marcellan, D. Hourdet, C.Creton, Macromolecules, 2010, 43, 2554-2563), etc. Among them, a double network hydrogel introduced by Gong et al (J. P. Gong, Y. Katsuyama, T. Kurokawa, Y. Osada, Adv. Mater., 2003, 15, 1155-1158) has obtained much attention due to high mechanical strength and fracture toughness. It is comprised of two independently crosslinked networks; Poly (2-acrylamido-2-methylpropanesulfonicacid) (PAMPS) and PAAm. The rigid, brittle PAMPS first network serves as an energy dissipation mechanism and the soft, ductile PAAm network assists in broadening the fracture zone to maximize dissipation. They have achieved high toughness in the range of 100-1000 J/m$^2$. However, due to their mechanism of previous DN hydrogels, once the first network has been fractured, the mechanical response is dominated by the much softer second network, and the high stiffness and toughness is lost.

The hydrogel described herein overcomes this significant drawback of earlier hydrogel. The improved hydrogels described herein differ from previous hydrogels in three significant ways: (1) toughness, e.g., at least 10 times tougher and more durable compared to previous gels; (2) defect resistance, e.g., durable gel is not prone to development of tears; and (3) self-healing, e.g., time-depending restoration of mechanical properties. With prior hydrogels, once a defect occurs, failure of the gel was imminent. The improved hydrogels of the invention are resistance to defects, and even if a defect occurs, the gel maintains its toughness and does not fail (FIGS. 1A-D).

An interpenetrating network (IPN) hydrogel, which has great mechanical performance without the need to sacrifice one network, was made by combining covalently crosslinked and ionically crosslinked polymer networks. PAAm and alginate were selected as the covalently crosslinked network and ionically crosslinked network, respectively, and the synthesis was carried out in a one step process. Under the optimized crosslinking densities and polymer ratio, the PAAm/alginate IPN hydrogel which has ~90% water content has a greater enhancement of the mechanical properties, at least an order of magnitude increase in fracture toughness (around 9000 J/m$^2$) over the double network hydrogel introduced by Gong et al, with a high stretch value, i.e., around 21. Moreover, PAAm/alginate IPN hydrogel also shows self-healing properties; 54.6% energy density was recovered in a $2^{nd}$ loading after storing the sample at 80° C. for 1 day. This improved hydrogel opens up the use of these types of hydrogels in new or different applications (compared to present hydrogel uses) and also improves the performance in current applications (e.g., uses described in U.S. patent application Ser. Nos. 13/305,088, 12/992,617, 12/867,426, 13/264,243, 61/480,237, 61/479,774, 61/493, 398, 61/535,473, each of which is hereby incorporated by reference).

Described herein is the synthesis of PAAm/alginate IPN hydrogel and how the mechanical properties of PAAM/alginate IPN hydrogel were changed by controlling the crosslinker densities and polymer ratios by tensile and fracture tests. The mechanism governing the extremely high toughness of PAAm/alginate hydrogel is also described. The energy recovery of $2^{nd}$ loading was measured by repeated tensile test.

Tough Hydrogels

Hydrogels with enhanced mechanical properties have increasing demand in many applications. However, the soft, weak and brittle behaviors of the conventional hydrogels have limited the applications where mechanical properties are important. PAAm (Polyacrylamide)-alginate Interpenetrating network (IPN) hydrogels herein described are characterized by extremely high toughness ~9000 J/m2 with a high stretch value (~21), although it contains 86 wt.-% water. Moreover, PAAm-Alginate gel shows self-healing properties. As described in detail below, around 74% energy density of the first loading was recovered in the second loading after storing at 80° C. for one day from the first unloading. The hydrogels are physiologically compatible and have little or no toxicity after soaking the fabricated gels to eliminate unreactive monomers.

Example 1: Manufacture of IPN Hydrogel Compositions

The following materials and methods were used to make and test the improved hydrogel compositions.

Materials

Acrylamide (AAm; Sigma, A8887) and alginate (FMC Biopolymer, LF 20/40) were used as the base materials of the network. N,N-methylenebisacrylamide (MBAA; Sigma, M7279) was used as the cross-linking agent for AAm gel. Ammonium persulfate (AP; Sigma, A9164), N,N,N',N'-tetramethylethylenediamine (TEMED; Sigma, T7024) were used as the photo initiator and accelerator for the ultraviolet (UV) gelation reactions, respectively. Calcium sulfate slurry ($CaSO_4.2H_2O$; Sigma, 31221) was used as the ionic cross-linker for alginate gel. All materials were used as received.

Gel Preparation

The interpenetrating network (IPN) gels were prepared by dissolving alginate and AAm monomer powders in deionized water. The water concentration [water wt./(alginate+AAm+water wt.)]×100 was fixed as 88.6 wt.-% throughout the entire experiments, and polymer ratios were varied by mixing different amounts of alginate and AAm powders. MBAA 0.06 wt.-% and AP 0.17 wt.-% with respect to the weight of AAm monomer were added as a cross-linker for AAm and a photo initiator, respectively. After degassing in vacuum chamber, calcium sulfate slurry 13.28 wt.-% with respect to the weight of alginate monomer and TEMED 0.25 wt.-% with respect to the weight of AAm monomer were lastly added as the ionic cross-linker for alginate and accelerator.

The solutions were poured into a glass mold which has 75.0×150.0×3.0 mm$^3$ size vacancy and covered with 3 mm thick transparent glass plate. The gels were cured by the ultraviolet light cross-linker (UVC 500, Hoefer) for 1 hour with 8 W power and 254 nm wavelength. The gels were then left in humid box for 1 day to stabilize reactions before performing mechanical tests. Hereafter, the IPN gels are referred to as $P_1$-$x_1$-$y_1$/$P_2$-$x_2$-$y_2$, where $P_i$, $x_i$, and $y_i$ (i=1, 2) are the abbreviated polymer name (i.e. PAAm), weight concentration of monomer in wt.-% with respect to the weight of water [e.g. $x_1$=(PAAm wt./Water wt.)×100], and the crosslinker concentration in wt.-% with respect to the monomer of the ith network [e.g. $y_1$=(MBAA wt./PAAm wt.)×100], respectively.

Example 2: Characterization of Hydrogel Properties

Physical and chemical characteristics were evaluated as follows.

Mechanical Tests

Figure 3B:
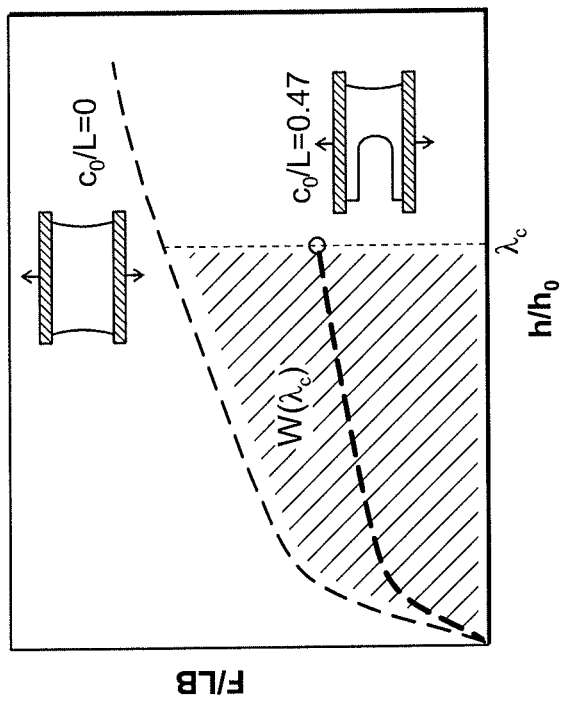
FIGS. 3A-D are a series of schematics and line graphs showing experimental determination of fracture energy.
Figure 3A:
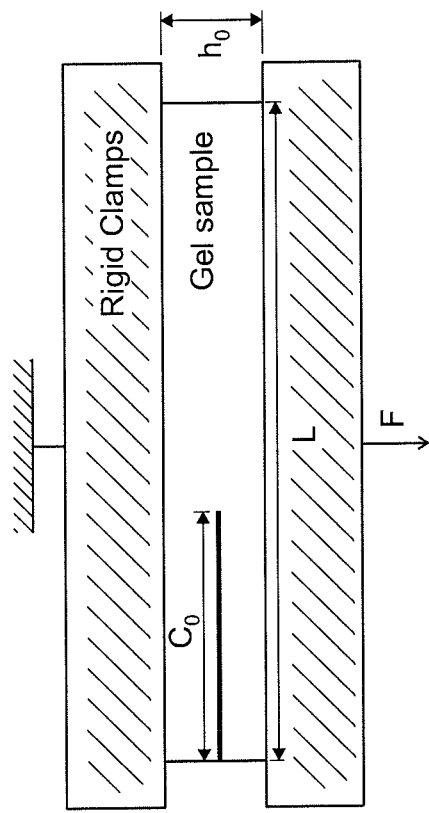

Before the mechanical tests, the surfaces of the hydrogels were dried with $N_2$ gas for 1 minute to remove water from the gel surfaces. Four stiff polystyrene plates were glued with superglue to clamp the gel as shown in FIG. 3A. At the end, 75.0 (L)×5.0 ($h_0$)×3.0 (t) mm$^3$ size test specimens were prepared for the tests. All mechanical tests were performed at room temperature on a tensile machine (Instron model 3342) with 500 N capacity load cell and nominal stress and stretch were recorded. The stretch rate was kept constant as $\lambda°=2$ min$^{-1}$.

Figure 2:
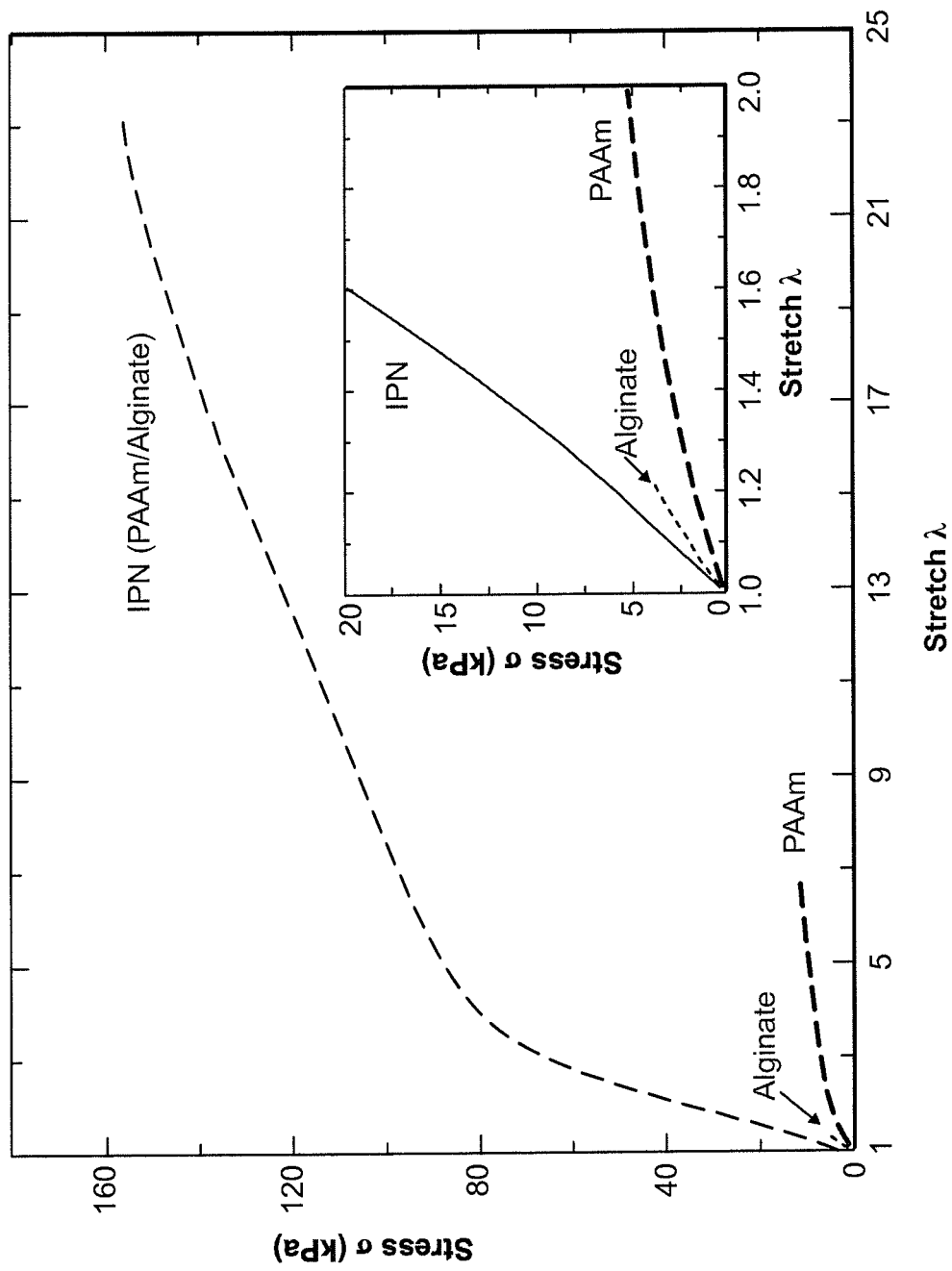
FIG. 2 is a line graph showing stress-stretch curves under uniaxial tension. Blue: PAAm-14.05-0.06 SN gel (water content: 88 wt.-%). Dark yellow: Alginate-1.76-13.28 SN gel (water content: 97 wt.-%). Red: PAAm-14.05-0.06/Alginate-1.76-13.28 IPN gel (water content: 86 wt.-%).

Tensile Test (FIG. 1A, FIG. 2)

PAAm-14.05-0.06/Alginate-1.76-13.28 IPN gel was subjected to tensile test. The pictures for reference and current states of tensile test are shown in FIG. 1A to demonstrate the high stretchability of PAAm/Alginate IPN gel. As shown in FIG. 1A, PAAm/Alginate IPN gel sustained huge tensile stretch $\lambda=21$, although it contains 86 wt.-% water. This huge tensile rupture stretch is remarkable, because high tensile rupture stretch results in enhanced performances and improved safety in applications. Moreover, because hydrogels which are well known for the high toughness, such as polyhydroxyethyl methacrylate (PHEMA), Polyvinyl Alcohol (PVA), and DN hydrogel have tensile rupture stretches around $\lambda=2.6$, $\lambda=6$, and $\lambda=7.4$, respectively (M. Kita, Y. Ogura, Y. Honda, S. H. Hyon, W. Cha, and Y. Ikada, Graefe's Arch. Clin. Exp. Ophthalmol., 1990, 228, 533-537; Q. M. Yu, Y. Tanaka, H. Furukawa, T. Kurokawa, and J. P. Gong, Macromolecules, 2009, 42, 3852-3855), PAAm/Alginate IPN gels are particularly useful when there are mechanical failure issues.

The dramatic change of mechanical properties for PAAm/Alginate IPN gel is shown in FIG. 2 by comparing IPN hydrogel with PAAm single-network (SN) and Alginate SN gels. To make an effective comparison, crosslinking densities and polymer concentrations of individual networks for SN and IPN were fixed, in particular, PAAm-14.05-0.06 single-network (SN) gel, Alginate-1.76-13.28 SN gel, and PAAm-14.05-0.06/Alginate-1.76-13.28 IPN gel were used. The engineering stress, σ, under tensile test was plotted as a function of stretch, λ. Here, σ is defined as the measured load divided by the undeformed cross-sectional area, and λ is defined as the measured length divided by the undeformed gauge length. As shown in FIG. 2, IPN gel shows highly improved mechanical properties in terms of both ultimate stress and rupture stretch. PAAm and Alginate SN gels were ruptured at 11.44 and 3.65 kPa stress values, respectively, while PAAm/Alginate IPN gel has sustained a stress of 156.23 kPa, which is more than 13 times that was sustained by the SN gels. Also, the rupture stretch of the IPN gel is $\lambda \approx 23$, which is much higher than that of both the PAAm SN gel ($\lambda \approx 6$) and the Alginate SN gel ($\lambda \approx 1.2$).

Two distinguishing characteristics were revealed in the characterization process. First, in the small strain region, the elastic modulus of PAAm/Alginate IPN gel is E=28.57 kPa, which is closer to the sum of the elastic moduli of the PAAm SN gel (E=8.22 kPa) and the Alginate SN gel (E=16.95 kPa). It means the rule of mixture can be used to calculate the elastic modulus of IPN gel. Second, Alginate SN gel has extremely small rupture stretch ($\lambda \approx 1.2$) and PAAm SN gel has relatively small rupture stretch ($\lambda \approx 6$) compared to the IPN gel. However, when the IPN gel was synthesized by mixing two networks, IPN gel showed huge rupture stretch $\lambda \approx 23$ rather than an intermediate value between the rupture stretches of SNs. This change of rupture stretch cannot be explained with general idea such as rule of mixture and is clarified below.

Figure 1B:
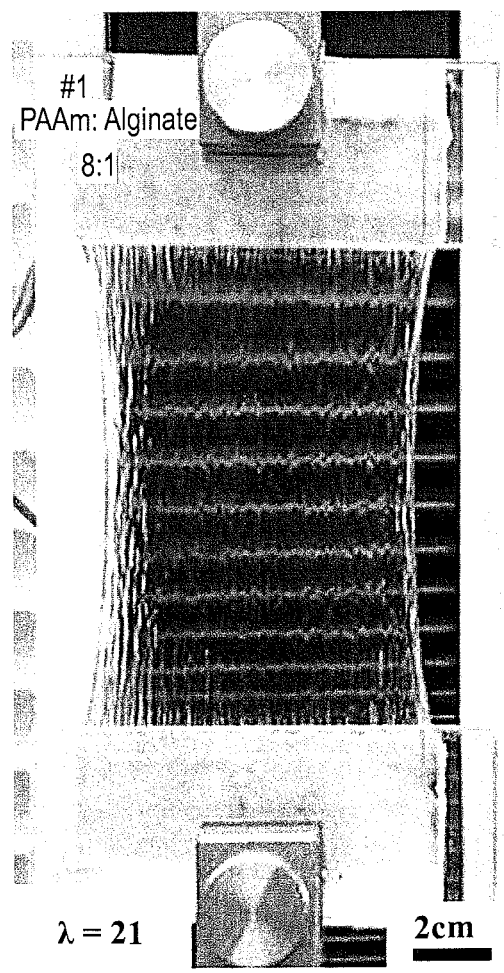
Figure 1C:
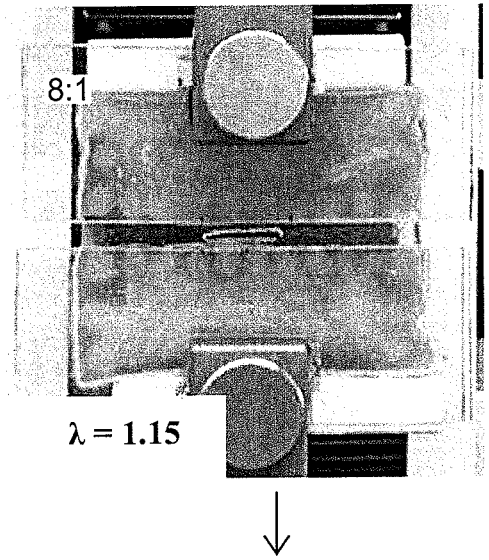

Fracture Test (FIG. 1B, FIG. 3A,B)

FIG. 1B demonstrates how flaw-insensitive the PAAm-14.05-0.06/Alginate-1.76-13.28 IPN gel is. The initial flaw was introduced by a razor blade to a value of $2c_0=2$ cm and the sample was stretched perpendicular to the pre-crack direction. As shown in FIG. 1B, even until high stretch $\lambda \sim 17$, the crack was not propagated.

To investigate the fracture toughness of the hydrogel, Rivlin's method (Rivlin et al., 1953, J. Polym. Sci. 10, 291-318; M. Kita, Y. Ogura, Y. Honda, S. -H. Hyon, W. Cha, and Y. Ikada, Graefe's Arch. Clin. Exp. Ophthalmol., 1990, 228, 533-537; Q. M. Yu, Y. Tanaka, H. Furukawa, T. Kurokawa, and J. P. Gong, Macromolecules, 2009, 42, 3852-3855) was used with the fracture test specimens shown in FIG. 3A. An initial edge crack ($c_0$) was introduced by razor blade in lengths of $c_0/L \approx 0.5$ to the fracture test specimens. Tensile tests and fracture tests were carried out until the specimen reached ultimate failure. Movies of crack propagation of the fracture tests were recorded at a typical rate of 30 frames/sec to find the onset crack propagation stretch ($\lambda_c$).

When the fracture test pieces were deformed in a direction parallel to the dimension $h_0$, the region which is far from the crack front has uniform strain energy density(Rivlin et al., 1953, J. Polym. Sci. 10, 291-318). When the crack propagation was occurred, the increase in the crack length of amount (dc) does not alter the state of strain near the crack tip but causes the cracked region to grow at the expense of the uniform strain energy density region. Thus, if the region which is far from the crack front has uniform strain energy density (W), an increase in crack length (dc) will release the energy (dw) of $W \cdot h_0 \cdot t \cdot dc$. Where $h_0$ is the length of the test piece between the clamps and t is the thickness, and both these quantities have been measured in the undeformed state. So, $$-(\partial w/\partial c)_h = W \cdot h_0 \cdot t$$

The suffix h indicates that the differentiation is carried out at a constant displacement. The strain energy density (W) is a function of applied stretch (λ). If the onset critical stretch for crack propagation ($\lambda_c$) is known, the fracture toughness for crack initiation ($\Gamma_0$) can be given by, $\Gamma_0 = W(\lambda_c) \cdot h_0$ In the measurement for the toughness in FIG. 3B, two specimens, one for tensile test and the other for fracture test, were prepared with same dimensions. Fracture test was performed with notched specimen to obtain the onset critical stretch for crack propagation ($\lambda_c$). Initial notch sizes ($c_0$) have been varied, but comparable critical stretches were obtained when the initial notch sizes are in the range of $0.13 \leq c_0/L \leq 0.8$. From the tensile test which was performed with un-notched specimen, the strain energy density $W(\lambda_c)$ was calculated by integrating the area under the stress-stretch curves of tensile test, corresponding to the onset crack propagating stretch $\lambda_c$.

The toughness measuring method was verified with two different methods, tensile test with various crack lengths and double peeling test (Rivlin et al., 1953, J. Polym. Sci. 10, 291-318). Although the crack propagation was occurred at a huge stretch, the toughness of the experiment matched very well with the other methods.

Figure 3D:
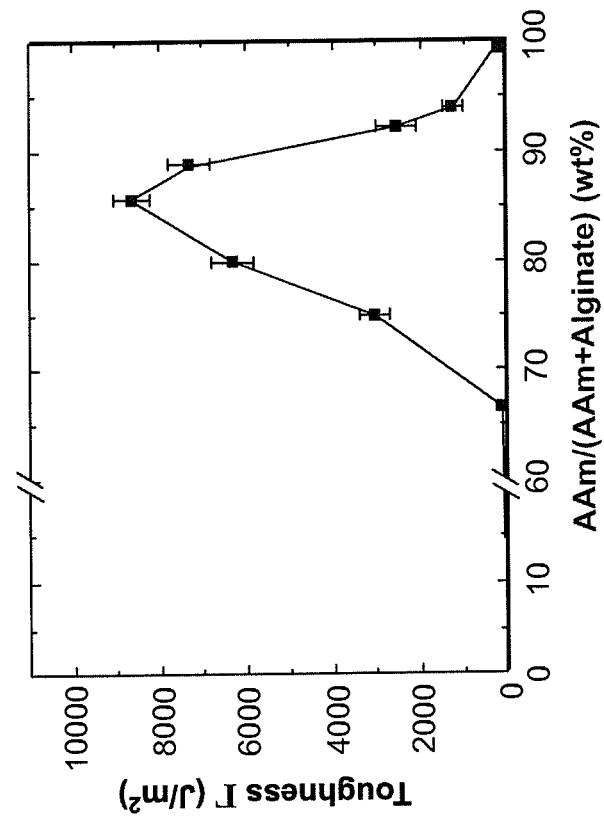
Figure 3C:
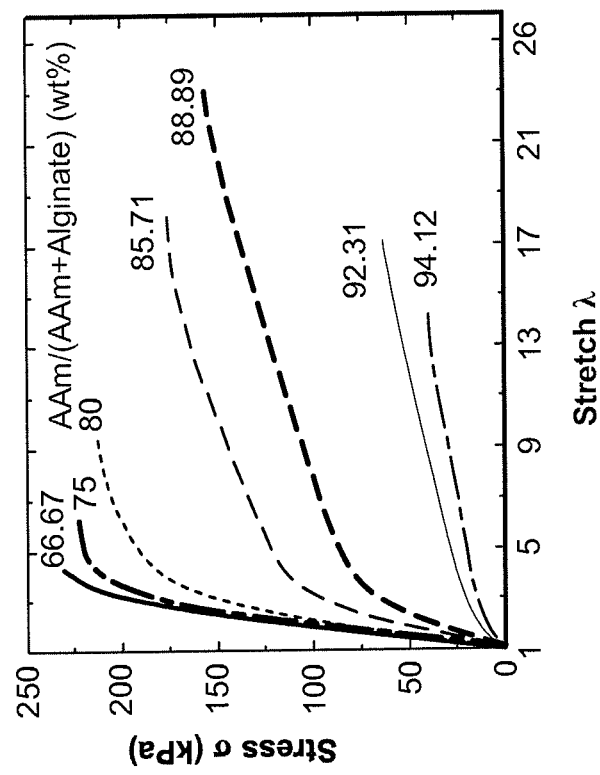

The Effects of Crosslinking Densities and Polymer Ratio (FIG. 3C, D)

One very effective way to control the toughness of the PAAm/alginate IPN gel is by controlling the crosslinking density of each network. Since two different crosslinkers were used for the PAAm/alginate IPN gel, MBAAm as a covalent crosslinker for PAAm network and $CaSO_4$ as a ionic crosslinker for alginate network, the crosslinking densities were optimized one by one, by fixing one crosslinking density. The effects of crosslinker densities were studied with a given PAAm ratio [AAm wt./(AAm+alginate wt.)]× 100=91 wt.-% and water concentration 86 wt.-%. To study the MBAAm effect, the crosslinking density of the alginate network was fixed at 26.57 wt.-%, and the crosslinking density of the PAAm network was varied from 0.031 to 0.124 wt.-%. The elastic moduli of PAAm/alginate IPN gels were gradually increased by adding more crosslinker for PAAm network. However, even with a highly crosslinked PAAm, the total stiffness of IPN gel was not increased a lot, because PAAm network is much more compliant than alginate network. The highest fracture toughness was obtained when the crosslinking density of the PAAm network was 0.062 wt.-%. The reason why IPN gel got optimum crosslinker density for PAAm network in terms of the toughness was understood as follows. When the crosslinker density becomes too high, the distance between two crosslinked points for PAAm network will be shortened. As Lake and Thomas pointed out from their work (Lake et al., 1967, Proc. R. Soc. A 300, 108-119), since the rupture of chain will also relax the stored energy between crosslinked points, if the chain has shorter distance between crosslinked points, the energy required to rupture a chain will become smaller, although only one of these monomer units will in fact be ruptured. For another extreme case, if the crosslinker density becomes too low, since forces are transmitted primarily via the crosslinks, PAAm network can't spread applied force to large area. Therefore, very low crosslinker density will cause small process zone size and small toughness.

To study the $CaSO_4$ effect, the crosslinking density of the PAAm network was fixed at 0.06 wt.-%, and the crosslinking density of the alginate network was varied from 3.32 to 53.15 wt.-%. The elastic moduli of PAAm/alginate IPN gels were proportionally increased by increasing the amount of the crosslinking density of alginate network. However, the critical stretch for crack propagation was decreased by increasing the amount of the crosslinking density of alginate network. So, the highest fracture toughness was obtained when the crosslinking density of the alginate network was 13.28 wt.-%. The reason why IPN gel got optimum crosslinker density for alginate network in terms of the toughness was understood like follows. When the crosslinker density becomes higher, the yield stress for alginate network will also gradually be larger. After some point, the total dissipated energy by plastic deformation of alginate chain will be decreased by increased yield stress, and toughness will also be decreased. On the other hand, when the IPN gel has very low $Ca^{2+}$ concentration, the total amount of plastic deformation will be very small, and it will decrease the toughness.

The other way to control the fracture toughness is by controlling the polymer ratio between PAAm network and alginate network. Crosslinking densities of the alginate and PAAm networks were fixed at 13.28 wt.-% and 0.06 wt.-%, respectively. The PAAm ratio, [AAm wt./(AAm+alginate wt.)]×100, was varied from 66.67 to 94.12 wt.-% and the corresponding stress-stretch curves of tensile tests are posted in FIG. 3C. When the amount of AAm was increased, the elastic modulus of PAAm/alginate IPN gel was reduced. However, the elongation of PAAm/alginate IPN gel was increased until the PAAm ratio was 88.89 wt.-%, and was decreased after that point. In the fracture test, the critical stretch for rupture has the same trend with the elongation. When the PAAm ratio was varied from 66.67 to 94.12 wt.-%, the highest mean critical stretch $\lambda_c$=15.71 was obtained at the PAAm ratio of 88.89 wt.-%. The fracture toughness was calculated by combining the tensile tests with the fracture tests, and the results are posted in FIG. 3D. The highest fracture toughness was obtained when the PAAm ratio was 85.71 wt.-%, and the corresponding number is 8696 $J/m^2$.

This huge fracture toughness is remarkable; because PAAm and alginate SNs have a fracture toughness in the range of 10 to $10^2$ $J/m^2$ (Y. Tanaka, K. Fukao, and Y. Miyamoto, Eur. J. Phys., 2000, E 3, 395-401). Furthermore, hydrogels which are well known for the high toughness, such as PHEMA-vinyl pyrrolidone-phenethyl methacrylate copolymers have a fracture toughness around $\Gamma$=347 $J/m^2$ (A. P. Jackson, Biomaterials, 1990, 11, 403-407). Even DN proposed by Gong et al, the toughest hydrogel so far, has the fracture toughness in the range of $10^2$ to $10^3$ $J/m^2$ (Q. M. Yu, Y. Tanaka, H. Furukawa, T. Kurokawa, and J. P. Gong, Macromolecules, 2009, 42, 3852-3855).

Figure 4A:
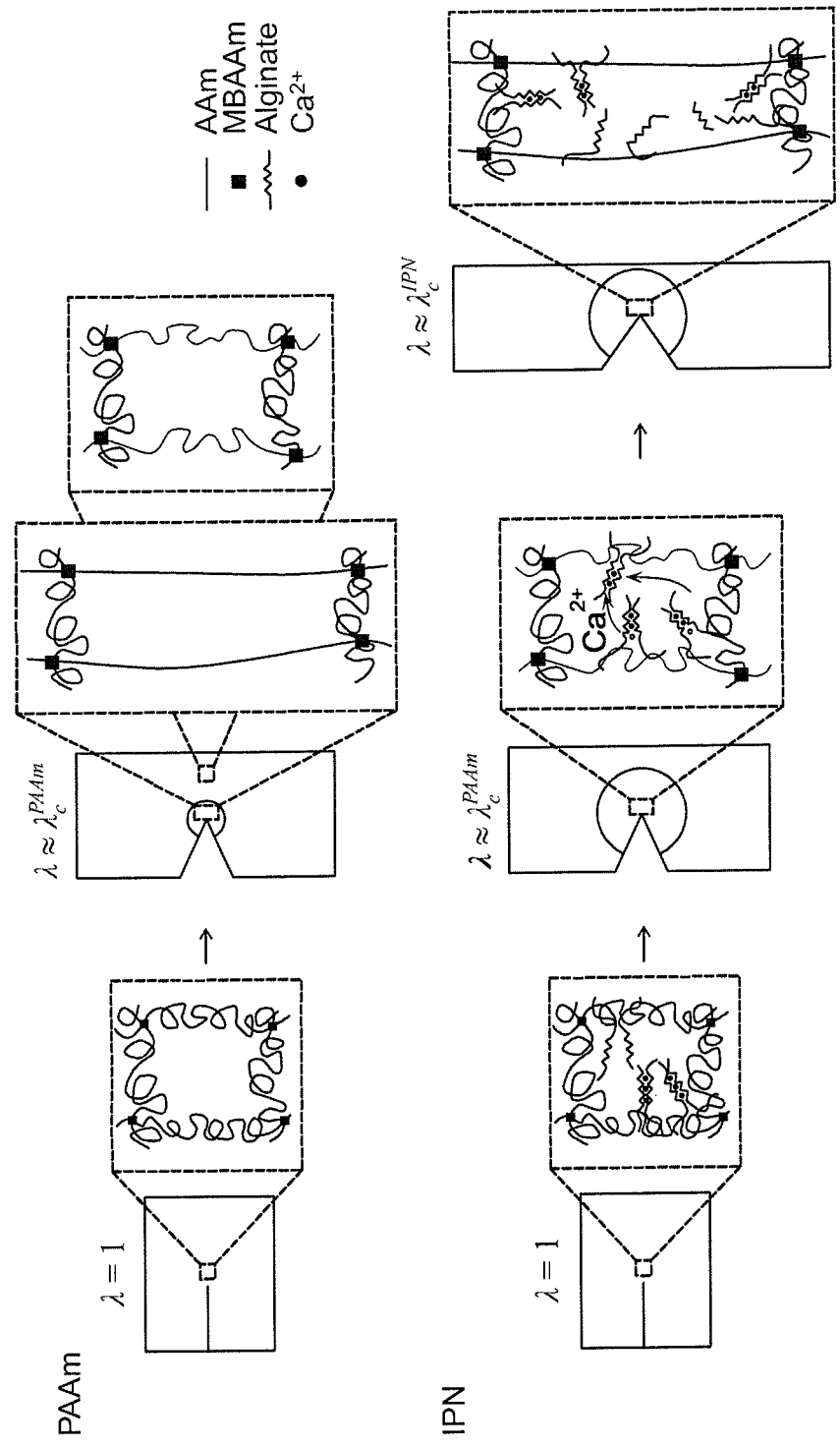
FIGS. 4A-C are a series of schematic diagrams and line graphs.

Mechanism Governing the High Toughness (FIG. 4A)

Assuming PAAm network has long enough chain to be stretched to the critical stretch of IPN gel, which means, if there are no flaws in the sample, PAAm network itself can be stretched up to the critical stretch of IPN gel $\lambda \approx \lambda_c^{IPN}$. However, because PAAm network behaves like elastic material, the stress concentration near the initial flaws will be significant and also will bring small plastic zone size. Therefore, when the PAAm SN gel was stretched around $\lambda \approx \lambda_c^{PAAm}$, although the area where is far from crack tip can be stretched more, because the crack tip area already reached to the maximum elongation, the crack propagation will be occurred. On the contrary, when the ionically crosslinked alginate networks were added to the PAAm back bone networks, alginate network would help to dissipate the energy with plastic deformation without breaking alginate chain itself; when the alginate network deforms, calcium ions are dissociated from the crosslinked points and will re-associate in another alginate chain. As a result, plastic behavior of ionically crosslinked alginate assist to broaden the plastic zone size and make the PAAm/alginate IPN gel tough. When the PAAm/alginate IPN gel was stretched around $\lambda \approx \lambda_c^{PAAm}$, even the network which is in the crack tip area did not reach to the maximum elongation of PAAm back bone chain because the stress concentration was much smaller than the PAAm SN gel. So the elongation of PAAm/alginate hydrogel is improved compared to the elongation of PAAm SN gel.

Figure 4C:
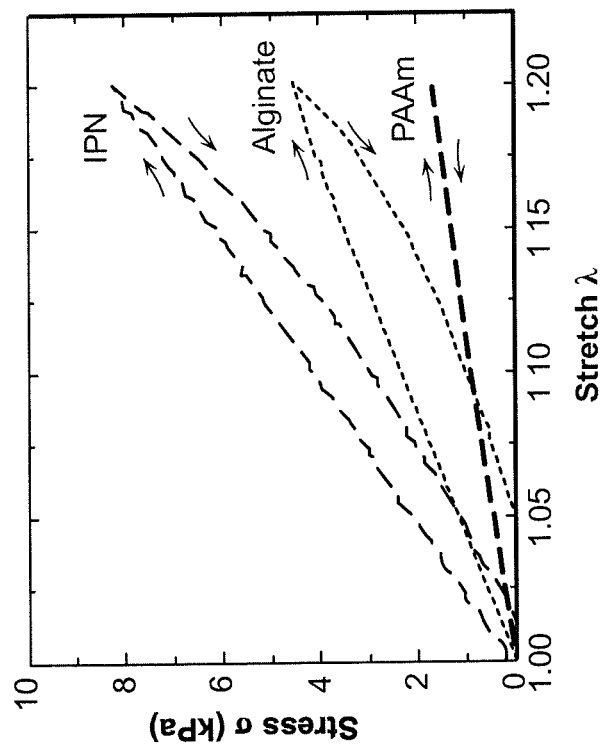
Figure 4B:
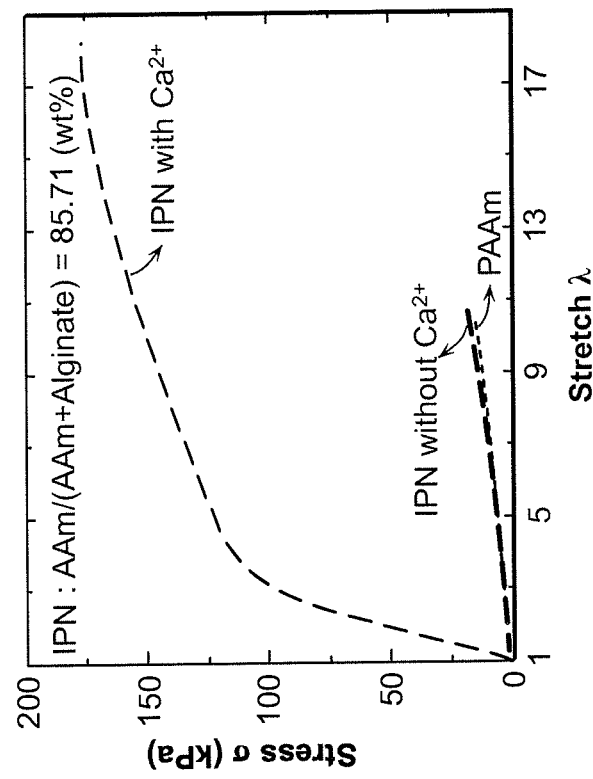

Calcium Ion Effect (FIG. 4B)

The hydrogen bond between —OH groups of alginate and —$NH_2$ groups of PAAm molecules was suggested by analyzing Fourier Transform Infrared (FTIR) spectra of alginate, PAAm, PAAm/alginate IPN (D. Solpan, M. Torun, O. Guven, Journal of Applied Polymer Science, 2008, 108, 3787-3795). If the interaction between two networks effect on the mechanical properties of IPN gel, the interaction between two networks should be included in the mechanism of high toughness of PAAm/alginate IPN gel.

Stress-strain curves for PAAm/Alginate IPN gels with calcium ions and without calcium ions under uniaxial tension were plotted with stress-strain curve of PAAm SN gel in FIG. 4B. Because calcium ions do not affect the interaction between two networks, PAAm/alginate IPN gels without calcium ions may have hydrogen bonds between two networks. However, PAAm/Alginate IPN gels without calcium ions show a very similar stiffness and elongation with PAAm SN gel, even though IPN gel contains alginate chains in it. This means the interaction between two networks doesn't have a large effect on mechanical properties of IPN gel.

The stiffness of PAAm/Alginate IPN gel was increased by adding more calcium ions, the crosslinker for alginate network, due to the increase in total crosslinking density. Furthermore, the stretchability of the IPN gel was enhanced remarkably at the same time. The elongations were doubled in the case of PAAm-13.55-0.06/Alginate-2.26-0 IPN gel when the calcium sulfate was added at the weight ratio of $CaSO_4$/Alginate=13.28%.

Unloading Test (FIG. 4C)

Loading-unloading tensile tests were performed in displacement control for SNs PAAm and alginate, and PAAm/alginate IPN gel without pre-crack. Specimens were loaded to a peak stretch $\lambda$=1.2 and returned to the initial stretch with constant stretch rate $\lambda^\circ$=3.3×$10^{-2}$ $sec^{-1}$. The peak stretch was relatively small; because alginate has a small rupture stretch $\lambda$<1.25. In FIG. 4C, stress-stretch curves for loading-unloading tests were plotted with PAAm and alginate single networks and PAAm/alginate IPN. For a covalently crosslinked PAAm gel, the mechanical response is dominated entirely by an elastic, recoverable response, with little hysteresis. In contrast, ionically crosslinked alginate gel demonstrates considerable hysteresis, indicating significant dissipation of applied strain energy. This energy dissipation of ionically crosslinked alginate gel was understood with breaking and reforming ionic crosslinks idea (E. Pines and W. Prins, Macromolecules, 1973, 6, 888-895). PAAm/alginate IPN gel also has ionic crosslinks and shows similar hysteresis in FIG. 4C. This energy dissipation mechanism serves to increase the fracture toughness of PAAm/alginate IPN gel.

Self-Healing (FIG. 5)

Ionic crosslinking in alginate gels demonstrate reversible associations that permits gel recovery after shear deformation, and ionically crosslinked triblock copolymer hydrogel shows 61% energy recovery in second loading after waiting 12 hours after unloading. So, the distinct advantage of PAAm/alginate IPN gel over covalently crosslinked DN gels is its self-healing ability since double network gels which have no fatigue resistance has the second loading in the same location followed by the unloading behavior of the previous test.

Figure 5B:
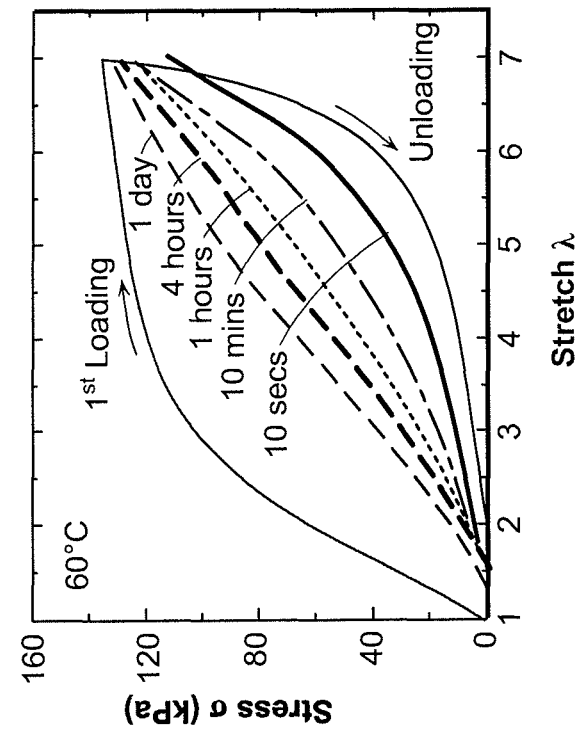
FIGS. 5A-D are a series of line graphs and a dot plot showing repeated tensile tests of IPN gels.
Figure 5A:
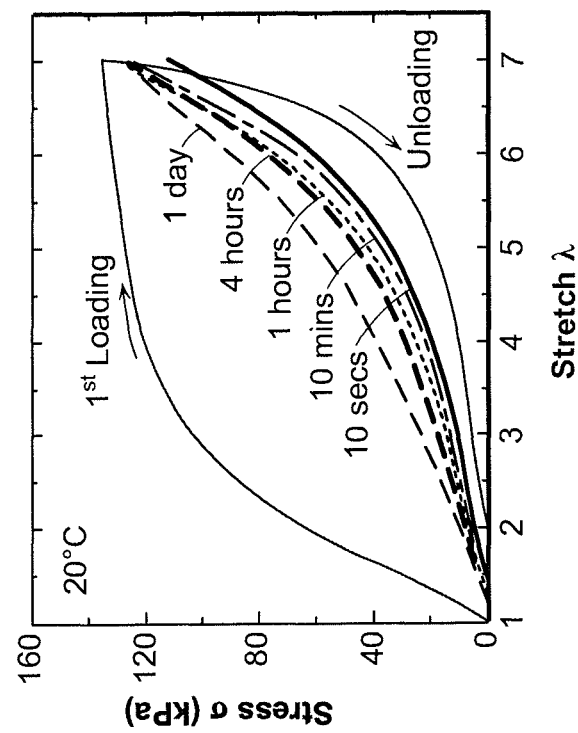
Figure 5D:
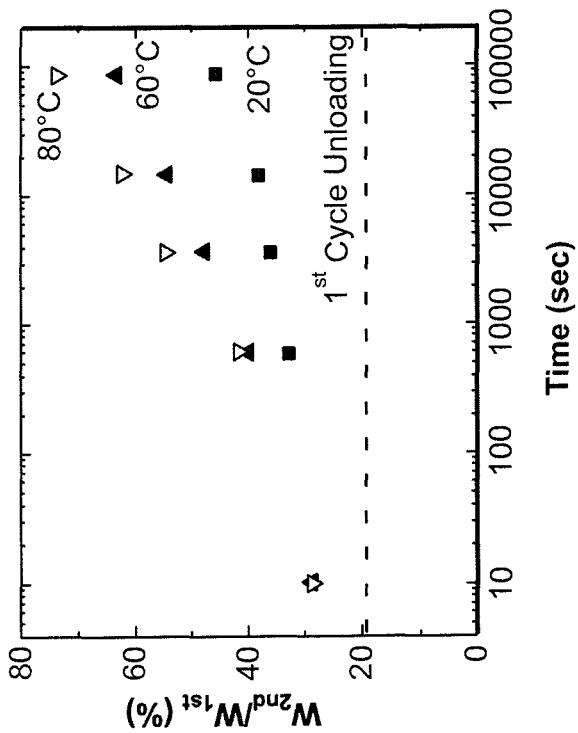
Figure 5C:
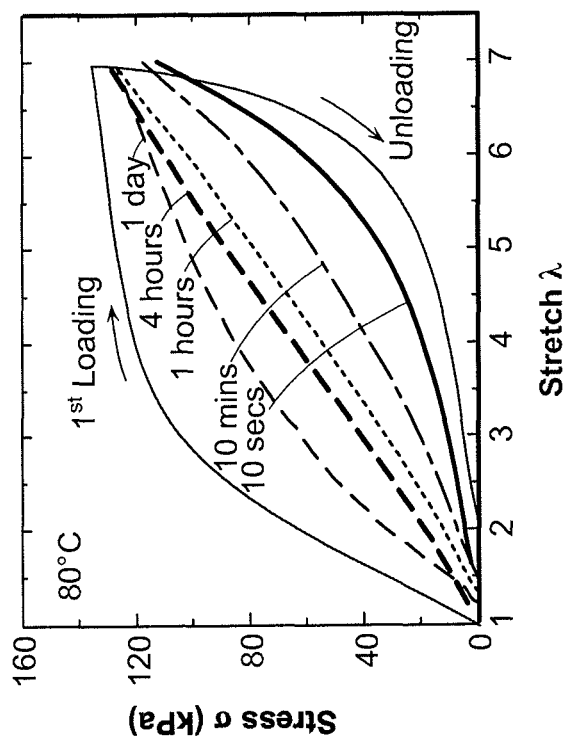

The repeated tensile tests are carried out to reveal the self-healing property of PAAm/Algingate IPN gel. IPN gels are firstly loaded to $\lambda=7$, and unloaded to the initial length with a stretch rate $\lambda°=2$/min. The samples are put into the polyethylene bag and sealed with mineral oil after unloading to prevent the evaporation of the water, and stored in isothermal hot bathes with the temperatures of 20° C., 60° C. and 80° C. The second loadings are followed after keeping the samples in the hot bath for 10 secs, 10 mins, 1 hour, 4 hours and 1 day. As shown in FIG. 5, PAAm/Alginate IPN gel shows big hysteresis in first cycle which is caused by the breaking of ionic bond of alginate network. Thus, in the second loading, IPN gels behave more compliant than $1^{st}$ loading when the stretch was below the maximum stretch of the $1^{st}$ cycle. However, because ionic bond can be healed, PAAm/Alginate IPN gel shows the recovery of the stiffness in the second loading, and the stiffness of the second loading is gradually increased by increasing healing time and by storing the unloaded sample at higher temperature. FIG. 5D plots the normalized energy density of $2^{nd}$ loading as a function of self-healing time with various healing temperature 20° C., 60° C. and 80° C., and the energy density of $1^{st}$ unloading is plotted as a dashed line also. The energy densities are calculated by integrating the under area of the stress-stretch curves up to maximum stretch of $1^{st}$ stretching. As shown in FIG. 5D, the energy density also increased by increasing the healing time and temperature, and PAAm/Alginate IPN gel shows 74.1% energy density of the $1^{st}$ loading during the $2^{nd}$ loading after storing IPN gel in 80° C. for 1 day. Because $1^{st}$ unloading can only take 19.5% energy density of the $1^{st}$ loading, 54.6% energy density is recovered by self healing of IPN gel. There is a time element to self-healing. The cycling requires a healing period to restore mechanical properties.

MBAAm Effect

Figure 6A:
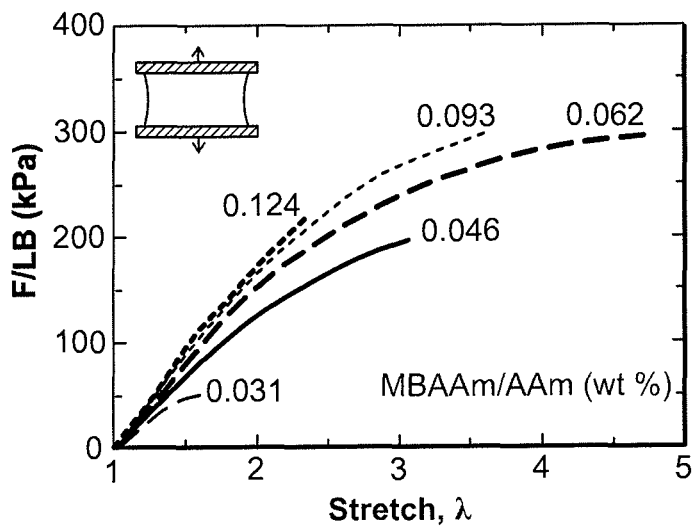
FIGS. 6A-C are a series of line graphs.
Figure 6B:
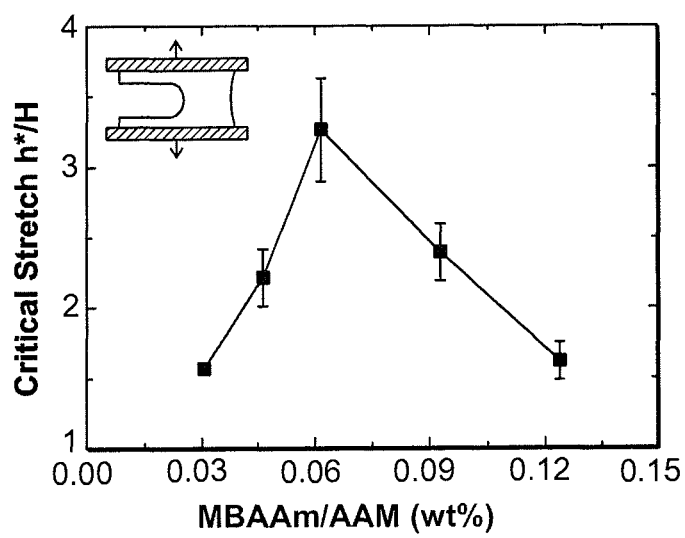
Figure 6C:
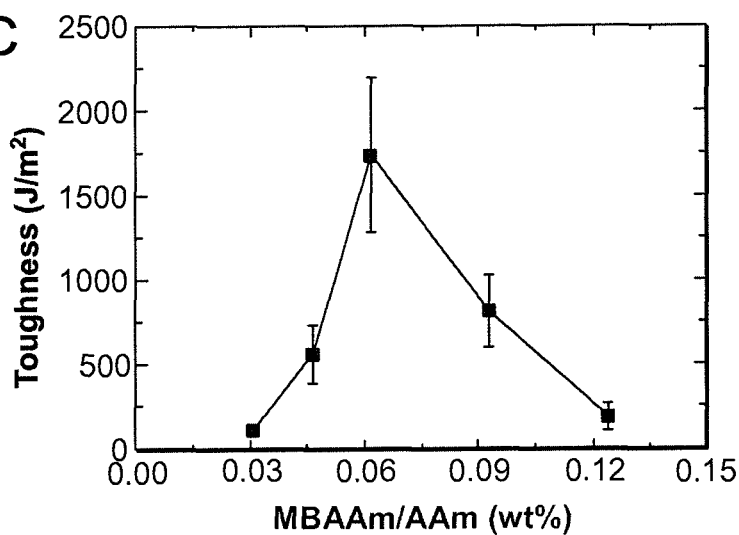

As shown in FIG. 6, one very effective way to control the toughness of the PAAm/alginate IPN gel is by controlling the crosslinking density of each network. Since two different crosslinkers were used for the PAAm/alginate IPN gel, MBAAm as a covalent crosslinker for PAAm network and $CaSO_4$ as a ionic crosslinker for alginate network, the crosslinking densities were optimized one by one, by fixing one crosslinking density. The effects of crosslinker densities were studied with a given PAAm ratio [AAm wt./(AAm+alginate wt.)]×100=91 wt.-% and water concentration 86 wt.-%. To study the MBAAm effect, the crosslinking density of the alginate network was fixed at 26.57 wt.-%, and the crosslinking density of the PAAm network was varied from 0.031 to 0.124 wt.-%. The elastic moduli of PAAm/alginate IPN gels were gradually increased by adding more crosslinker for PAAm network. However, even with a highly crosslinked PAAm, the total stiffness of IPN gel was not increased a lot, because PAAm network is much more compliant than alginate network. The highest fracture toughness was obtained when the crosslinking density of the PAAm network was 0.062 wt.-%. The reason that IPN gel got optimum crosslinker density for PAAm network in terms of the toughness was understood as follows. When the crosslinker density becomes too high, the distance between two crosslinked points for PAAm network will be shortened. Since the rupture of the chain will also relax the stored energy between crosslinked points, if the chain has a shorter distance between crosslinked points, the energy required to rupture a chain will become smaller, although only one of these monomer units will in fact be ruptured. For another extreme case, if the crosslinker density becomes too low, since forces are transmitted primarily via the crosslinks, PAAm network cannot spread applied force to large area. Therefore, very low crosslinker density will cause small process zone size and small toughness.

$CaSO_4$ Effect

As shown in FIG. 7, to study the $CaSO_4$ effect, the crosslinking density of the PAAm network was fixed at 0.06 wt.-%, and the crosslinking density of the alginate network was varied from 3.32 to 53.15 wt.-%. The elastic moduli of PAAm/alginate IPN gels were proportionally increased by increasing the amount of the crosslinking density of alginate network. However, the critical stretch for crack propagation was decreased by increasing the amount of the crosslinking density of alginate network. So, the highest fracture toughness was obtained when the crosslinking density of the alginate network was 13.28 wt.-%. The reason that IPN gel got optimum crosslinker density for alginate network in terms of the toughness was understood as follows. When the crosslinker density becomes higher, the yield stress for alginate network gradually becomes larger. After some point, the total dissipated energy by plastic deformation of alginate chain is decreased by increased yield stress, and toughness is also decreased. On the other hand, when the IPN gel has a very low $Ca^{2+}$ concentration, the total amount of plastic deformation is very small, and it decreases the toughness.

Polymer Ratio

Figure 8A:
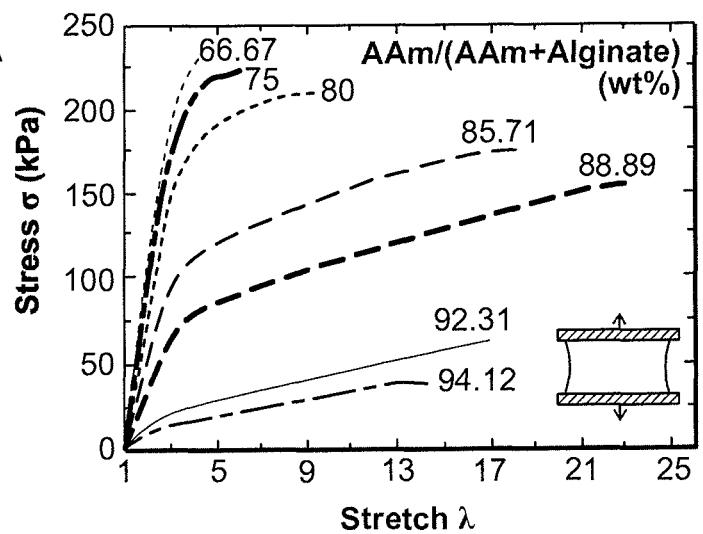
FIGS. 8A-C are a series of line graphs.
Figure 8B:
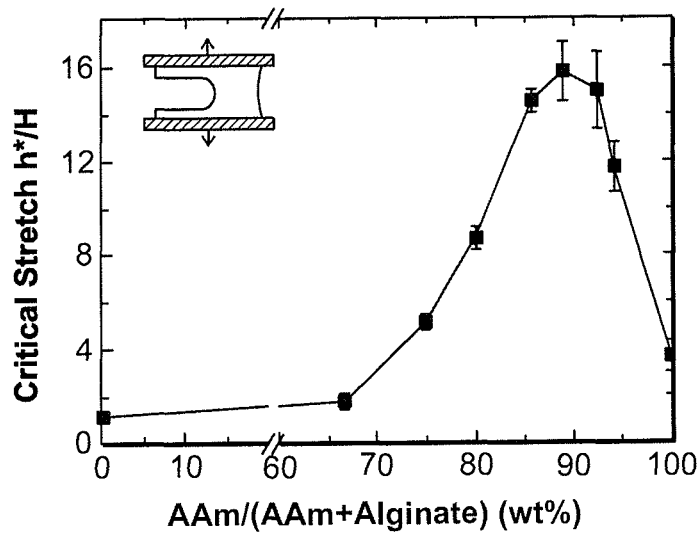
Figure 8C:
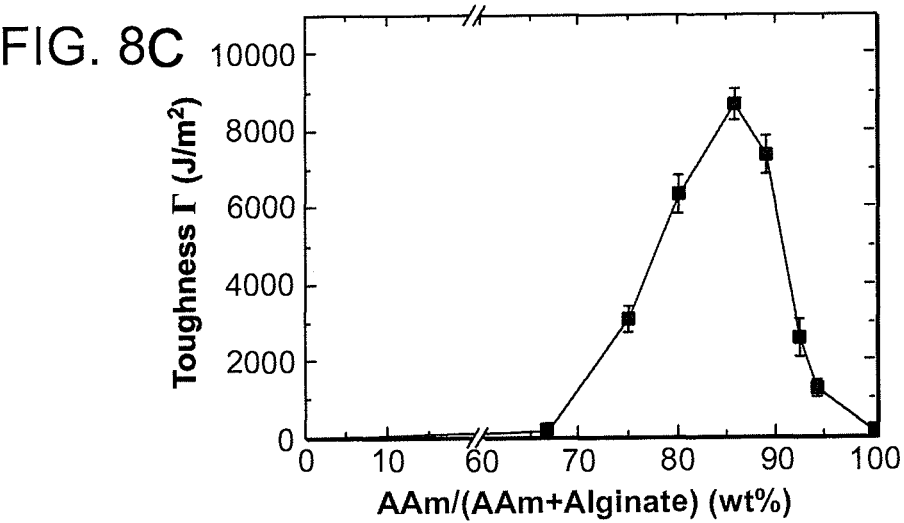

As shown in FIG. 8, the other way to control the fracture toughness is by controlling the polymer ratio between PAAm network and alginate network. Crosslinking densities of the alginate and PAAm networks were fixed at 13.28 wt.-% and 0.06 wt.-%, respectively. The PAAm ratio, [AAm wt./(AAm+alginate wt.)]×100, was varied from 66.67 to 94.12 wt.-% and the corresponding stress-stretch curves of tensile tests are posted in FIG. 3C. When the amount of AAm was increased, the elastic modulus of PAAm/alginate IPN gel was reduced. However, the elongation of PAAm/alginate IPN gel was increased until the PAAm ratio was 88.89 wt.-%, and was decreased after that point. In the fracture test, the critical stretch for rupture has the same trend with the elongation. When the PAAm ratio was varied from 66.67 to 94.12 wt.-%, the highest mean critical stretch $\lambda_c=15.71$ was obtained at the PAAm ratio of 88.89 wt.-%. The fracture toughness was calculated by combining the tensile tests with the fracture tests, and the results are posted in FIG. 3D. The highest fracture toughness was obtained when the PAAm ratio was 85.71 wt.-%, and the corresponding number is 8696 $J/m^2$.

This huge fracture toughness is remarkable, because PAAm and alginate single networks (SNs) have a fracture toughness in the range of 10 to $10^2$ $J/m^2$. Furthermore, hydrogels which are well known for the high toughness, such as PHEMA-vinyl pyrrolidone-phenethyl methacrylate copolymers have a fracture toughness around $\Gamma=347$ $J/m^2$ (A. P. Jackson, Biomaterials, 1990, 11, 403-407). Even DN proposed by Gong et al, the toughest hydrogel so far, has the fracture toughness in the range of $10^2$ to $10^3$ $J/m^2$ (Q. M. Yu, Y. Tanaka, H. Furukawa, T. Kurokawa, and J. P. Gong, Macromolecules, 2009, 42, 3852-3855).

Temperature Effect

Figures 38A, 38B:
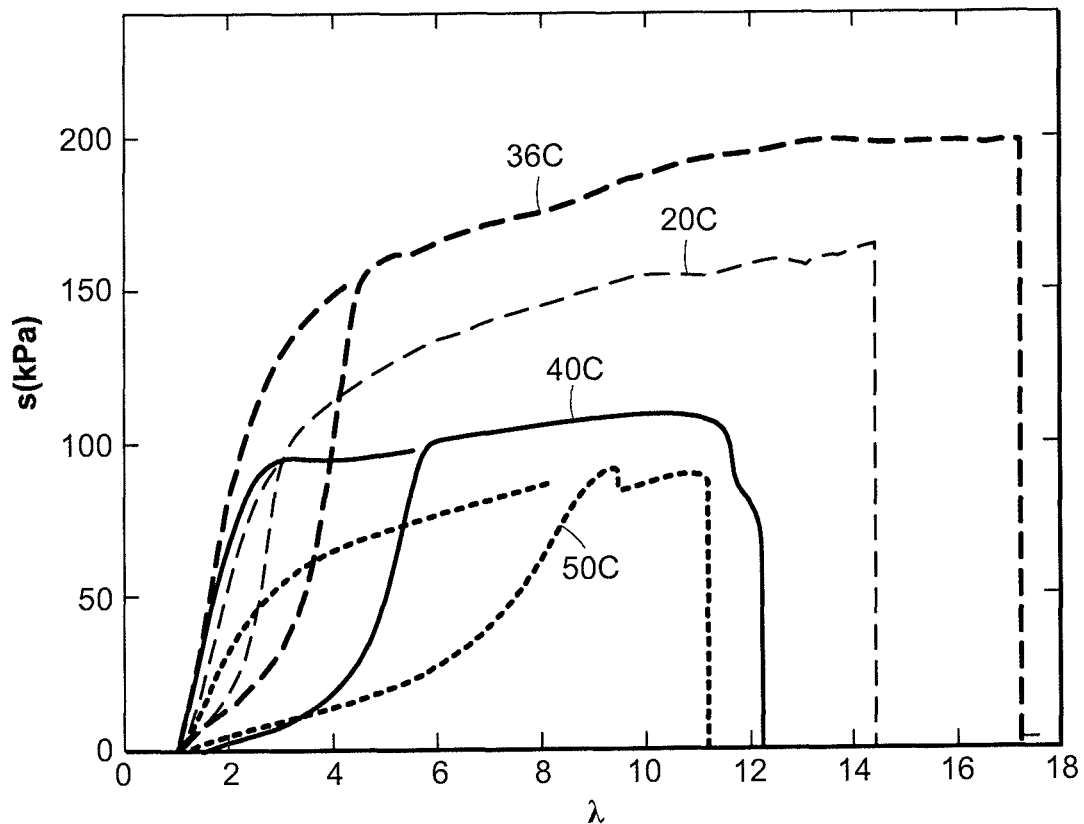
FIG. 38A is a stress-stretch curve for hybrid gels of LF2040 after thermal treatment. Dashed lines indicate the first loading and solid lines indicate an immediate second loading.
FIG. 38B is a chart showing the initial elastic modulus measured at various temperatures.

Thermal treatment affects the properties of the gels by promoting covalent coupling between the two networks (e.g., covalently crosslinked acrylamide network and ionically crosslinked alginate network). Acrylamide-alginate water solutions were prepared as described above. The composition of the gels was as follows: 2 wt % alginate, AAM/alginate=6, MBAA/AAM=30.06%, Ca/alginate=0.1328. For thermal treatment before free radical polymerization, the mixture of alginate and acrylamide was kept at various temperatures for 1 hour. Subsequently, gelation was performed under UV350W for 500 s The stress-stretch curves for hybrid gels of LF2040 after thermal treatment is shown in FIG. 38. As shown in FIGS. 38A and 38B, the properties of the gel greatly depend on the temperature during thermal treatment. Performance (modulus, toughness, and stretchability) improves from 20° C. to 36° C., but deteriorates at higher temperatures.

The alginate chains degrade to shorter chains and unsaturated units during thermal treatment: moderate degradation (<36° C.) creates unsaturated units for better bonds between two networks while not cutting the alginate chains too much. By contrast, severe degradation (>36° C.) results in much shorter alginate chains, deteriorating the gel. Thus, the temperature and duration of thermal treatment can be varied to achieve different mechanical properties and performance of the gel as desired.

FTIR

Spectroscopic analysis was carried out as follows.

Same thickness ($\approx$100 µm) sheets of PAAm-8-0.06 SN gel (water content: 88 wt.-%), Alginate-1-13.28 SN gel (water content: 97 wt.-%), and PAAm-8-0.06/Alginate-1-13.28 copolymer gel (water content: 86 wt.-%) were prepared for Fourier Transform Infrared (FTIR) spectra measurement. Before the measurement, each sample was frozen at −20° C. and dried in vacuum chamber for 2 days to eliminate water molecules from the sample. FTIR spectra were recorded between 4000 and 400 $cm^{-1}$ on a Nicolet 360 FTIR E.S.P. spectrometer. The PAAm/Alginate copolymer hydrogels were characterized by comparing the FTIR spectra with the spectra of parent materials, PAAm and alginate.

Figure 9B:
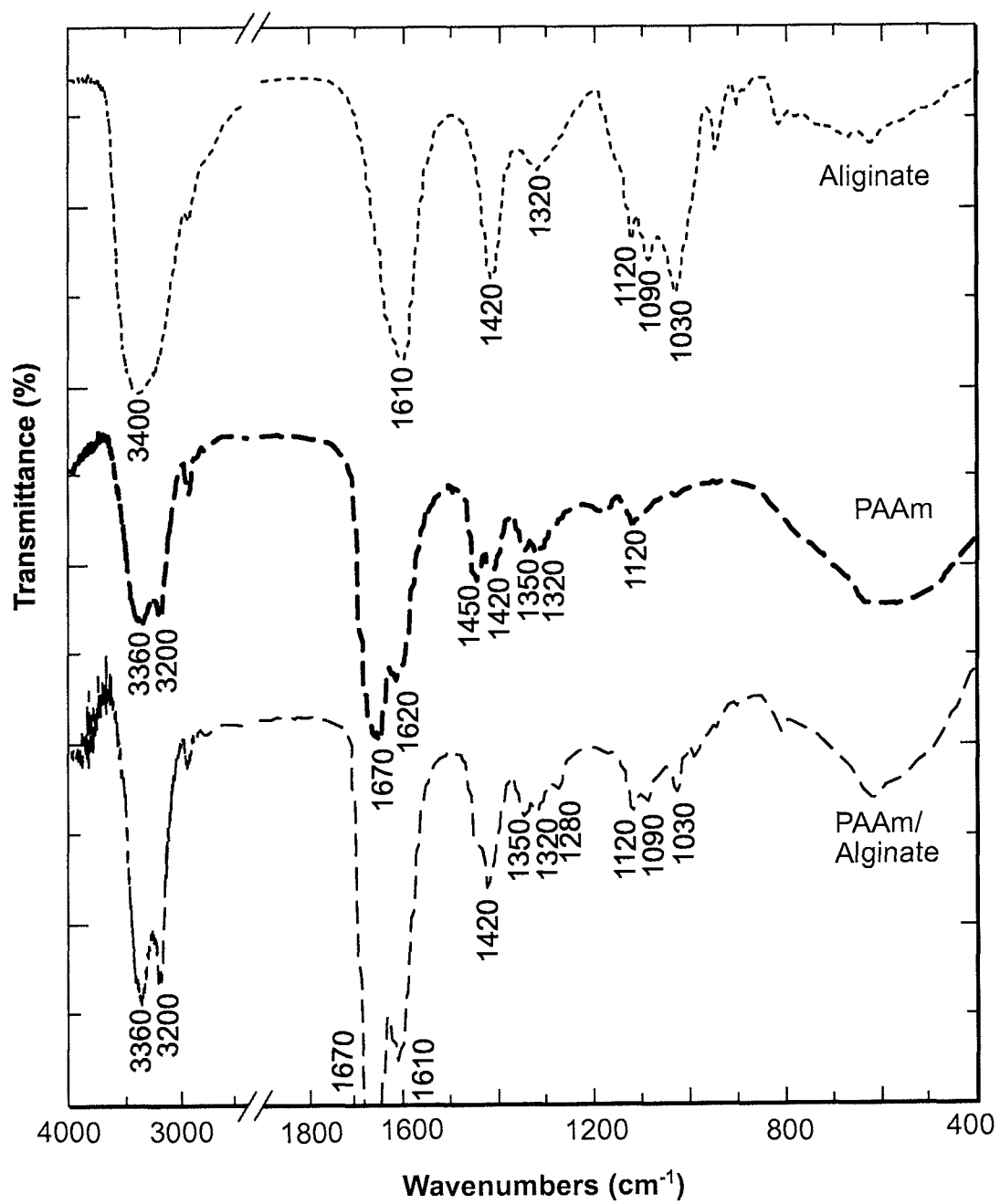

FIG. 9 shows the FTIR spectra of Alginate, PAAm, and PAAm/Alginate copolymer in the wavelength range of 4000-400 $cm^{-1}$. Alginate shows a broad peak near 3400 $cm^{-1}$ for O—H stretching, one sharp peak at 1620 $cm^{-1}$ for asymmetric COO— stretching, two peaks at 1420 and 1320 $cm^{-1}$ for C—H deformation with secondary alcohols, and three peaks at 1120, 1090, and 1030 $cm^{-1}$ for asymmetric C—O—C stretching, C—O stretching in CH—OH structure, and symmetric C—O stretching in C—O—C structure, respectively. The IR spectrum of PAAm exhibiting bands at 3360 $cm^{-1}$ and 3200 $cm^{-1}$ were assigned to a stretching vibration of N—H, and at 1670 $cm^{-1}$ for C=O stretching. The bands at 1620 $cm^{-1}$ (N—H deformation for primary amine), 1450 $cm^{-1}$ ($CH_2$ in-plane scissoring), 1420 $cm^{-1}$ (C—N stretching for primary amide), 1350 $cm^{-1}$ (C—H deformation), and 1120 $cm^{-1}$ ($NH_2$ in-plane rocking) were also detected. The spectra of the PAAm/Alginate copolymer are characterized by comparing the presence of the absorption bands with the pure components. In the spectra of PAAm/Alginate copolymer, new peak at 1280 $cm^{-1}$ for C—N stretching of secondary amide was created. Furthermore, the intensity of the absorption bands (1620, 1420 $cm^{-1}$) which are related with primary amide, and the intensity of $NH_2$ in-plane rocking peak (1120 $cm^{-1}$) are decreased. Moreover, the intensities of O—H stretching peak (3400 $cm^{-1}$), C—O stretching in CH—OH structure (1090 $cm^{-1}$), and symmetric C—O stretching in C—O—C structure (1030 $cm^{-1}$) were decreased. The new bonds form between —$NH_2$ groups of PAAm and —OH groups of alginate.

Cycling of Mechanical Properties: Fracture of $2^{nd}$ Cycle

Figure 10A:
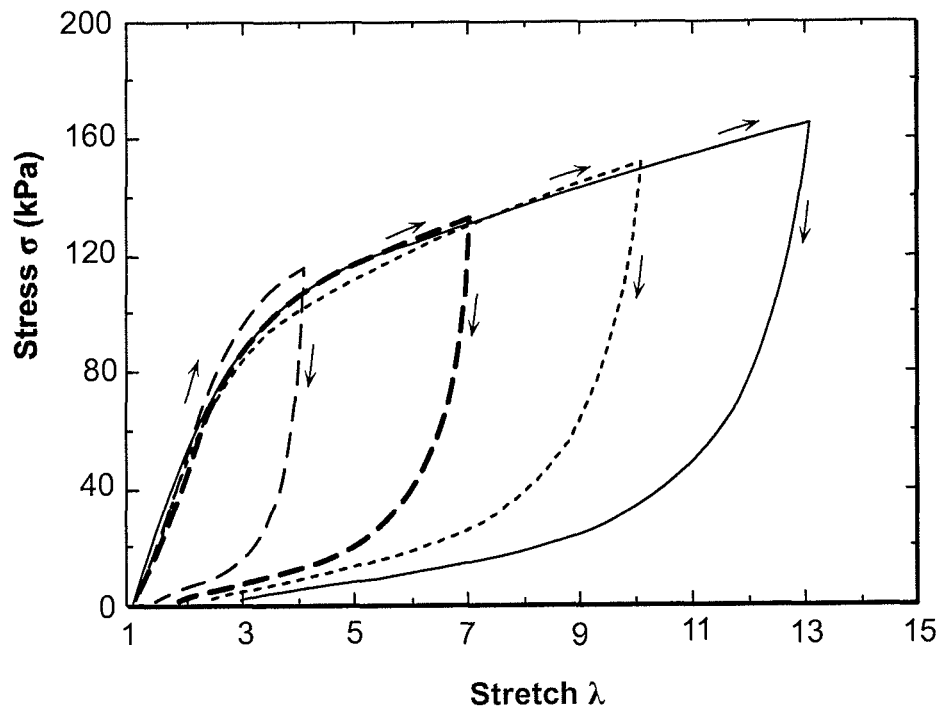
FIGS. 10A-D are a series of graphs showing loading-unloading tensile tests with extremely large stretch, demonstrating highly reversible deformation of PAAm/Alginate IPN gels.
Figure 10B:
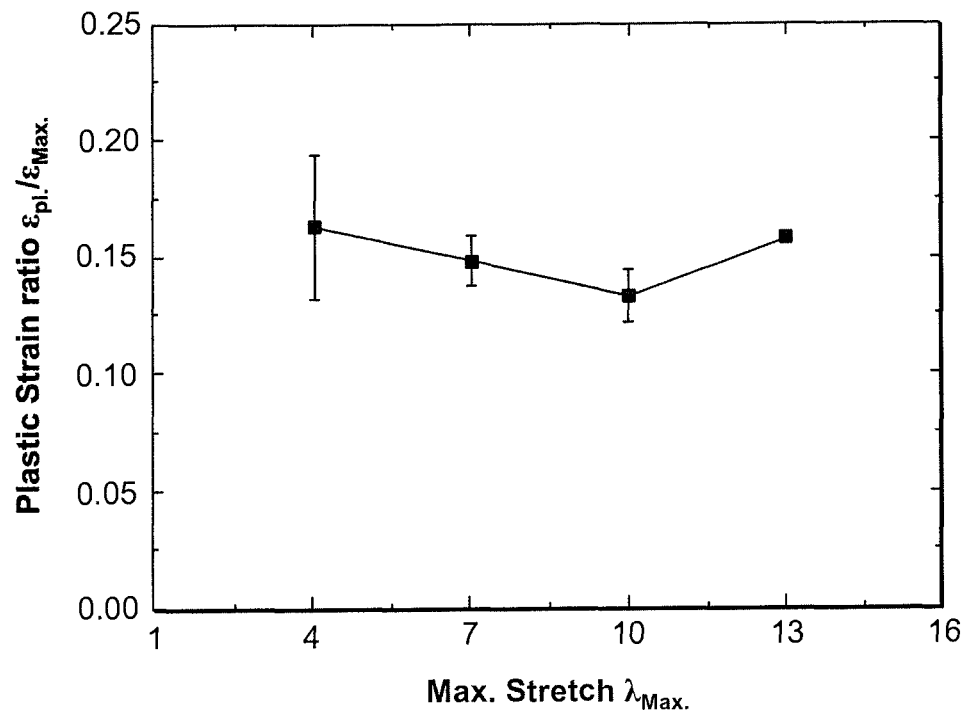
Figure 10C:
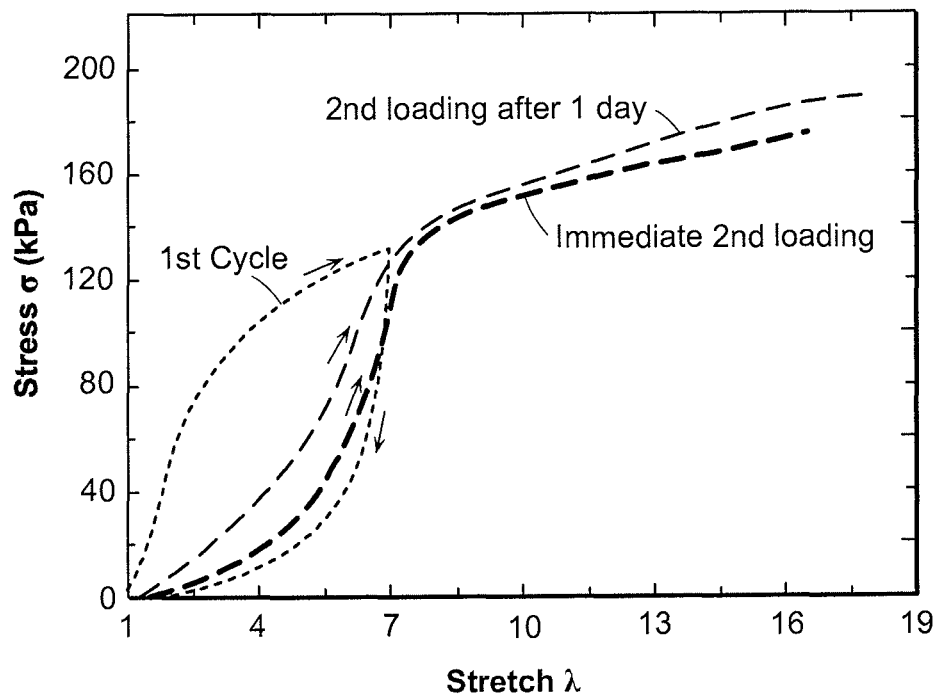
Figure 10D:
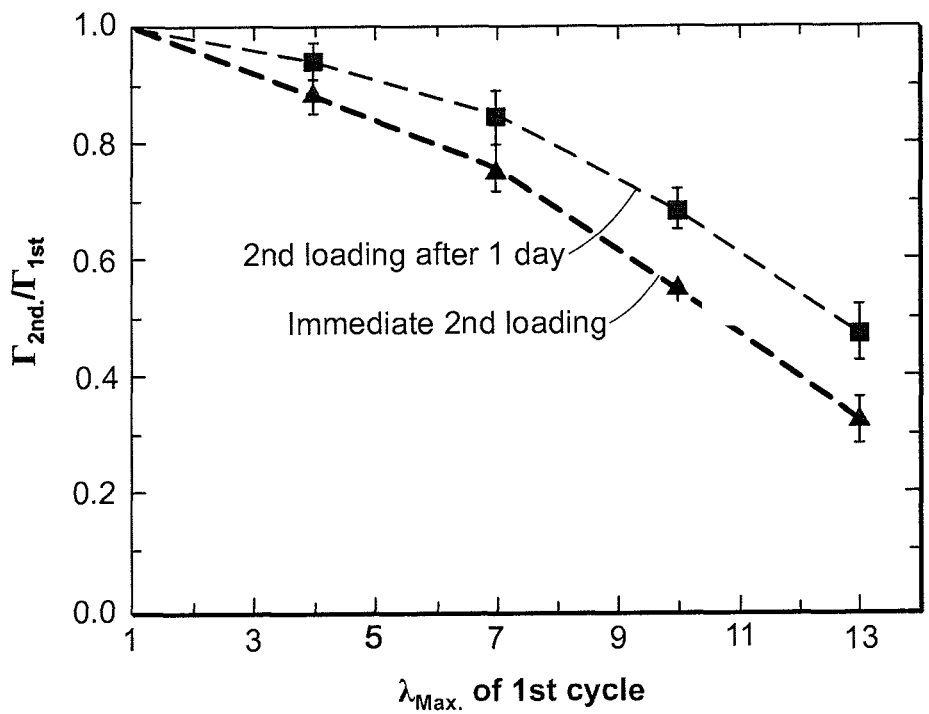

The unique phenomenon of self-healing is depicted in FIG. 10C, D. The repeated tensile tests and fracture tests for $2^{nd}$ loading were carried out with samples which were experienced first loading and unloading without initial crack up to various maximum stretches of first cycle ($\lambda_{max}$). To reveal the recovery property of IPN hydrogel, two sets of samples were prepared. One set was immediately loaded right after $1^{st}$ unloading and the other was subjected to the $2^{nd}$ loading after storing the unloaded sample in a humid box at room temperature for 1 day. An initial edge crack ($c_0$) for fracture test was introduced after unloading of $1^{st}$ cycle by razor blade in lengths of $c_0/L \approx 0.5$.

Ionic crosslinking in alginate gels has previously demonstrated reversible associations that permits gel recovery after shear deformation. So, the distinct advantage of PAAm/alginate IPN gel over covalently crosslinked double network gels could be its potential self-healing ability since double network gels which have no fatigue resistance has the second loading in the same location followed by the unloading behavior of the previous test.

Stress-stretch curves for repeated tensile test of PAAm/alginate IPN gel were plotted in FIG. 10A. $2^{nd}$ loadings were carried out with samples which were experienced first loading and unloading without initial crack, up to the maximum stretches of first cycle ($\lambda_{max}$). To study the recovery of IPN hydrogel, two sets of samples were prepared. One set was immediately loaded right after $1^{st}$ unloading and the other was subjected to the $2^{nd}$ loading after storing the unloaded sample in a humid box at room temperature for 1 day.

The first cycle showed big hysteresis which is caused by plastic deformation of ionic crosslinking of alginate gel. In both cases, IPN gels behave more compliant than $1^{st}$ loading in the second loading when the stretch was below the maximum stretch of the $1^{st}$ cycle. However, IPN gel recovers its stiffness after the maximum stretch of the $1^{st}$ cycle. The stress-strain curves of $2^{nd}$ loading seem to be influenced by the $1^{st}$ cycle only under the maximum stretch region of the first cycle. Moreover, when the stretch was below the maximum stretch of the $1^{st}$ cycle, the sample which was loaded secondly after 1 day shows significant recovery on stiffness compared with immediate $2^{nd}$ loaded sample. Below the maximum stretch of the $1^{st}$ cycle region, the sample which was loaded after 1 day can take 51.2% energy of $1^{st}$ loading, rather than 31.6% energy which was taken by the immediately $2^{nd}$ loaded sample. This energy ratio was not changed much by varying the maximum stretch of the $1^{st}$ cycle.

For the fracture test, an initial edge crack ($c_0$) was introduced after unloading of $1^{st}$ cycle by a razor blade in lengths of $c_0/L \approx 0.5$. The onset crack propagating stretches of $2^{nd}$ loading had almost same range with that of $1^{st}$ loading, and $2^{nd}$ loading after 1 day and immediate $2^{nd}$ loading samples also showed similar critical stretches. The toughness of the second loading was plotted as a function of the maximum stretches of first cycle in FIG. 10B. The toughness ratio of $2^{nd}$ loading to $1^{st}$ loading was decreased as increasing the maximum stretch of $1^{st}$ cycle, because IPN gel becomes softer below the maximum stretch of $1^{st}$ cycle. One remarkable point is, in the immediate $2^{nd}$ loading, PAAm/alginate IPN gel still has 55.2% toughness which is 4803 $J/m^2$ in the second loading even after $\lambda_{max}=10$ stretch. The sample which was loaded secondly after 1 day showed 13.1% additional toughness recovery, compared to immediately loaded sample when the maximum stretch of $1^{st}$ cycle was 10. This toughness ratio became larger as the applied maximum stretch of $1^{st}$ cycle became larger.

IPN Hydrogel Networks with Toughness, Defect Resistance, and Cycling Properties

When the ionically crosslinked alginate networks were added to the PAAm back bone networks, alginate network helps to dissipate the energy with plastic deformation without breaking alginate chain itself. The plastic behavior of ionically crosslinked alginate assist to broaden the plastic zone size and make the PAAm/alginate IPN gel tough. PAAm/alginate IPN hydrogel which has ~90% water content showed a greater enhancement of the mechanical properties, high stretch (around 21) and an order of magnitude increase in fracture toughness (around 9000 $J/m^2$) over the previously described double network hydrogel. Moreover, PAAm/alginate IPN hydrogel also shows high fatigue resistance; 54.6% energy was recovered in $2^{nd}$ loading after storing sample at 80° C. for 1 day.

The Effect of Damage on Reloading

Figure 11:
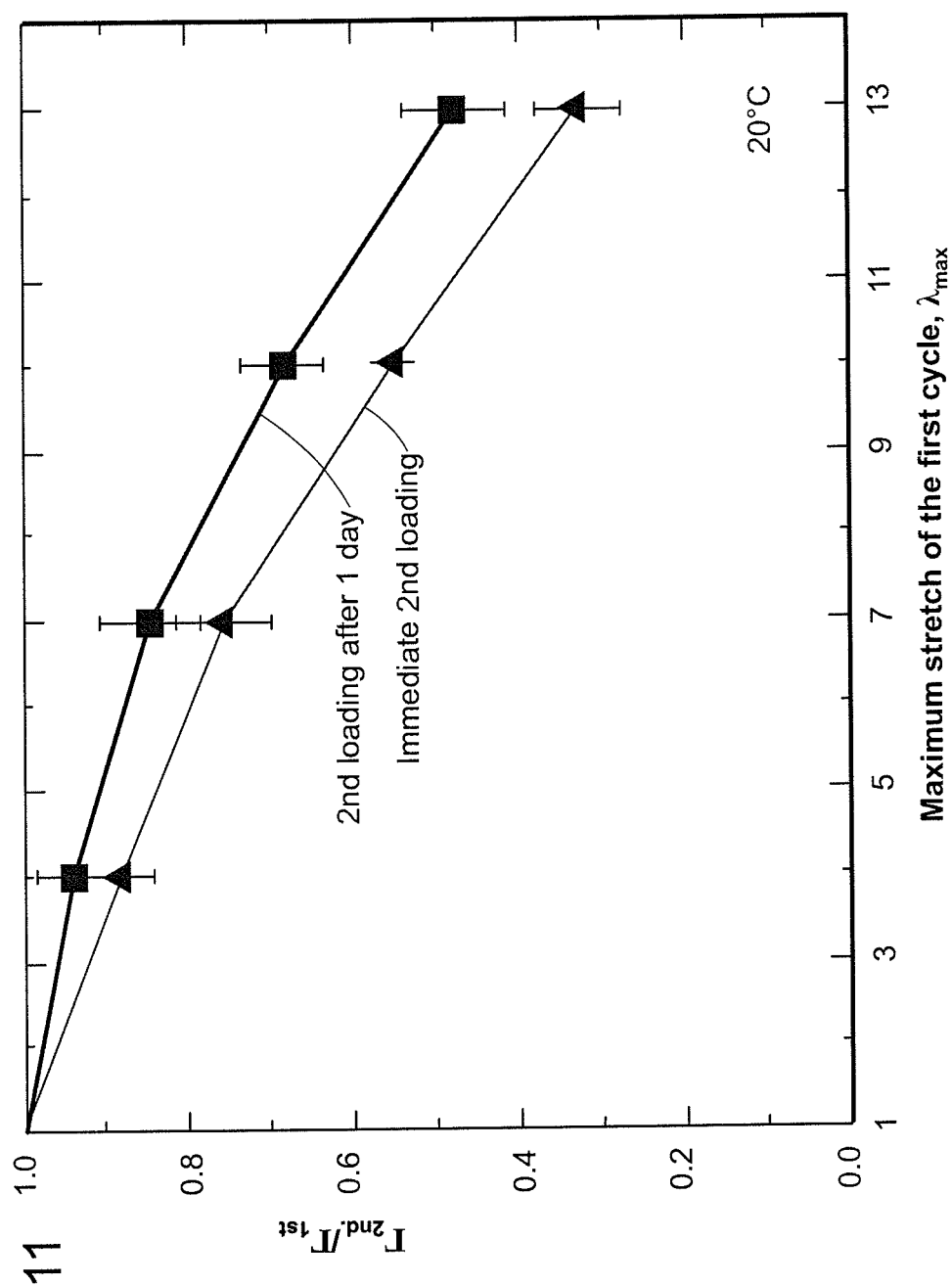
FIG. 11 is a line graph showing damage to the gel after the first cycle. The hybrid gel was first loaded to a certain maximum stretch $\lambda_{max}$, and was then unloaded to zero force, followed by a second loading. The fracture energy determined on the second loading $\Gamma_{2nd}$ was reduced from that determined on the first loading first $\Gamma_{1st}$. The alginate-to-acrylamide ratio was 1:6. The covalent crosslinker, MBAA, was fixed at 0.0006 the weight of acrylamide. The ionic crosslinker, $CaSO_4$, was fixed at 0.1328 the weight of alginate. (Error bars, S.D.; n=3).

The hybrid gel suffers internal damage after the first loading. To study the effect of the damage, a sample of the hybrid gel was loaded up to a certain stretch $\lambda_{max}$, unloaded the gel to zero force, and followed with a second loading. The fracture energy measured on the second loading was reduced from that measured on the first loading (FIG. 11). The amount of reduction increased with the maximum stretch of the first loading. The gel regained some fracture energy if the second loading was applied 1 day later.

Recovery after the First Loading: The Effect of Storage Time and Temperature

Figure 12A:
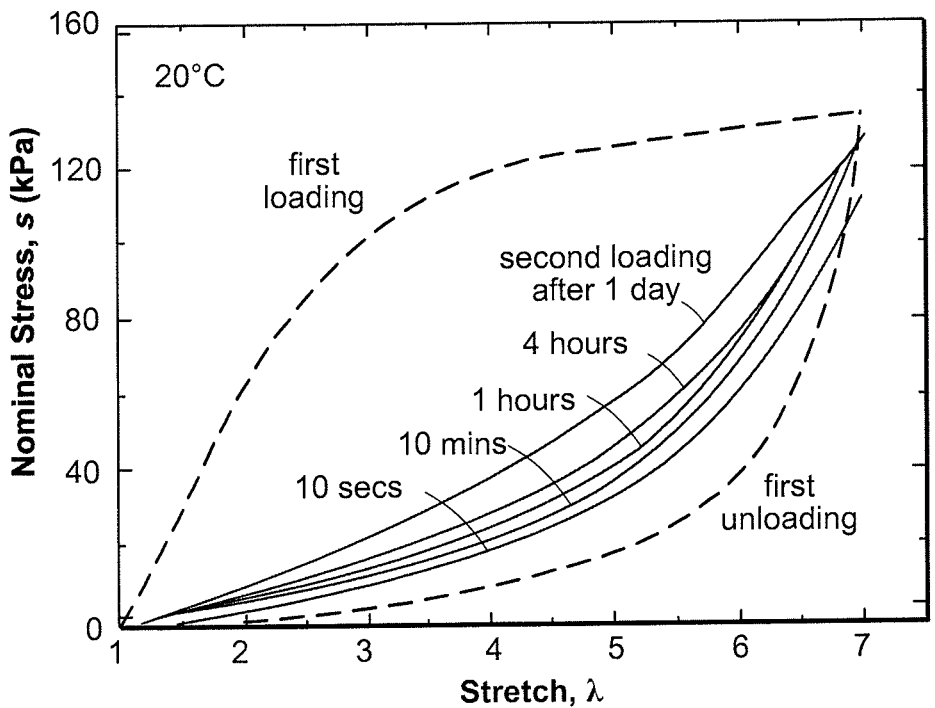
FIGS. 12A and 12B are line graphs showing recovery of the gel after the first loading. Each hybrid gel sample was first loaded to a stretch of $\lambda=7$, and then unloaded. The samples were then stored at a certain temperature for a period time, followed by a second loading at room temperature. Stress-stretch curves are shown for samples stored at: a, 20° C.; b, 60° C. The alginate-to-acrylamide ratio was 1:6. The covalent crosslinker, MBAA, was fixed at 0.0006 the weight of acrylamide. The ionic crosslinker, $CaSO_4$, was fixed at 0.1328 the weight of alginate. Exemplary weight ratios of acrylamide to (acrylamide plus alginate) are from 66.67 wt. % to 94.12 wt. %; exemplary weight ratios of $CaSO_4$/Alginate are from 3.32 wt. % to 53.15 wt. %; and, exemplary weight ratios of N,N-methylenebisacrylamide/acrylamide are from 0.031 wt. % to 0.124 wt. %.
Figure 12B:
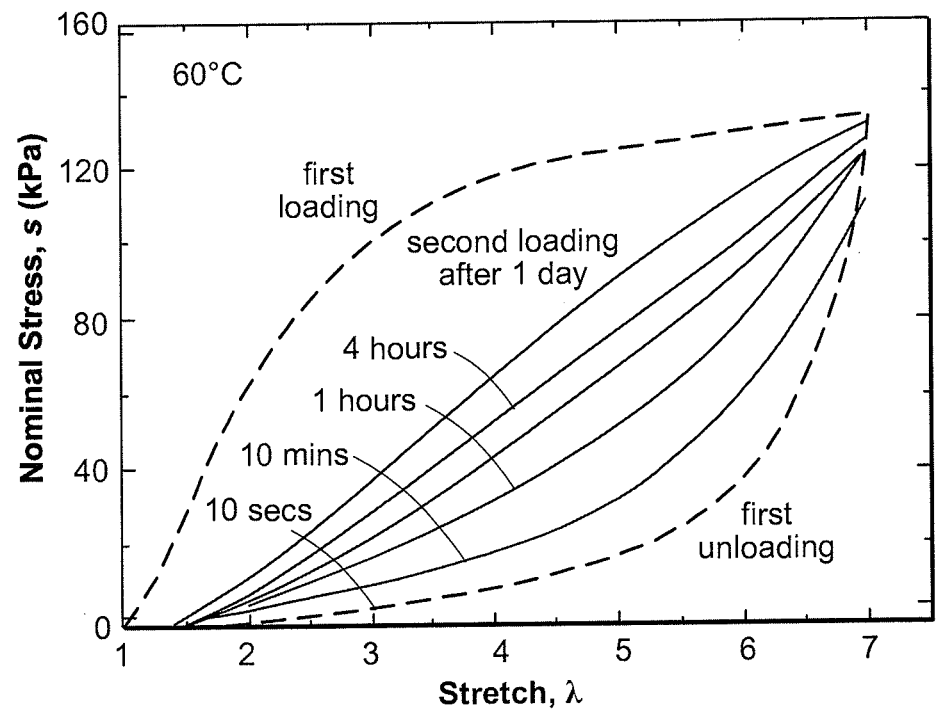
Figure 13A:
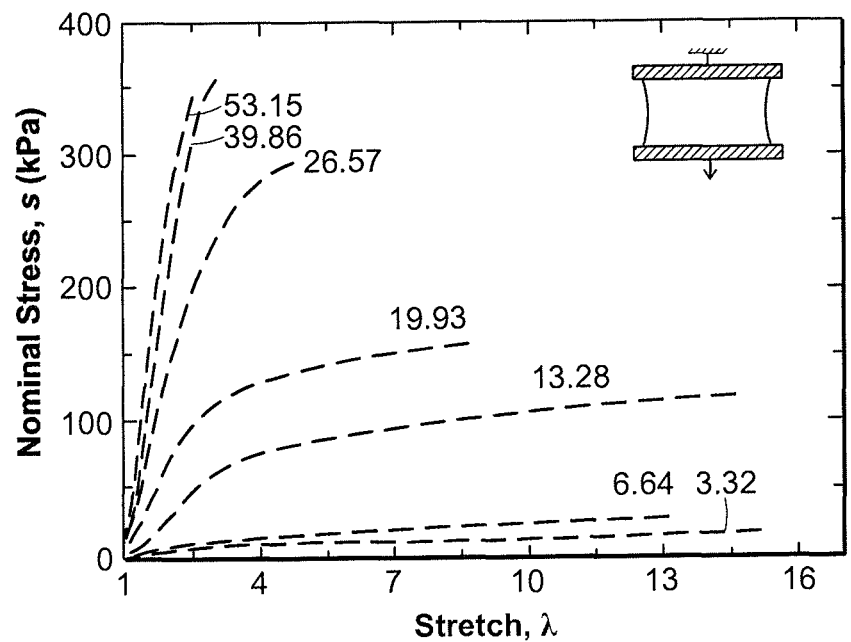
FIGS. 13A-D are line graphs showing that the amount of ionic crosslinker, $CaSO_4$, affects the behavior of the hybrid gel. A, Stress-strain curves were measured using unnotched samples of gels of various values of $CaSO_4$/Alginate (wt %). B, Elastic moduli were determined by the initial slopes of the stress-strain curves. C, The critical stretches were measured using notched samples of gels. D, Fracture energy varies with the density of the ionic crosslinker. The weight ratio of alginate to acrylamide was fixed at 1:10, and the water content was fixed at 86 wt %. The covalent crosslinker, MBAA, was fixed at 0.0006 the weight of acrylamide. (Error bars, S.D.; n=3).
Figure 13B:
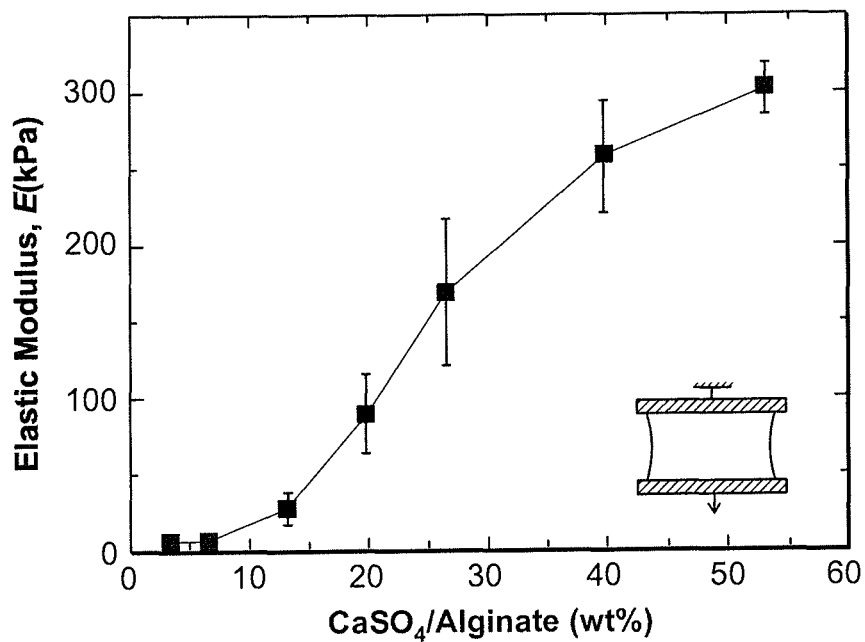
Figure 13C:
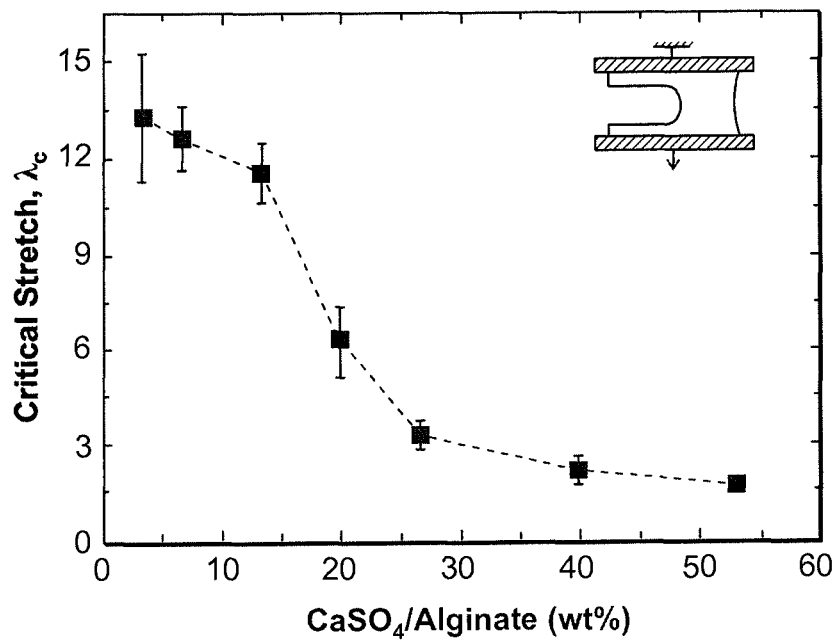
Figure 13D:
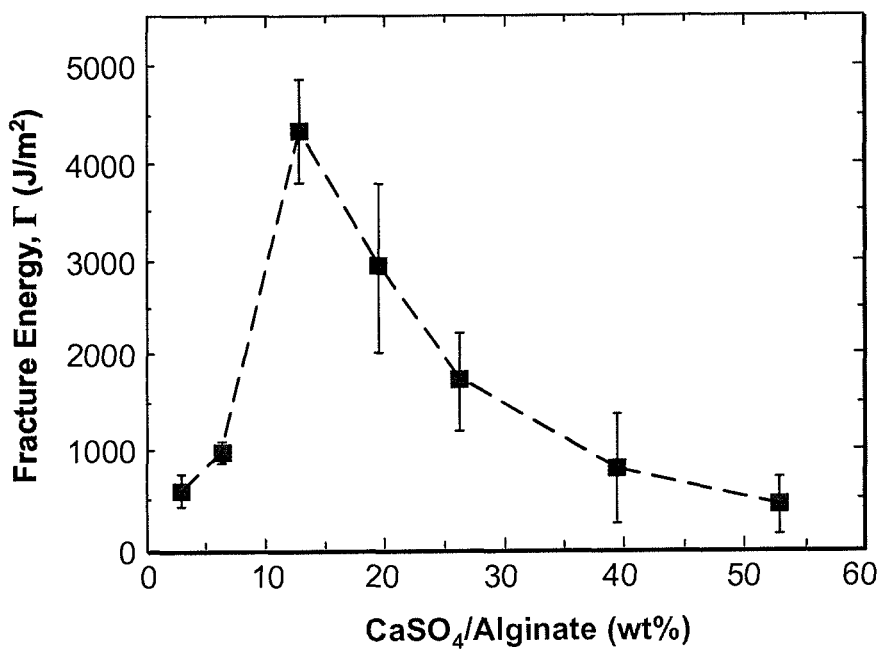
Figure 14A:
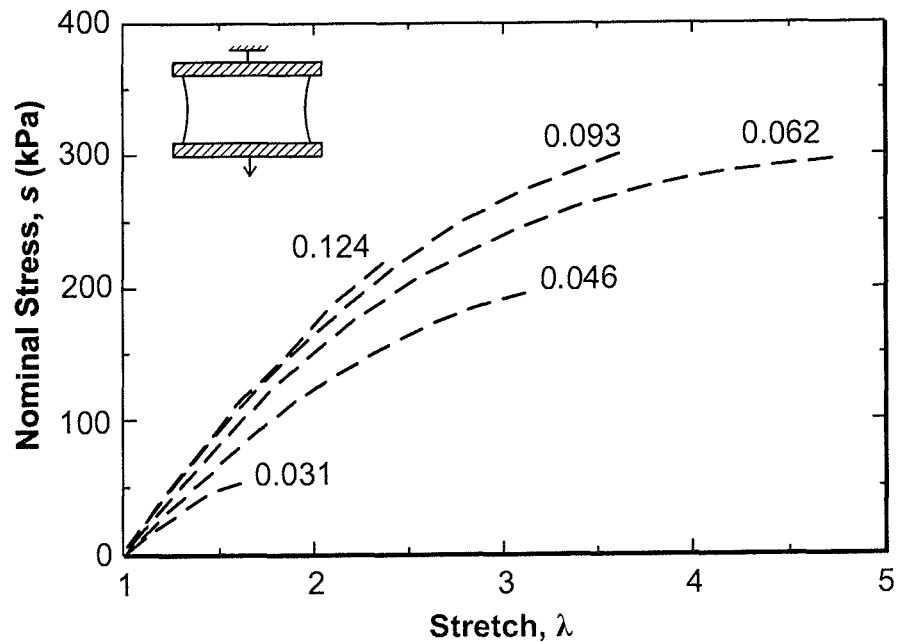
FIGS. 14A-D are line graphs showing that the amount of covalent crosslinker, MBAA, greatly affects the behavior of the hybrid gel. A, Stress-strain curves were measured using unnotched samples of gels of various values of MBAA/Acrylamide (wt %). B, Elastic moduli were determined from the initial slopes of the stress-strain curves. C, The critical stretches were measured using notched samples of gels. D, Fracture energy varies with the concentration of the covalent crosslinker. The weight ratio of alginate to acrylamide was fixed at 1:10, and the water content was fixed at 86 wt %. The ionic crosslinker, $CaSO_4$, was fixed at 0.1328 the weight of alginate. (Error bars, S.D.; n=3).
Figure 14B:
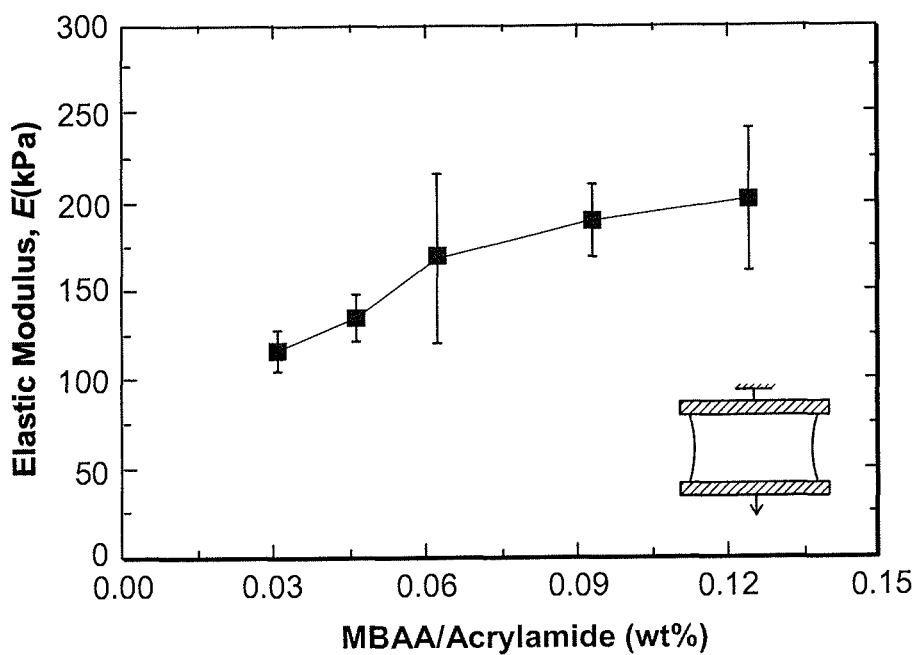
Figure 14C:
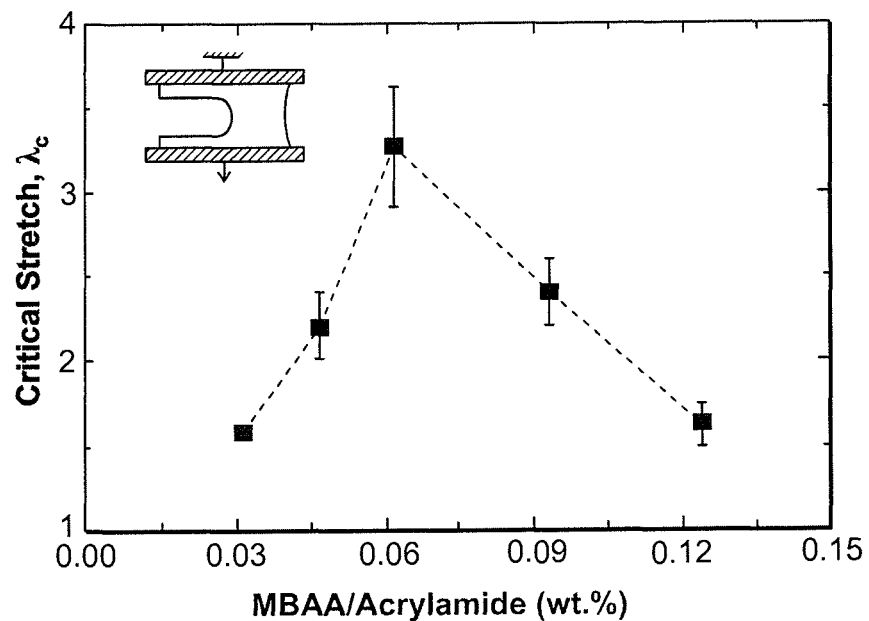
Figure 14D:
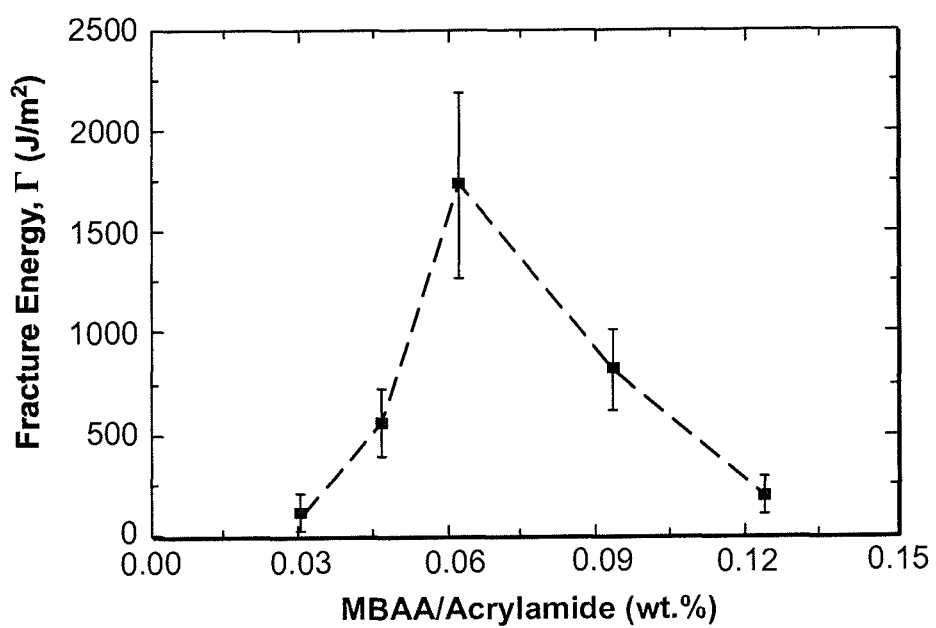
Figure 15A:
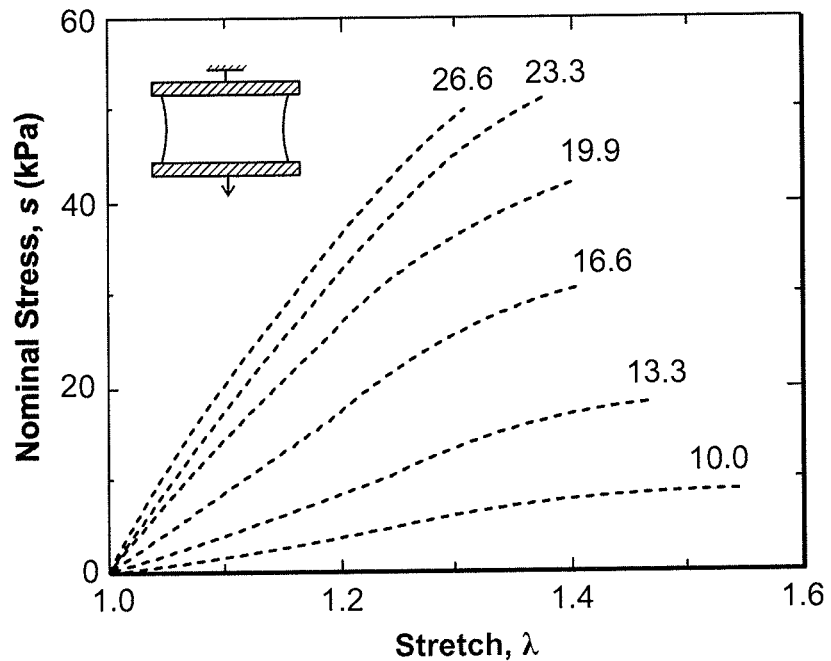
FIGS. 15A-D are line graphs showing the mechanical behavior of alginate hydrogels with various crosslinker densities. A, Stress-strain curves were measured using unnotched samples of gels of various values of $CaSO_4$/Alginate (wt %). B, Elastic moduli were calculated from stress-strain curves. C, The critical stretches were measured using notched samples of gels. D, Fracture energy varies with the density of the ionic crosslinker (Error bars, S.D.; n=3). Water content was fixed at 97 wt. %. (The solubility of alginate in water is less than 4 wt. %.)
Figure 15B:
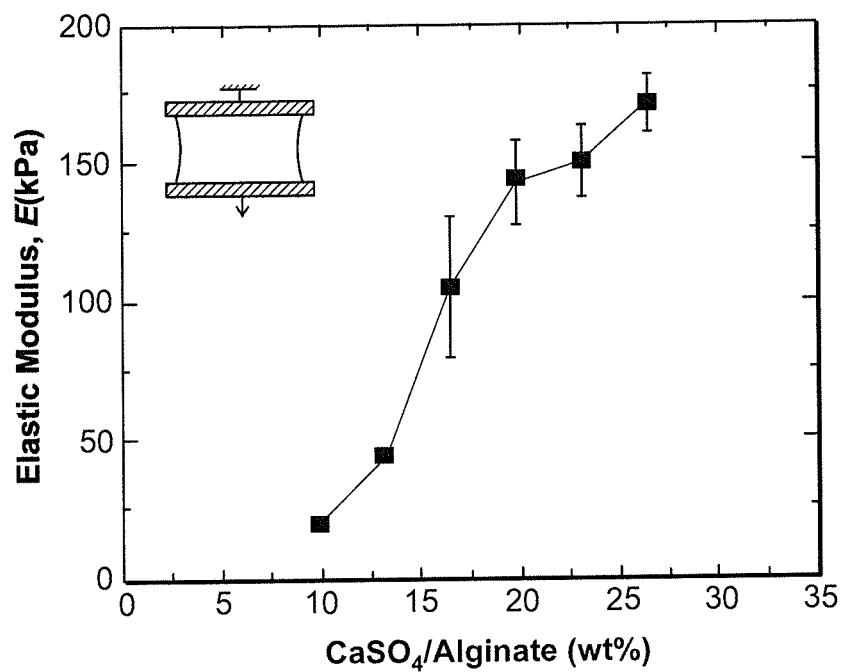
Figure 15C:
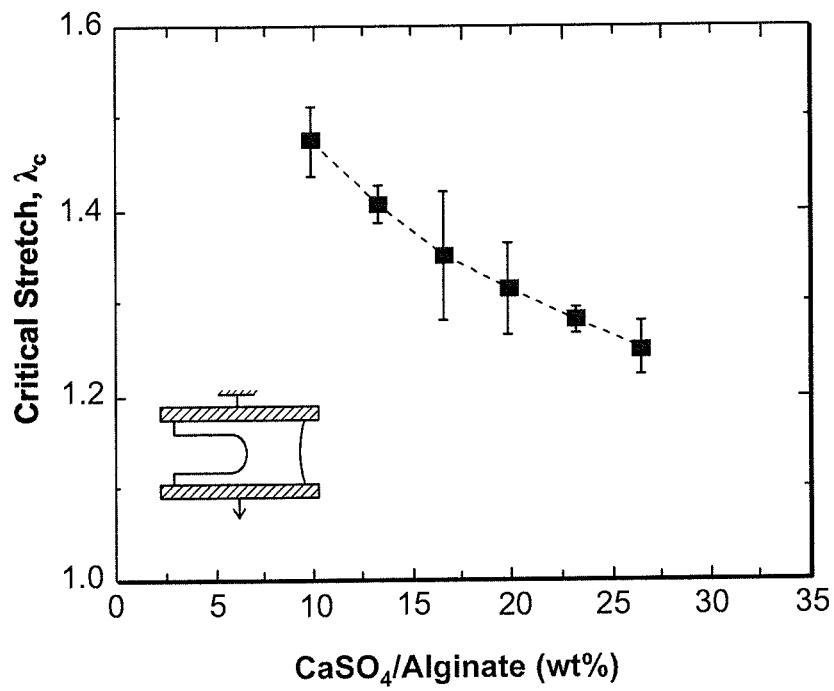
Figure 15D:
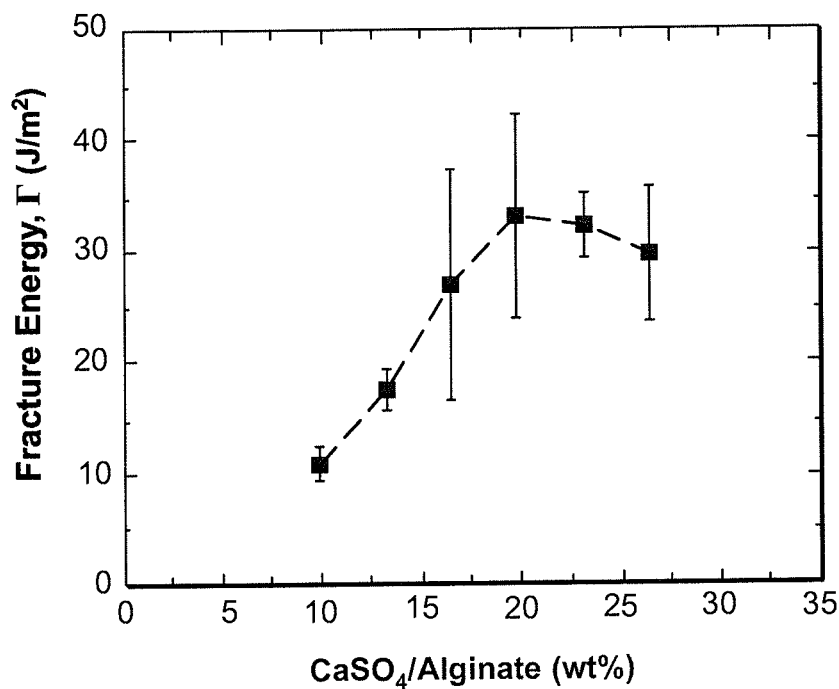
Figure 16A:
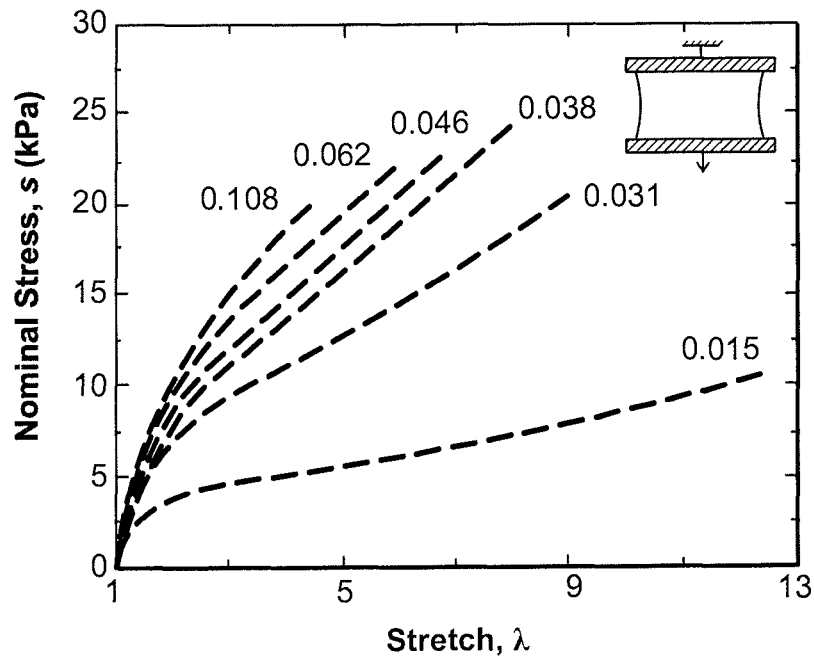
FIGS. 16A-D are line graphs showing the mechanical behavior of polyacrylamide hydrogels with various crosslinker densities. A, Stress-strain curves were measured using unnotched samples of gels of various values of MBAA/Acrylamide (wt %). B, Elastic moduli were calculated from stress-strain curves. C, The critical stretches were measured using notched samples of gels. D, Fracture energy varies with the concentration of the covalent crosslinker. Water content was fixed at 86.4 wt. %. (Error bars, S.D.; n=3).
Figure 16B:
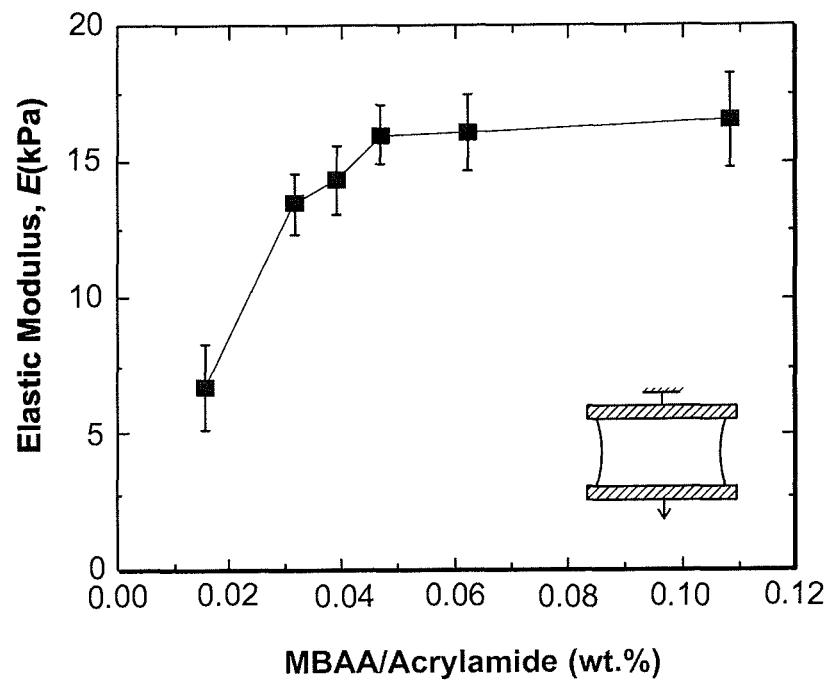
Figure 16C:
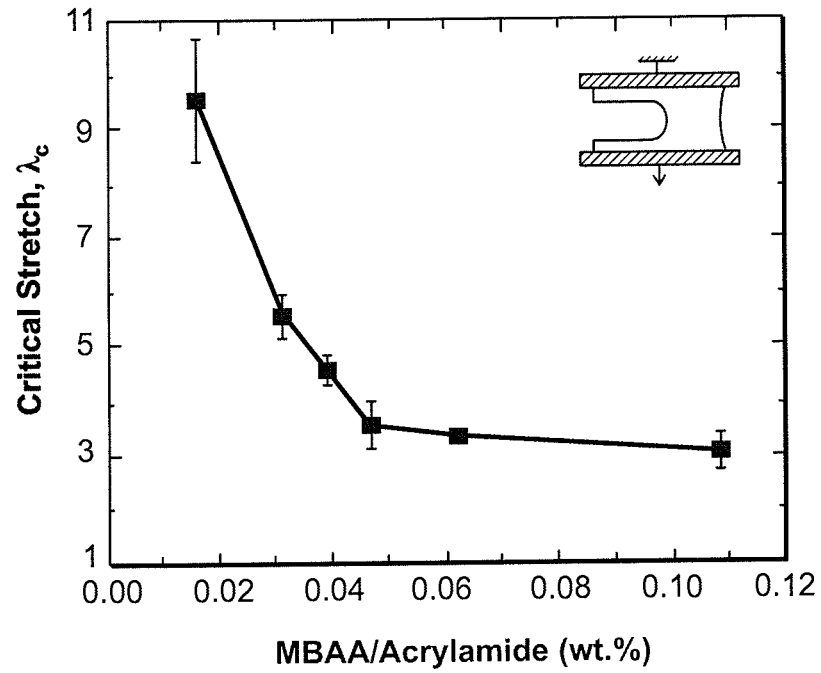
Figure 16D:
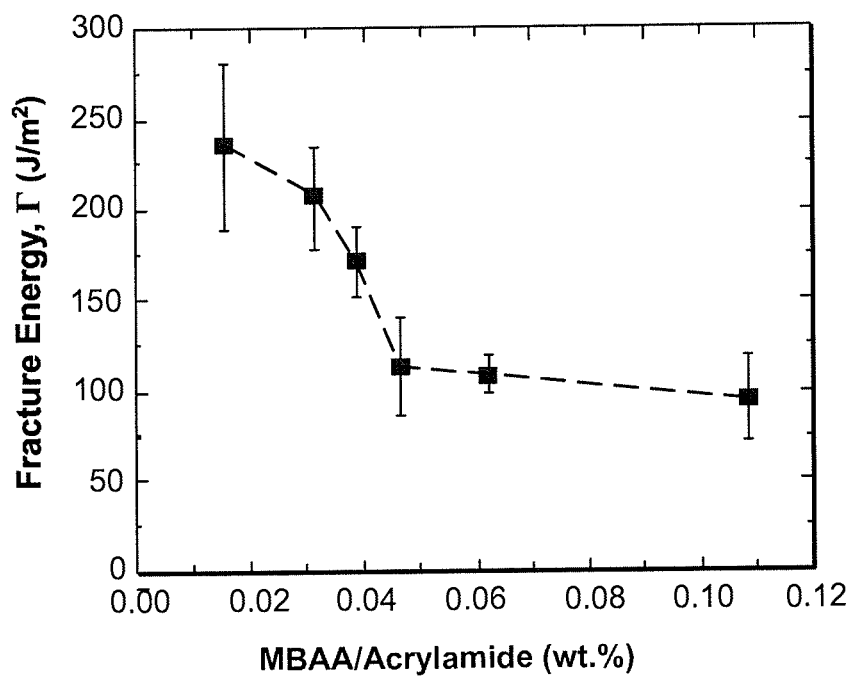
Figure 17A:
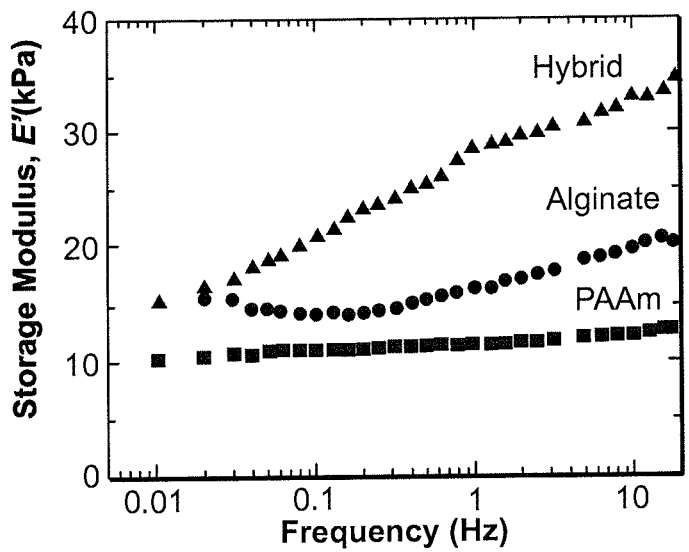
FIGS. 17A-C are dot plots showing viscoelasticity of alginate, polyacrylamide, and hybrid gels. A, Storage modulus E'. B, Loss modulus E". C, The ratio between E" and E'.
Figure 17B:
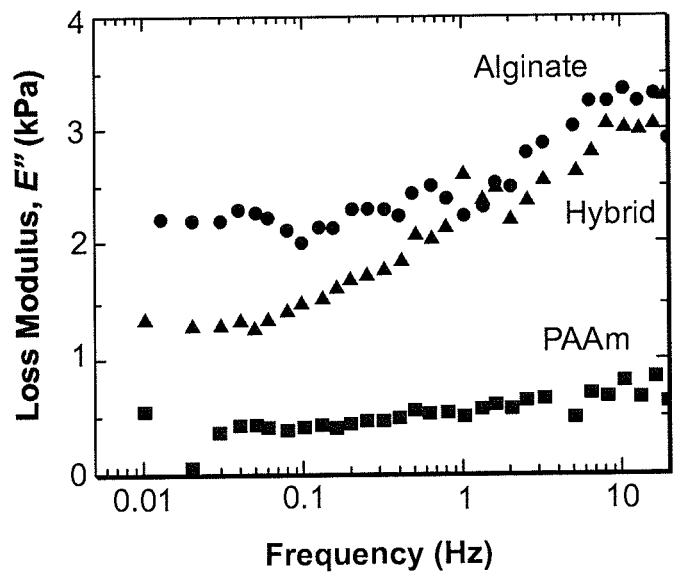
Figure 17C:
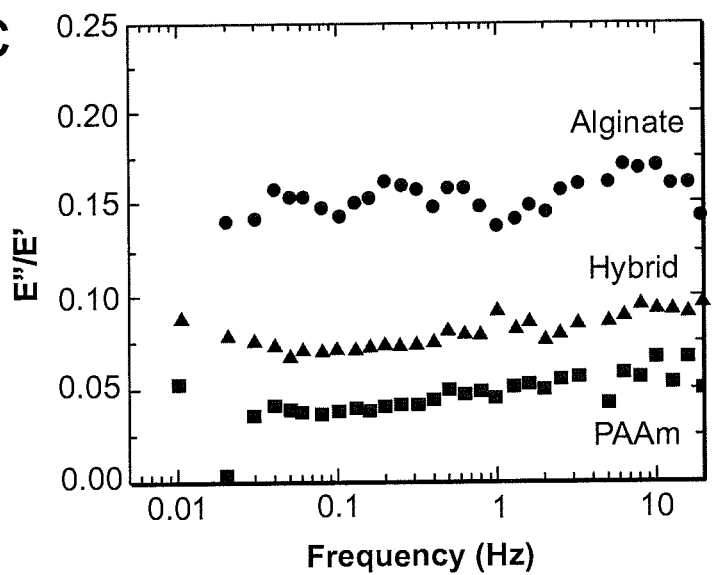

The recovery after the first loading takes time, and can be made faster by storing the gel in a hot bath. A sample of the hybrid gel was first loaded in tension to a stretch of 7, and was unloaded to zero force. The sample was then sealed in a polyethylene bag and submerged in mineral oil to prevent water from evaporation, and stored in a bath of a fixed temperature for a certain period of time. Afterwards, the sample was taken out of storage and its stress-stretch curve was measured again at room temperature. FIGS. 12A-B show the stress-stretch curve on the first loading and unloading, as well as the stress-stretch curves on the second loading after the sample was stored at certain temperatures for certain periods of time. In the second loading, the gel was weaker than the first loading. The extent of recovery increased with the temperature and time of storage.

Effect of the Ionic Crosslink Density of Alginate

To study the effect of the ionic crosslinks between alginate chains, hybrid gels were prepared with various concentrations of $CaSO_4$ (FIGS. 13A-D). For the unnotched samples, the stress needed to deform the gel increased with the concentration of $CaSO_4$. The small-strain elastic modulus increased with the concentration of $CaSO_4$. For the notched samples, however, the critical stretch for the notch to turn into a running crack decreased as the concentration of $CaSO_4$ increased. The highest fracture energy was obtained for an intermediate concentration of $CaSO_4$. These trends are understood as follows. In the absence of $Ca^{++}$, alginate chains are not crosslinked, and bear no load, so that the hybrid gel exhibits a stress-stretch curve indistinguishable from that of the polyacrylamide gel, with large stretchability but low fracture energy. At a high concentration of $Ca^{++}$, alginate chains are densely crosslinked. Only a small zone around the root of the notch is stressed enough to break the alginate chains, so the fracture energy is low.

Effect of the Covalent Crosslink Density of Polyacrylamide

To study the effect of the covalent crosslinks of polyacrylamide, hybrid gels were prepared with various concentrations of the crosslinker MBAA. Properties of these gels are shown in FIGS. 14A-D. As the concentration of MBAA increased, the crosslink density of the polyacrylamide network increased. However, the stiffness of the hybrid gel increased only slightly. The concentration of MBAA did greatly affect the critical stretches of the notched samples. The highest fracture energy was obtained for an intermediate concentration of MBAA. This trend is understood as follows. When the covalent crosslink density is too high, each individual polyacrylamide chain between two crosslinks is short. When the chain breaks, the energy stored in the entire chain is dissipated. Consequently, shorter chains will lead to low fracture energy. In the other extreme, when the covalent crosslink density is too low, the polyacrylamide network becomes too compliant, incapable to stabilize the deformation of the gel. Consequently, deformation in a notched gel is localized: only a small part of the alginate network will unzip and dissipate energy.

The Effect of the Crosslinker Density on Alginate Hydrogels

Mechanical properties were measured for alginate hydrogels of various CaSO4 concentrations (FIGS. 15A-D). For the unnotched samples, the stress needed to deform the gel increased with the concentration of $CaSO_4$. For the notched samples, however, the critical stretch for the notch to turn into a running crack decreased as the concentration of $CaSO_4$ increased. The highest fracture energy was obtained for an intermediate concentration of $CaSO_4$.

The Effect of Crosslinker Density on Polyacrylamide Hydrogels

Mechanical properties were measured for the polyacrylamide hydrogels of various MBAA concentrations (FIGS. 16A-D). As the concentration of MBAA increased, the stiffness of the hybrid gel increased. However, the critical stretch of the notched samples decreased dramatically, the highest fracture energy was obtained for the minimum concentration of MBAA. Polyacrylamide single network gels with smaller than 0.015 wt. % MBAA concentration were only a viscous liquid after crosslinking.

Viscoelastic Responses Determined by Dynamic Mechanical Analysis (DMA)

The viscoelastic responses of alginate, polyacrylamide, and alginate-polyacrylamide hybrid gels were determined by using DMA Q800 (TA Instruments). Compression frequency-sweep tests at 0.1% strain were carried out over the frequency range 0.01-30 Hz. Alginate gels with 97%, polyacrylamide gels with 86.4 wt. %, and alginate-polyacrylamide hybrid gels with 86.4 wt. % water concentration were used for this test. The polymer ratio of alginate-polyacrylamide hybrid gel is 1:6 of alginate to acrylamide. The covalent crosslinker, MBAA, was fixed at 0.0006 the weight of acrylamide for polyacrylamide gel and hybrid gel. The ionic crosslinker, $CaSO_4$, was fixed at 0.1328 the weight of alginate for alginate gel and hybrid gel.

Figure 7A:
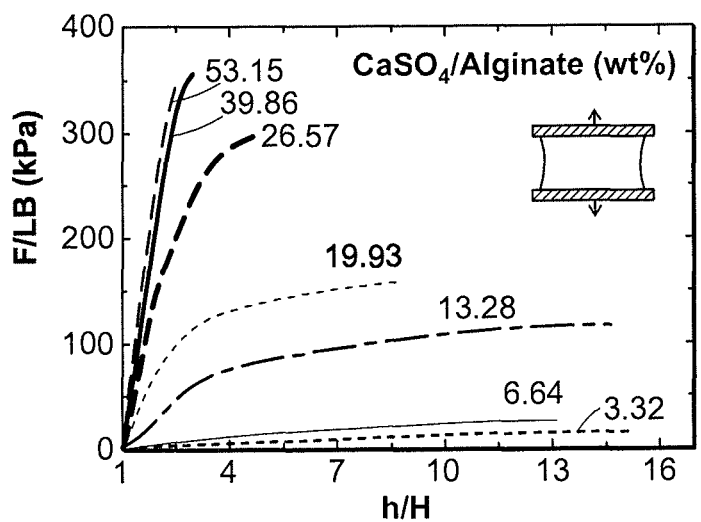
FIGS. 7A-C are a series of line graphs.
Figure 7B:
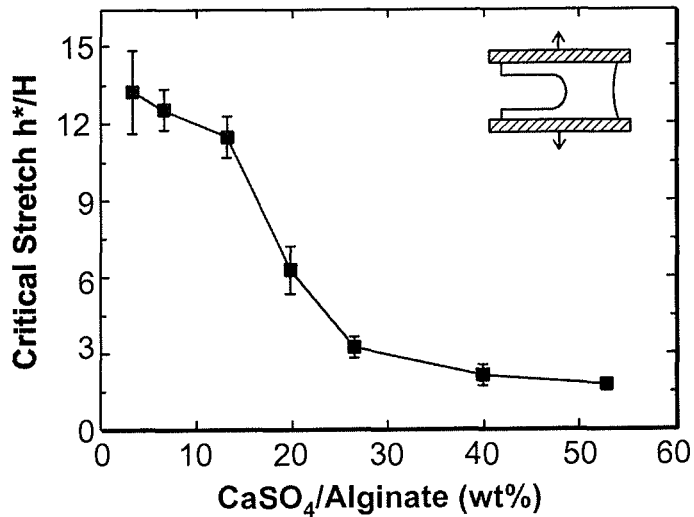
Figure 7C:
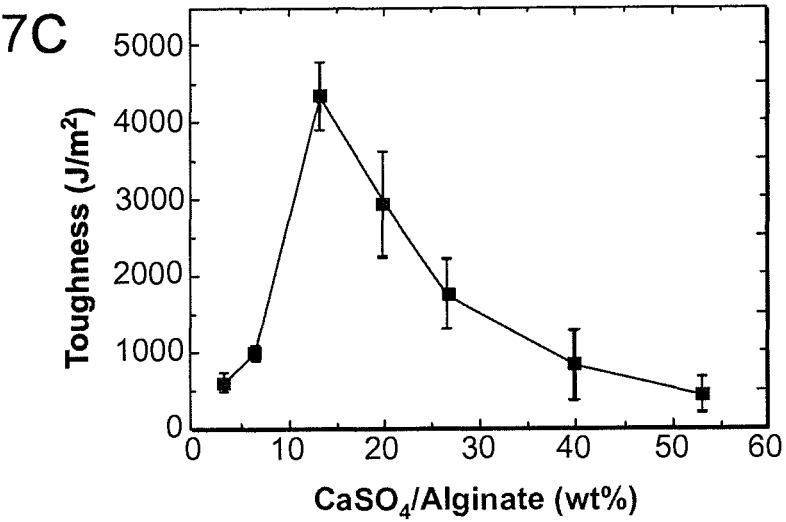

The storage modulus E' and the loss modulus E" for alginate, polyacrylamide, and hybrid gels were determined as the frequency changes (FIGS. 7A-C). The ratio of E"/E' indicates the viscosity of the material. As expected, due to the unzipping behavior of the alginate network, alginate and hybrid gels show more viscous behavior than the polyacrylamide gels. Furthermore, alginate gels and alginate-polyacrylamide hybrid gels clearly show the increase of E" at high frequency. The high frequency rise in E" reflects fast relaxation processes and is typical viscous behavior of gels formed by temporary (breakable) junction zones.

Homogeneity of Hybrid Gels

Figure 18B:
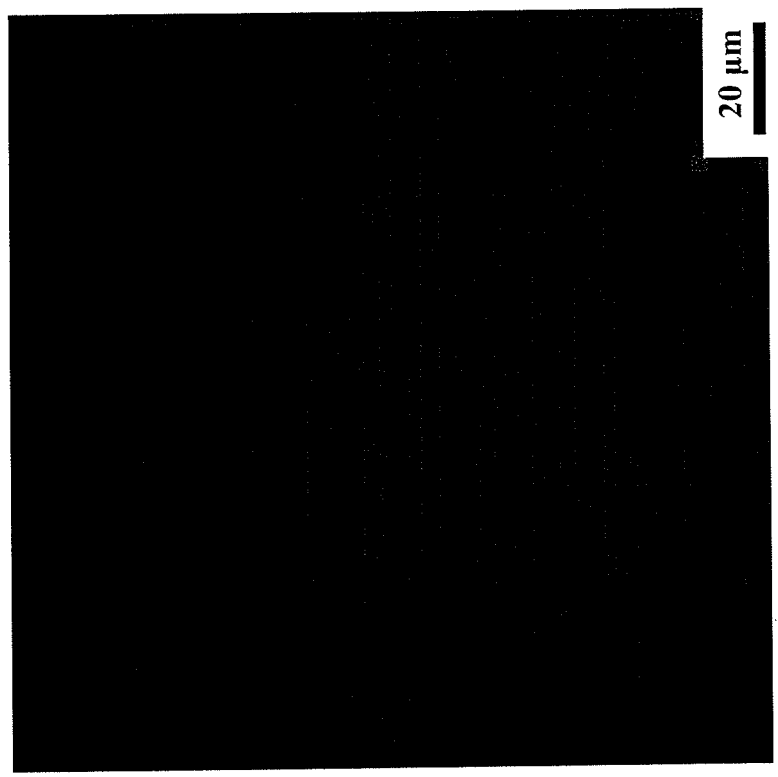
FIGS. 18A-B are photomicrographs.
Figure 18A:
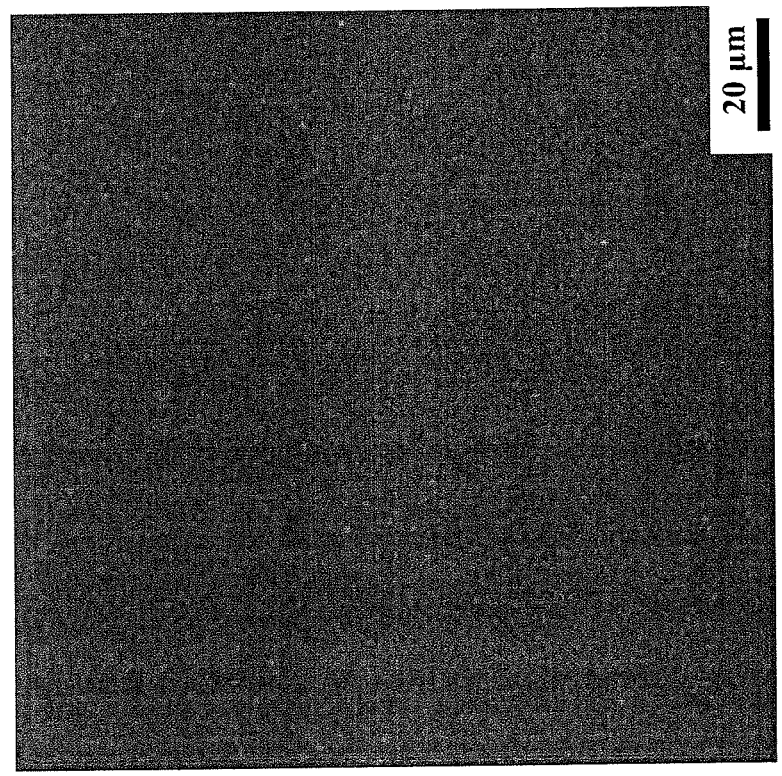
Figure 18D:
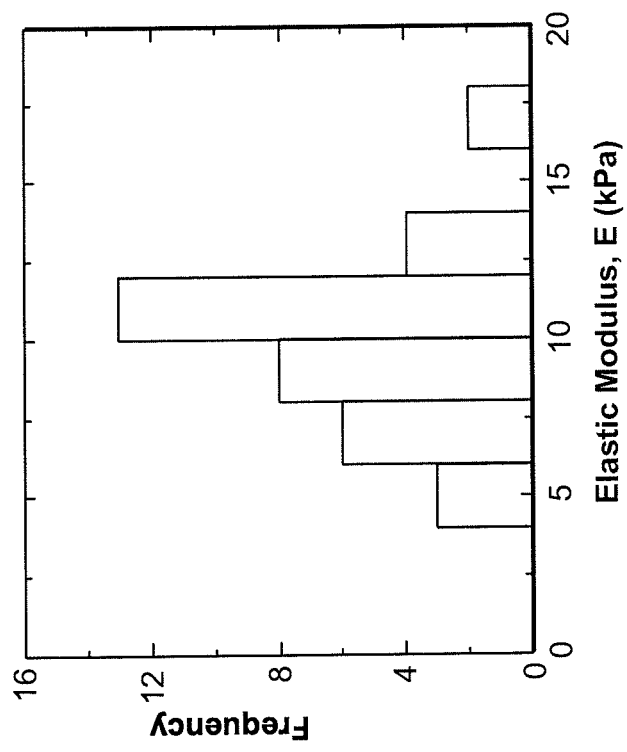
FIG. 18D is a bar graph, which collectively show the homogeneity of hybrid gel. Fluorescence microscopy of hybrid gel mixed with fluorescent alginate (A; fluoresces green, appears grey in the image) and without fluorescent alginate (B; appears dark in the image). C, Elastic modulus map of hybrid gel. D, Statistical plot of elastic modulus.

The homogeneity of alginate-polyacrylamide hybrid gels was investigated in two ways. First, the homogeneity of alginate networks in hybrid gels were tested using fluorescence images of hybrid gels which were fabricated from fluorescent alginate. Second, since the amount of calcium ion was strongly related to the elastic modulus of hybrid gels, the homogeneity of the calcium ions was explored by performing elastic modulus mapping of the surface of the hybrid gel. Alginate-polyacrylamide hybrid gels with 1:6 polymer ratio, 0.0006 MBAA concentration, 0.1328 $CaSO_4$ concentration, and 86.4 wt. % water concentration were used for these tests. Fluorescent alginate was prepared by coupling aminofluorescein (Sigma) to alginate polymers. Fluorescence images were taken using a 1.40 NA 63X PlanApo oil immersion objective on a laser scanning confocal microscope (Zeiss LSM710). As demonstrated by a representative image (FIG. 18A), the fluorescent alginate (fluoresces green; appears grey in the figure) is fully interpenetrating and uniformly distributed within the hybrid gel. The interpenetrating networks hydrogel was found to be homogeneous through whole sample from micron size to millimeter size. Homogeneity refers to the uniform distribution of polymer chains and crosslinkers. Alternatively, the gels are not homogeneous. In the latter case, mechanical performance is altered or tuned to desired characteristics by manufacturing the gel with a gradient in the concentration of polymer and/or crosslinker density. The extent or density of cross-linking is varied as desired to achieve different performance capabilities.

Figure 18C:
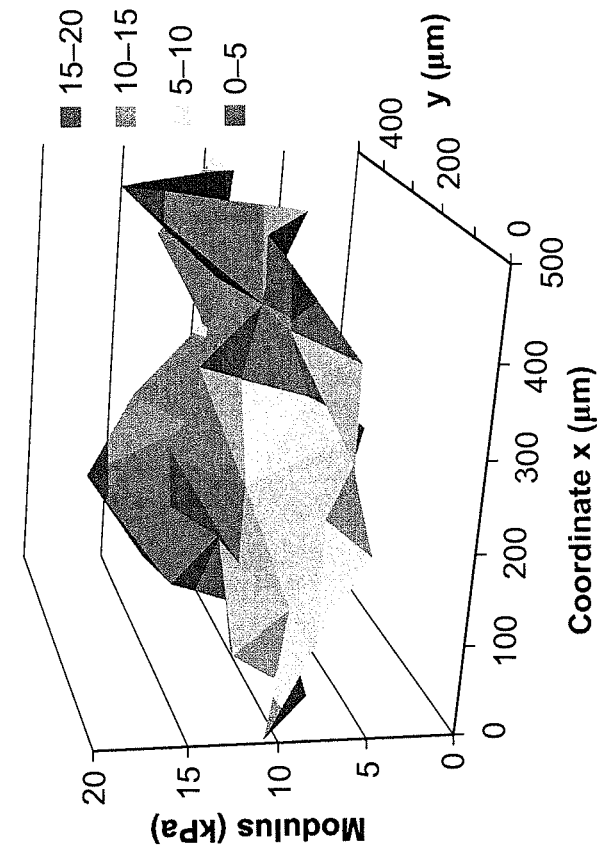
FIG. 18C is a three-dimensional graph.

The elastic modulus mapping was performed using atomic force microscope (Asylum-1 MFP-3D AFM System) with silicon nitride cantilever (Bruker AFM probes) with pyramid tipped probes. The stiffness of cantilevers is calibrated from thermal fluctuations (~35 pN/nm). To reduce the effect of the surface tension of the hydrogel, force measurements were performed in water with a 1000 nm/s sample surface movement. A 500 imX500 im surface area of the hybrid gel is scanned and 6×6 points are examined with a 100 im distance between each point. The elastic moduli were calculated from the relationship between indentation depth 6 and punch load F using the Hertzian model for a pyramid punch. The resulting elastic moduli of hybrid gels and their distribution are plotted in FIGS. 18C and D, respectively. An average 10.0 kPa elastic modulus was obtained with 2.7 kPa standard deviation.

Crosslinks Between Alginate and Polyacrylamide

As mentioned above, the stress-stretch curves of the hybrid gels indicate that both alginate and polyacrylamide bear loads. The mechanism of load-transfer between the two types of polymers is unclear. To investigate possible cross-links between the two types of polymers, the Fourier Transform Infrared (FTIR) spectra of the alginate gel, polyacrylamide gel, and hybrid gel was analyzed. Samples of the same thickness (≈100 μm) were prepared for the alginate gel, the polyacrylamide gel, and the alginate-acrylamide hybrid gel. They were frozen at −20° C. and dried in vacuum chamber for 2 days to eliminate water molecules from the samples. FTIR spectra were recorded between 4000 and 400 $cm^{-1}$ on a Nicolet 360 FTIR E.S.P. spectrometer.

Figure 19A:
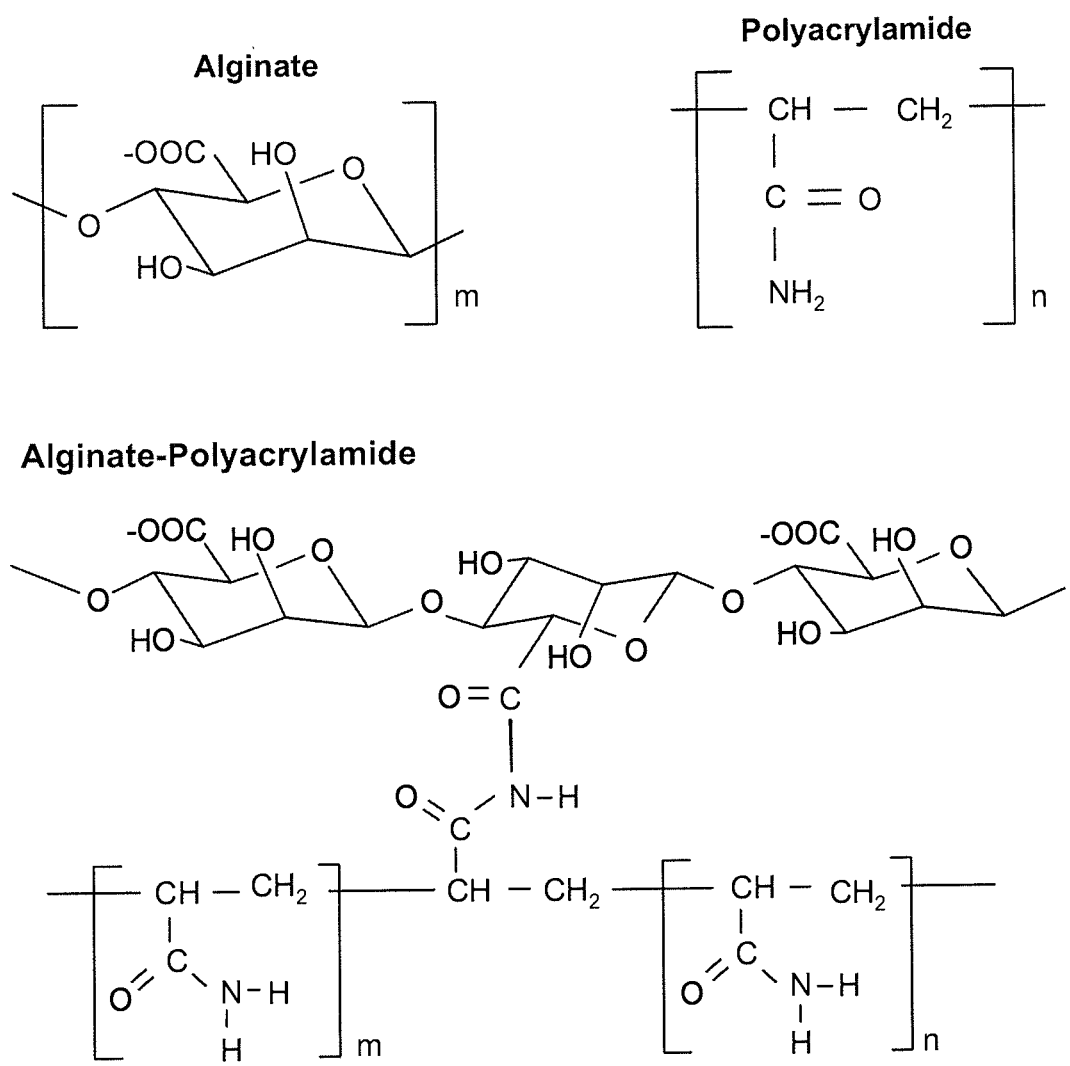
FIG. 19A is a series of chemical structures of alginate and polyacrylamide, and suggested crosslinks between alginate and polyacrylamide.
Figure 19B:
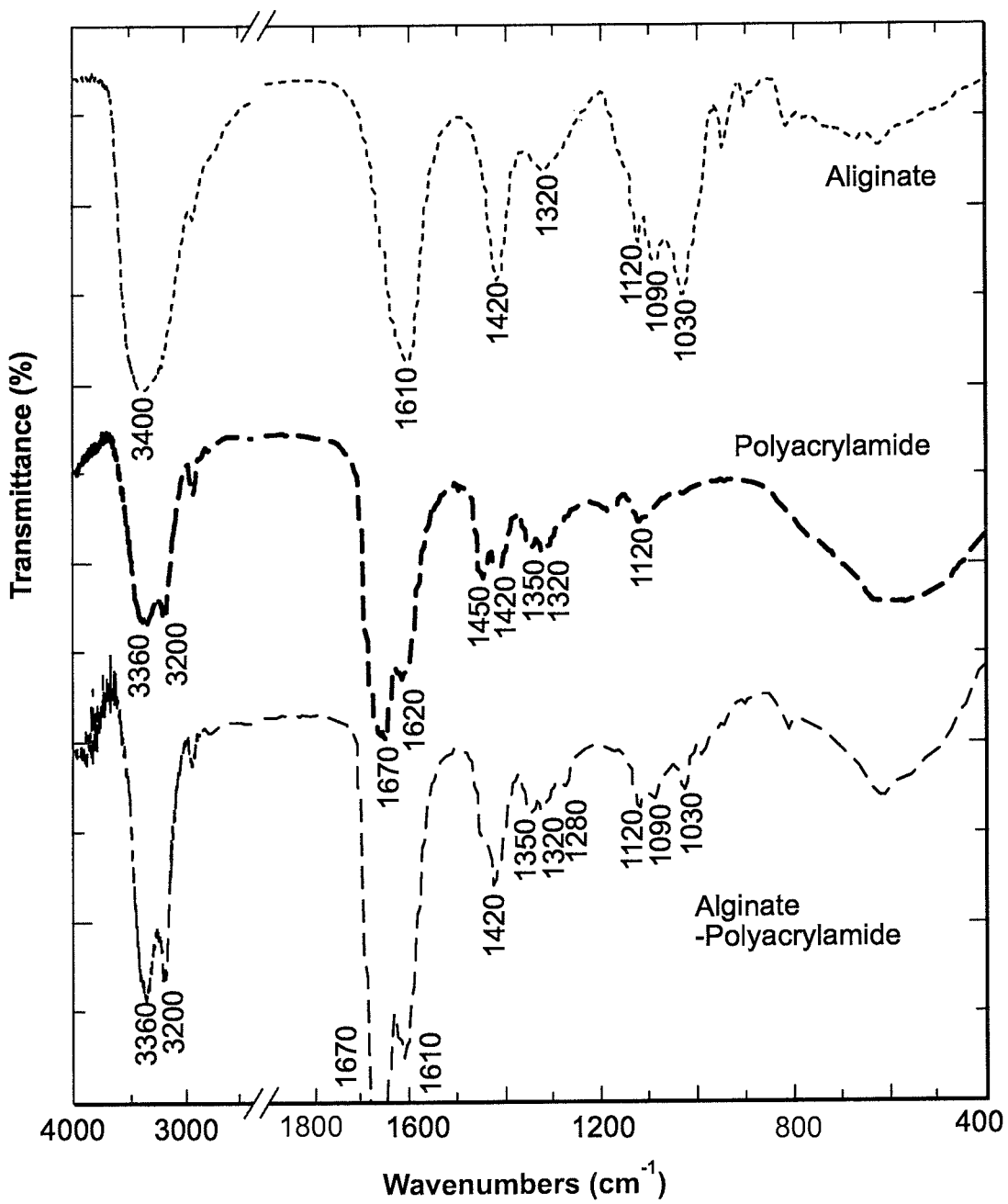
FIG. 19B is a graph showing FTIR spectra: alginate, polyacrylamide, and alginate-polyacrylamide hybrid. This data shown in this figure demonstrates crosslinks between alginate and polyacrylamide.

The FTIR spectra of the three gels are shown in FIG. 19B. The alginate gel showed a broad peak near 3400 $cm^{-1}$ for O—H stretching, one sharp peak at 1620 $cm^{-1}$ for asymmetric COO— stretching, two peaks at 1420 and 1320 $cm^{-1}$ for C—H deformation with secondary alcohols, and three peaks at 1120, 1090, and 1030 $cm^{-1}$ for asymmetric C—O—C stretching, C—O stretching in CH—OH structure, and symmetric C—O stretching in C—O—C structure, respectively. The polyacrylamide gel exhibited bands at 3360 $cm^{-1}$ and 3200 $cm^{-1}$, corresponding to a stretching vibration of N—H, and at 1670 $cm^{-1}$ for C═O stretching. The bands at 1620 $cm^{-1}$ (N—H deformation for primary amine), 1450 $cm^{-1}$ ($CH_2$ in-plane scissoring), 1420 $cm^{-1}$ (C—N stretching for primary amide), 1350 $cm^{-1}$ (C—H deformation), and 1120 $cm^{-1}$ ($NH_2$ in-plane rocking) were also detected. The spectra of the hybrid gel were characterized by comparing the presence of the absorption bands with the pure components. In the spectra of the hybrid gel, a new peak at 1280 $cm^{-1}$ for C—N stretching of secondary amide was created. Furthermore, the intensity of the absorption bands (1620, 1420 $cm^{-1}$) which are related with primary amide, and the intensity of $NH_2$ in-plane rocking peak (1120 $cm^{-1}$) were decreased. Moreover, the intensities of O—H stretching peak (3400 $cm^{-1}$), C—O stretching in CH—OH structure (1090 $cm^{-1}$), and symmetric C—O stretching in C—O—C structure (1030 $cm^{-1}$) were decreased. This result indicates new bonds formed between —$NH_2$ groups of polyacrylamide and carboxyl groups of alginate.

Thermogravimetric Analysis (TGA)

To confirm the two gel networks were covalently coupled, the thermal degradation of the alginate, polyacrylamide, and alginate-polyacrylamide hybrid gels were studied using TGA Q5000 (TA Instruments), under a nitrogen atmosphere at a heating rate of 10° C./min. Samples were scanned from 40 to 750° C. Alginate-polyacrylamide hybrid gel with the polymer ratio 1:6 of alginate to acrylamide was used for this test. Gel samples were frozen at −80° C. and dried in vacuum for a week, then the gels were ground with a mortar. Samples ranging between 4 and 8 mg in weight were tested in platinum pans.

Figure 20A:
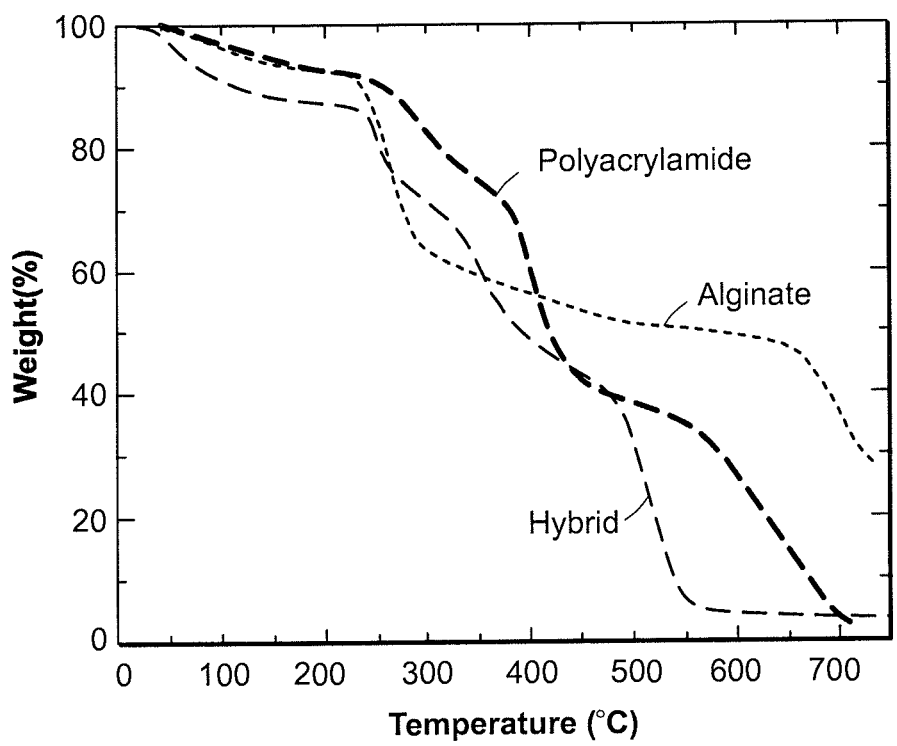
FIGS. 20A-B are line graphs showing the thermal degradation of alginate, polyacrylamide, and alginate-polyacrylamide hybrid gels. A, Data of thermogravimetric analysis (TGA). B, Data of differential thermogravimetry (DTG).
Figure 20B:
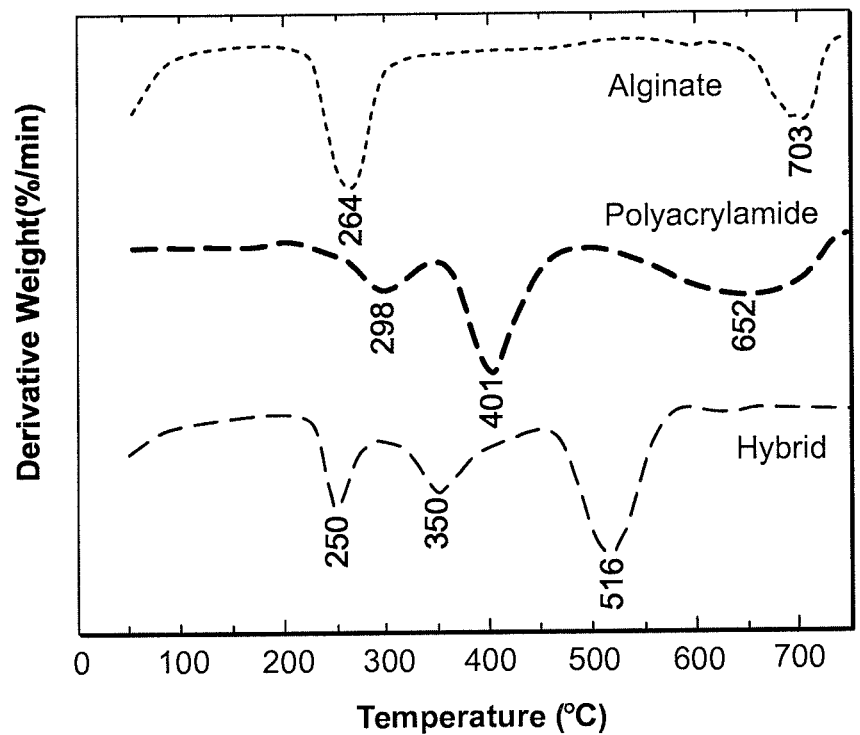

The integral results from the thermogravimetric analysis (TGA) are shown in FIG. 20A, while the differential thermogravimetric data (DTG) are reported in FIG. 20B, for alginate, polyacrylamide, and alginate-polyacrylamide hybrid gels. DTG data were deduced from TGA data by the derivative of the weight loss percent with respect to time. Each peak in DTG curves represents the temperature where the degradation rate is maximum for each degradation stage in the whole process. It was found that alginate has two pyrolysis stages, the first thermal degradation process occurred in the temperature range 225-300° C. The weight loss in first stage is attributed to the degradation of the carboxyl group, as $CO_2$ is released. The second stage occurred in the range 650-740° C., and is attributed to the depolymerization of polymer and formation of a carbonaceous residue, and finally yields $CaCO_3$ as char. The thermal degradation of polyacrylamide occurs in three pyrolysis stages. In the temperature range 230-330° C., one ammonia molecule is liberated for every two amide groups, resulting in the formation of imide. Subsequently, thermal degradation of imides and breaking of the polymer backbone occurs as the second and third stages. Alginate-Polyacrylamide hybrid gel clearly shows three pyrolysis stages instead of the five stages which would result from the sum of the individual materials. Moreover, the locations of the second and third stages of hybrid gel are shifted from the locations of the single networks. Complete chemical analysis from the degradation of hybrid gels is difficult. However, by comparing the trend with previous graft interpenetrating polymers, the reduced number of pyrolysis stages and shifted peak locations of DTG qualitatively support the formation of new covalent bonds between alginate and polyacrylamide.

Energy-Dissipating Mechanisms in Three Types of Gels

When a notched gel is stretched, the deformation is inhomogeneous: the polymer chains directly ahead of the notch are stretched more than the chains elsewhere (FIGS. 21A-C). For the notch in the polyacrylamide gel to turn into a running crack, only the chains directly ahead of the notch need to break. For the notch in the alginate gel to turn into a running crack, only the network directly ahead of the notch need to unzip. In either case, the gel is notch-sensitive because energy dissipates over a highly localized region: only a tiny fraction of the chains in the network—those crossing the crack plane—participate in energy dissipation. By contrast, in the hybrid gel, the number of chains that participate in energy dissipation is dramatically increased. For the notch in the hybrid gel to turn into a running crack, the chains directly ahead of the notch need to break. But before these chains break, the alginate network unzips over a large zone around the root of notch. This is likely the result of the efficient energy transfer between the two networks, due to their direct coupling, that results in alginate chains in a large zone being subjected to stress.

Determination of Fracture Energy

Figure 22A:
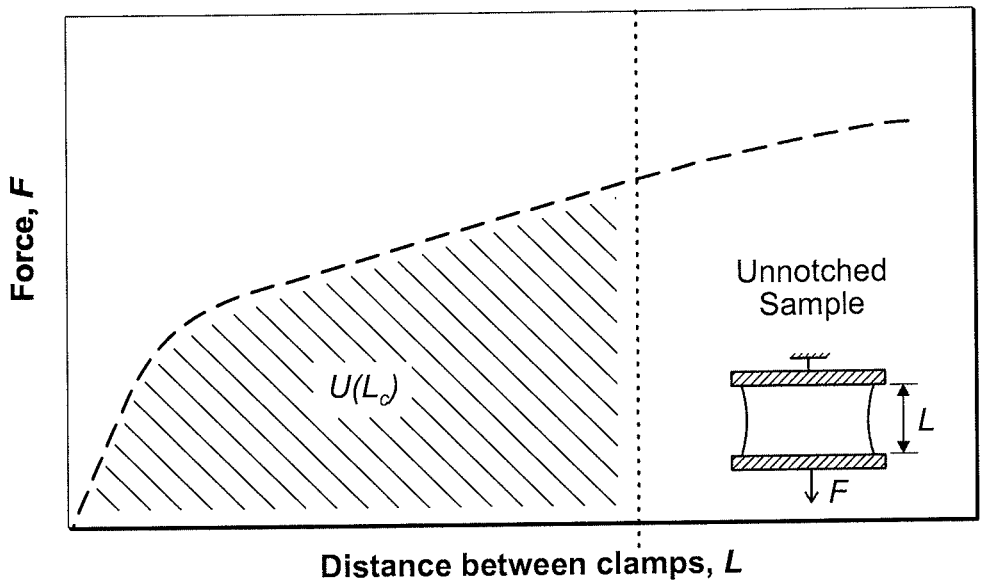
FIGS. 22A-B are line graphs showing determination of fracture energy. Two samples of the same gel were tested in tension. One sample was unnotched, and the other sample was notched. A, The unnotched sample was used to measure the force-length curve. The area beneath the force-length curve gave the work done by the force to the unnotched sample, U(L). B, The notched sample was used to measure the critical distance between the clamps, $L_c$, when the notch turned into a running crack.
Figure 22B:
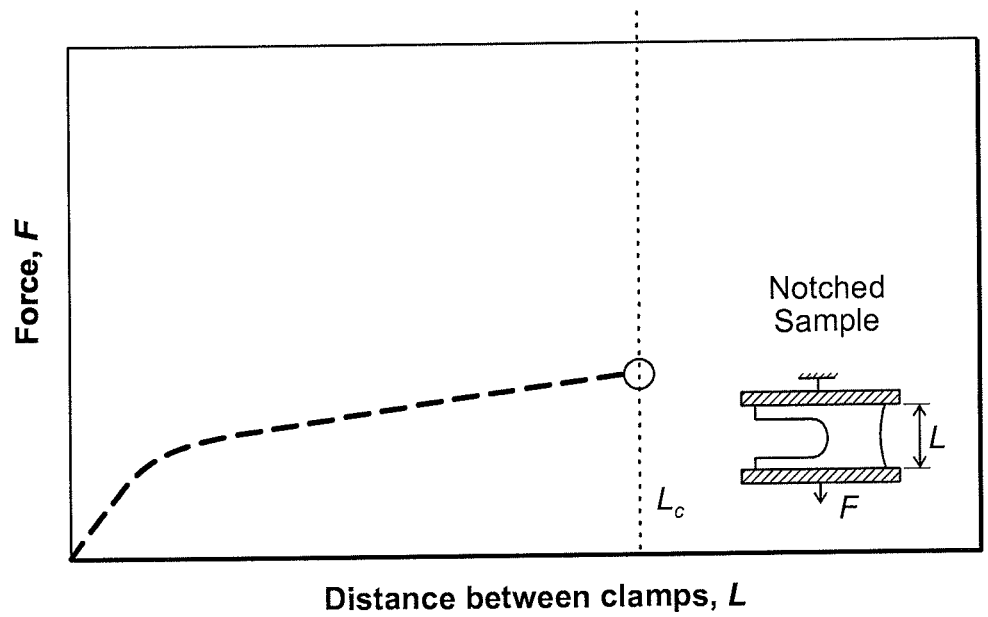

The fracture energy of a gel was determined using a method introduced by Rivlin and Thomas (Rivlin et al., 1953, J. Polym. Sci. 10, 291-318). To adapt the method to measure the fracture energy of an extremely stretchable gel, two samples of the same gel were separately pulled (FIGS. 22A-B). One sample was unnotched, and the other sample was notched. In the initial state when the gel was undeformed, each sample was of width $a_o$=75 mm and thickness $b_o$=3 mm, and the distance between the two clamps was $L_o$=5 mm. The unnotched sample was pulled to measure the force-length curve. (To determine the fracture energy, it was unnecessary to pull the unnotched sample all the way to rupture.) When the two clamps were pulled to a distance L, the area beneath the force-length curve gave the work done by the applied force, U(L). The notched sample was prepared by using a razor blade to cut into the gel a 40 mm-long notch. (The precise length of the notch was unimportant for this test.) The notched sample was pulled, and pictures were taken at a rate of ~30 frames/sec to record the critical distance between the clamps, $L_c$, when the notch turned into a running crack. The fracture energy was calculated from $$\Gamma = \frac{U(L_c)}{a_o b_o}.$$

This method was verified with two other methods: the tensile test with multiple samples containing notches of various lengths, and the double-peeling test. Although the notch turned into a running crack when the sample was pulled to a huge length, the fracture energy determined by all three methods matched well. Even though the entire sample underwent inelastic deformation, the method is still expected to yield a valid test for fracture energy. The situation is similar to testing very ductile metals under large-scale yielding conditions (Begley et al., 1972, The J integral as a fracture criterion. Fracture Toughness, Proceedings of the 1971 National Symposium on Fracture Mechanics, Part II, ASTM STP 514, American Society for Testing and Materials, pp. 1-20).

Tensile Test with Samples of Various Crack Lengths

The pure-shear test was verified with two other tests: tensile test with samples of various crack lengths and double peeling test. Alginate-polyacrylamide hybrid gels with 1:8 polymer ratio, 0.0006 MBAA concentration, 0.1328 CaSO$_4$ concentration, and 86.4 wt. % water concentration were used for this verification.

Figure 23A:
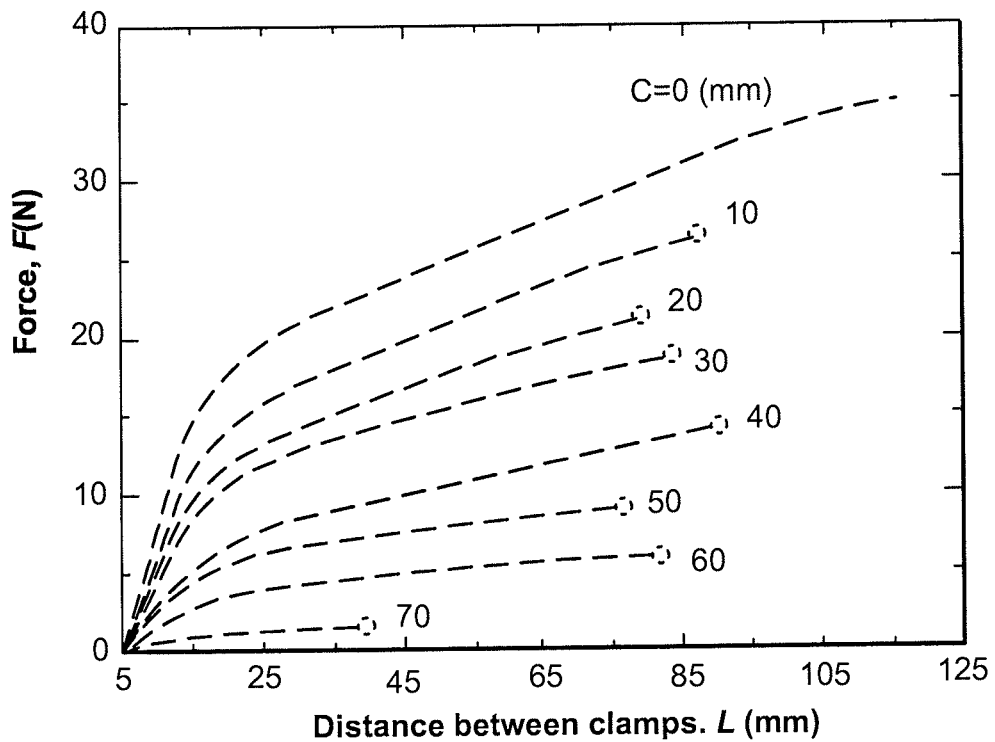
FIGS. 23A-B are line graphs showing verification of the pure shear test method for extremely stretchy materials with tensile test with various crack lengths. A, Force-extension curves for various crack lengths (C) are plotted, the circles in each curve corresponds to the onset of crack propagation. B, The work done in deforming a test piece with various crack lengths was obtained from the area under the force-extension curve with the selected h values.
Figure 23B:
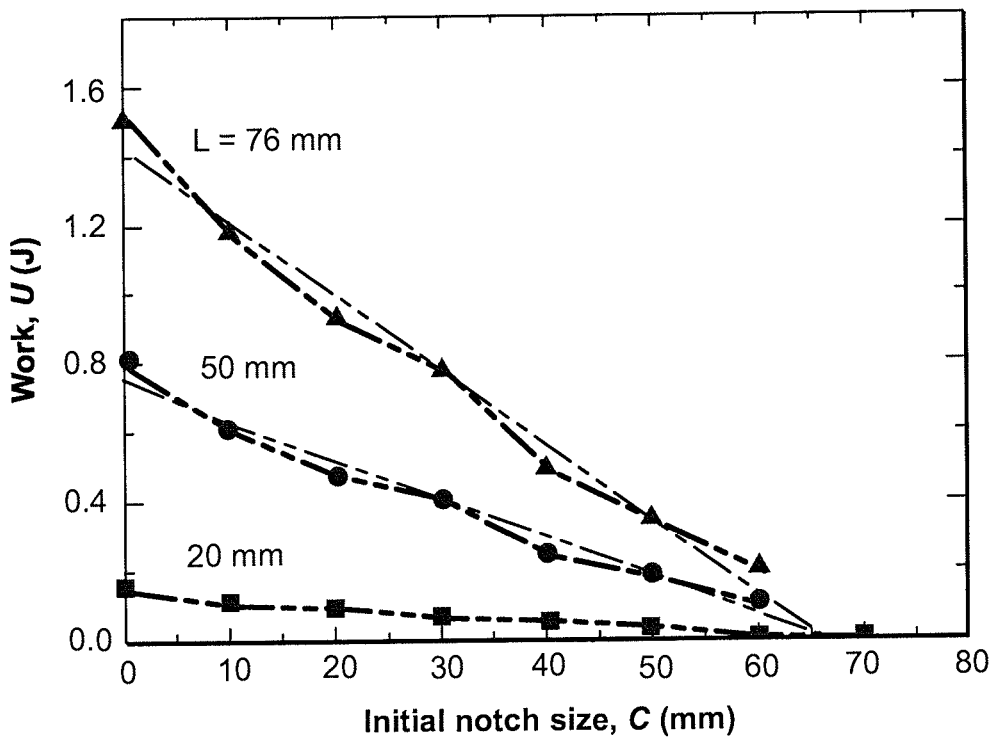

First, tensile tests with various initial crack sizes were used to obtain fracture energy. Samples with dimensions $L_o$=5 mm, $a_o$=75 mm and $b_o$=3 mm were prepared with various crack lengths, C. The configuration of the test is the same as shown in FIGS. 22A-B. Force-extension curves were obtained until the onset of crack propagation occurred. L is the change in distance between the clamps. The total energy U stored in the test piece at $$\left(\frac{\partial U}{\partial C}\right)_L$$

deformation L is obtained by measuring the area under the force-extension curve and U is plotted with the crack lengths, C as shown in FIGS. 23A-B. A suitable L value is selected in a way that it corresponds to L of at least one fractured sample. is calculated from the slope of the total energy vs crack length curve. Thus the fracture energy is given by, $$\Gamma = -\frac{1}{b_o}\left(\frac{\partial U}{\partial C}\right)_L$$

Using this method with L=76 mm, the fracture energy obtained is 7155±400 J/m$^2$ which is comparable with the value 7350 J/m$^2$ which is obtained from the pure-shear test.

Double Peeling Test

Figure 24A:
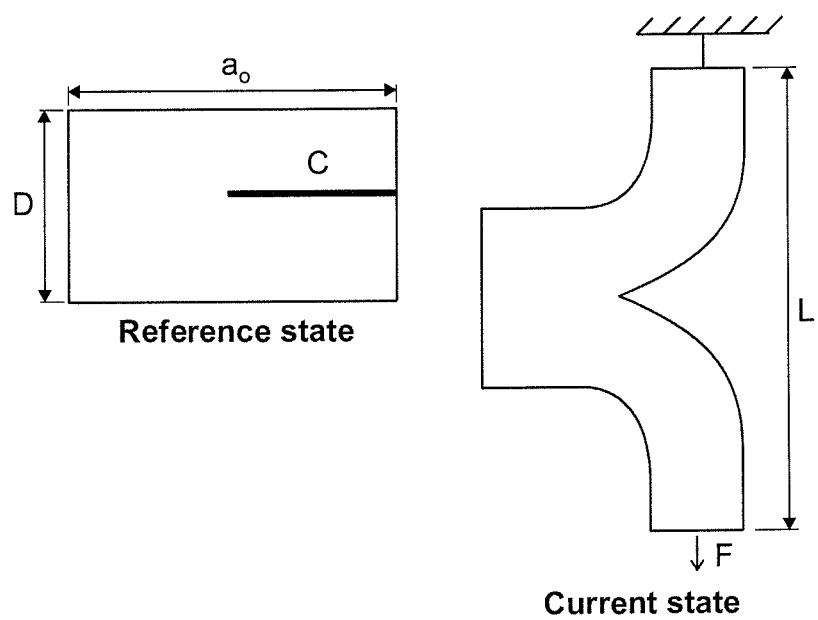
FIG. 24A is a schematic figure of the reference state with dimensions D=15 mm, $a_o$=80 mm, $b_o$=3 mm and current state after deformation are shown.
Figure 24B:
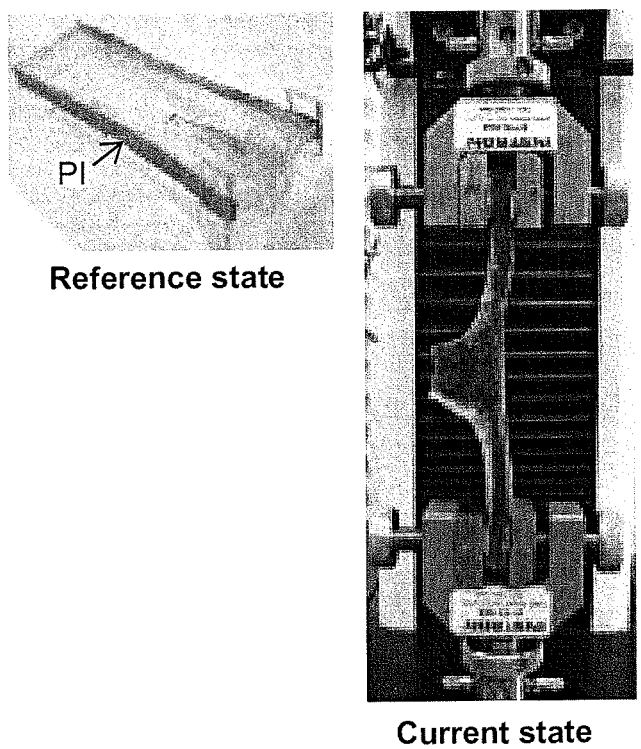
FIG. 24B are photographs showing the double peeling test. PI (Polyimide) strips are attached to the two ends of the specimen to control the deformation in the arms.
Figure 24C:
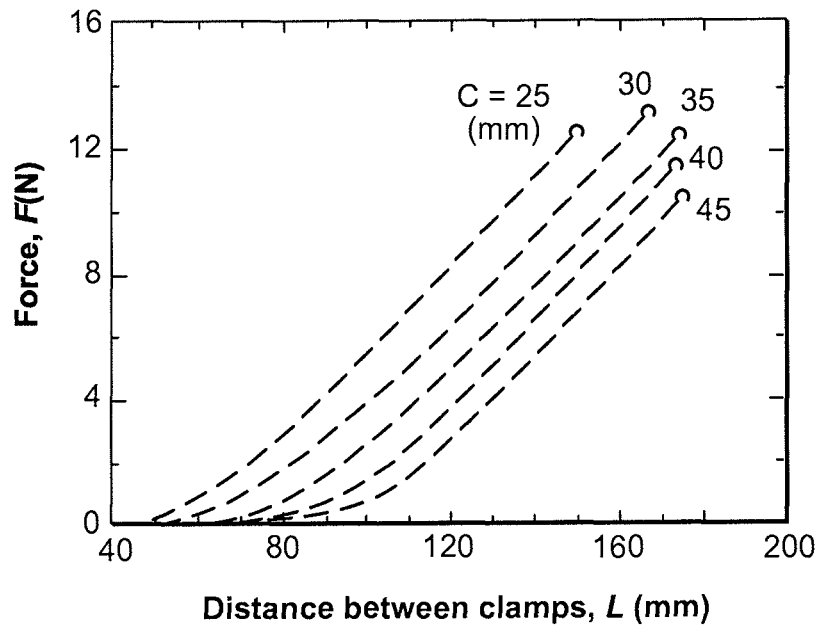
FIG. 24C is a line graph showing force-extension curves for various crack lengths (C) are plotted.
Figure 24D:
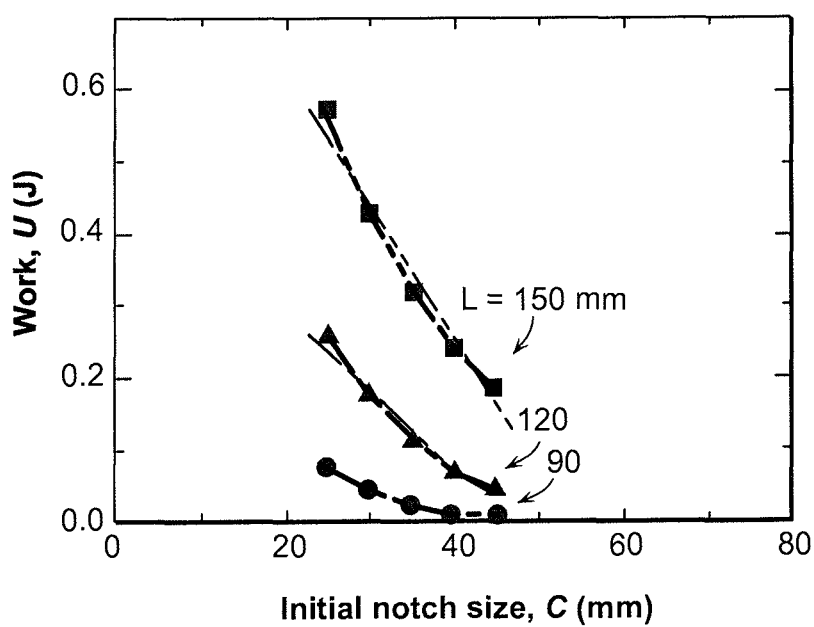
FIG. 24D is a line graph showing the work done in deforming a test piece with various crack lengths were obtained from the area under the load-extension curve with selected h values. These figures show verification of the pure shear test method for extremely stretchy materials with double peeling test method.

In order to verify the pure-shear test for extremely stretchy materials, we also used the double peeling test introduced by Rivlin and Thomas (Rivlin et al., 1953, J. Polym. Sci. 10, 291-318). Samples with dimensions D=15 mm, $a_o$=80 mm and thickness $b_o$=3 mm were prepared with various crack lengths, C as shown in the schematic view in FIG. 24A. To prevent the elongation of the arm of sample during stretching, 200 µm thick polyimide films were glued on both side of sample as shown in FIG. 24B. Force-extension curves are obtained until the onset of crack propagation for various crack lengths as indicated FIG. 24C. The total energy U stored in the test piece at deformation L is obtained by measuring the area under the force-extension curve and U is plotted with the crack lengths C as shown in FIG. 24D. A suitable L is selected as 150 mm and $$\left(\frac{\partial U}{\partial C}\right)_L$$

is calculated from me slope of the total energy vs crack length curve. Fracture energy obtained from this method is 7981±803 J/m$^2$ which is comparable with the value of 7350 J/m$^2$ obtained from the Rivlin-Thomas pure shear test.

Crack Length Effect

Figure 25A:
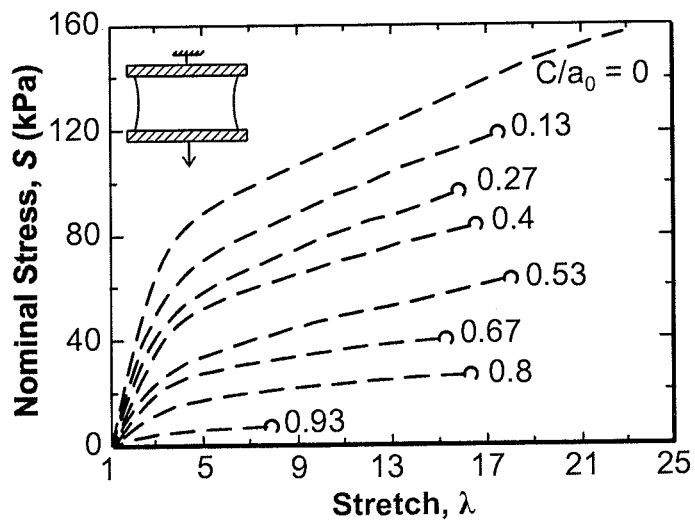
FIGS. 25A-C are line graphs showing the effect of initial crack length on toughness value. A, Stress-stretch curves for various initial crack lengths, the circles denote the onset of crack propagation. B, Critical stretch of the sample with various crack lengths normalized to sample width. C, Fracture toughness of the sample as a function of pre-crack length. (Error bars, S.D.; n=3).
Figure 25B:
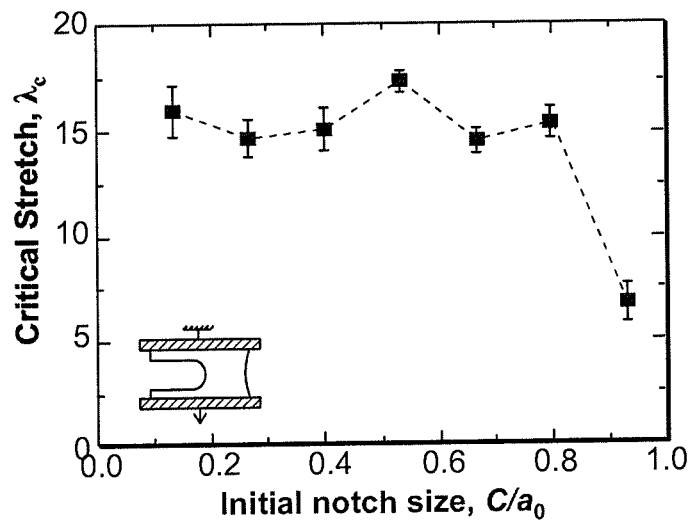
Figure 25C:
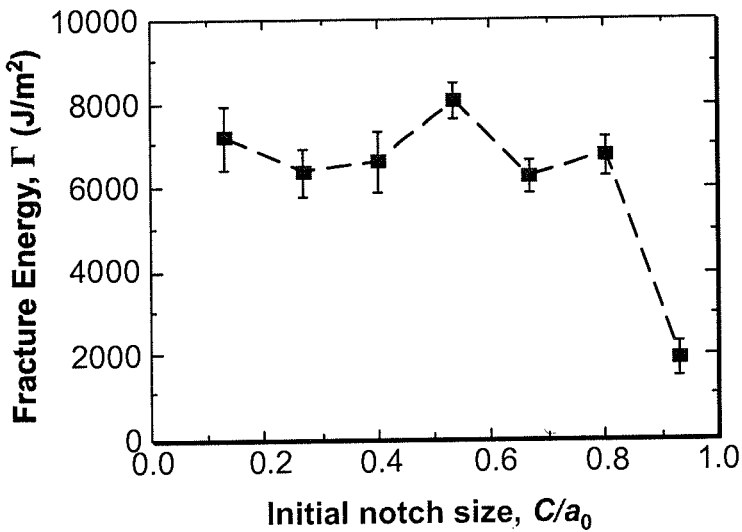
Figure 26A:
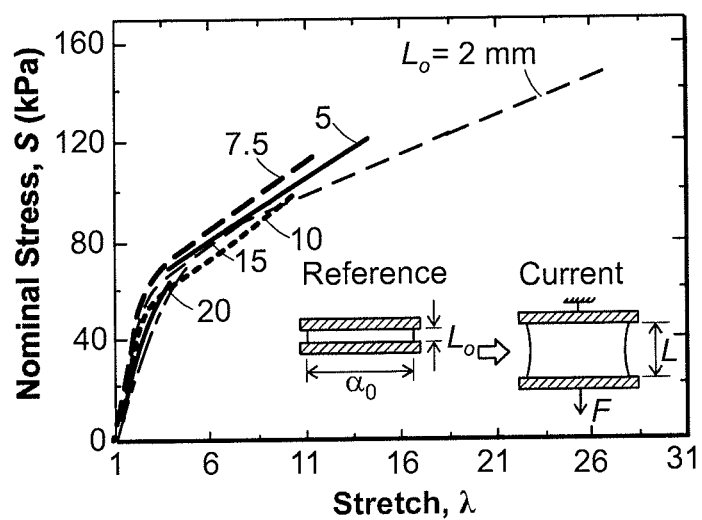
FIGS. 26A-C are line graphs showing the effect of sample length on toughness value. A, Stress-stretch curves for various crack lengths, the circles denote the onset of crack propagation. B, Critical stretch of the sample with various sample lengths normalized with sample width. C, Fracture toughness of the sample as a function of sample length. (Error bars, S.D.; n=3).
Figure 26B:
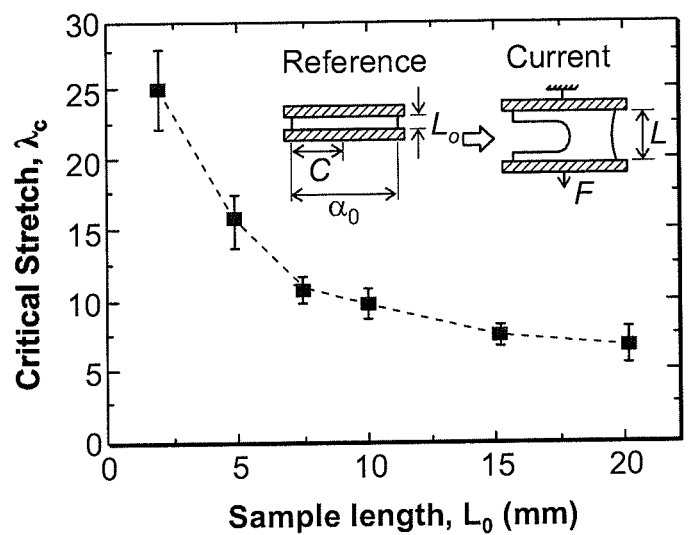
Figure 26C:
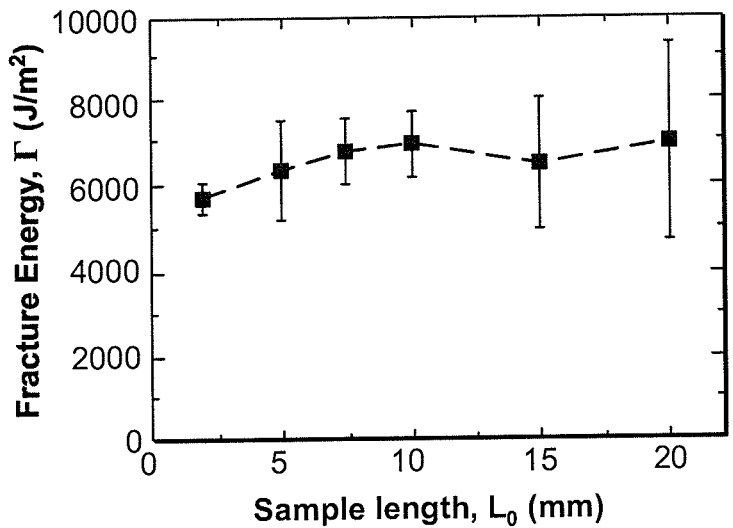
Figure 27A:
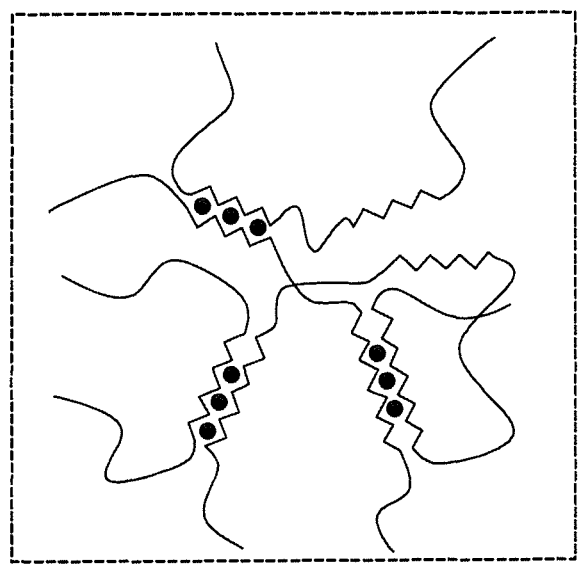
FIGS. 27A-F are schematic diagrams of three types of hydrogels.
Figure 27B:
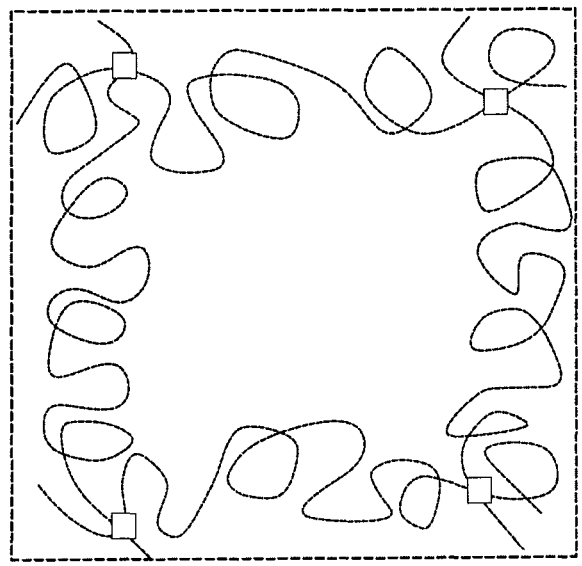
Figure 27C:
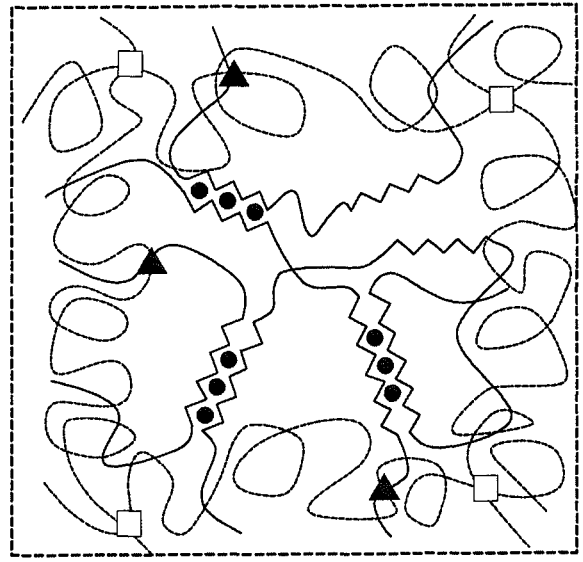
Figure 27D:
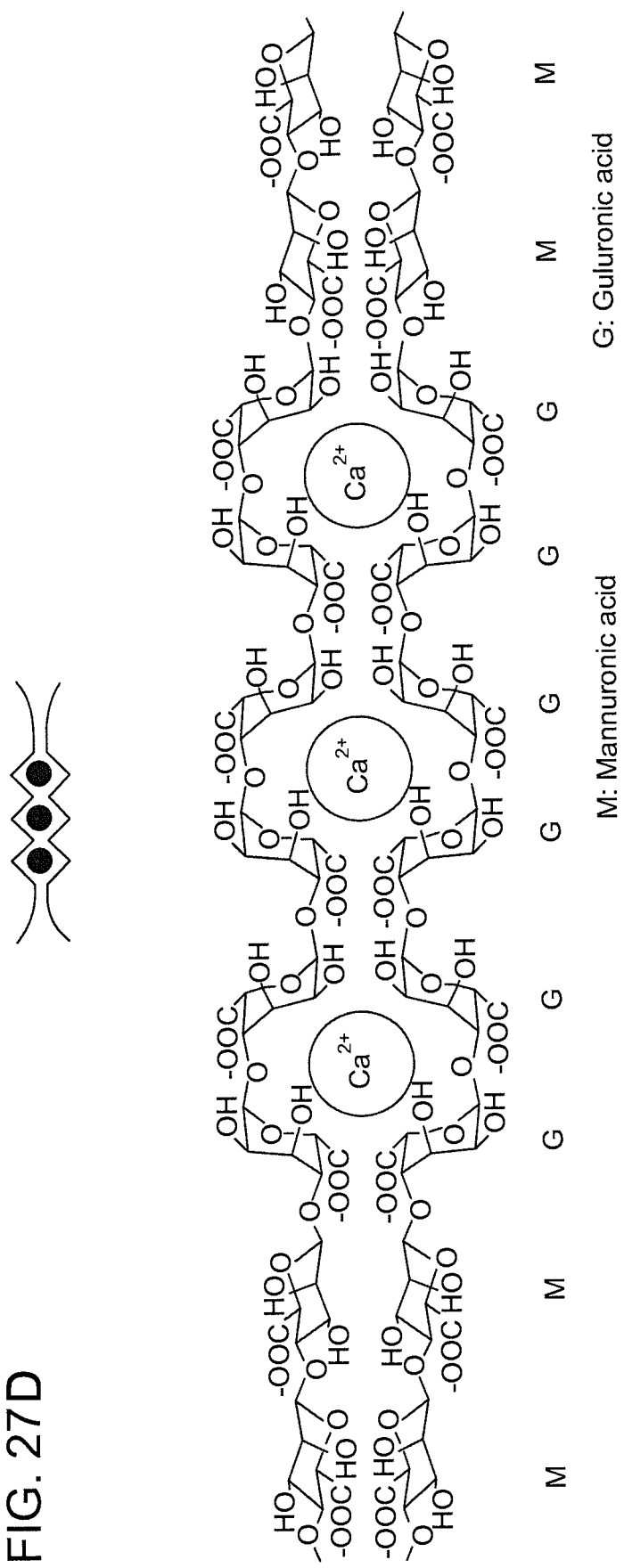
Figure 27E:
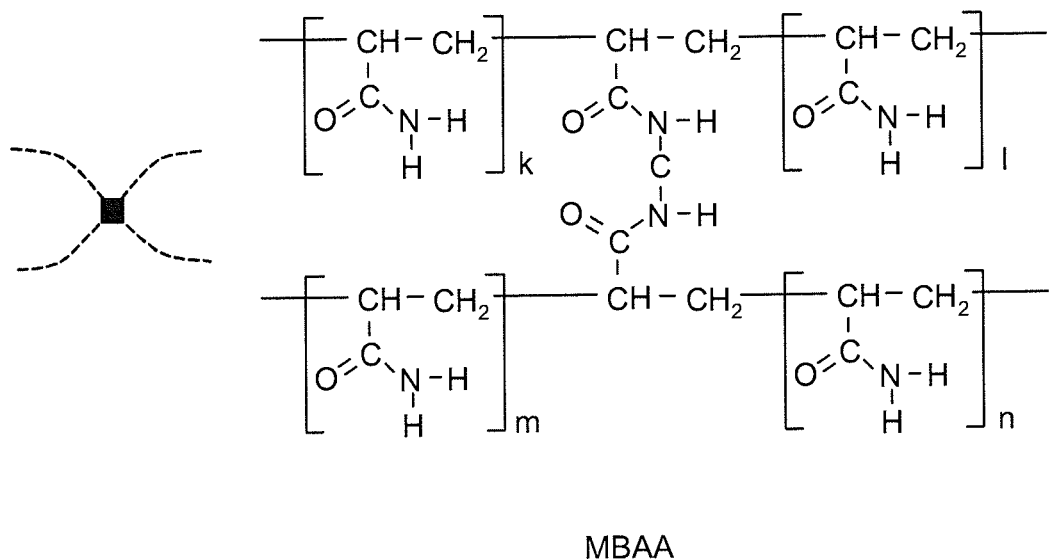
Figure 27F:
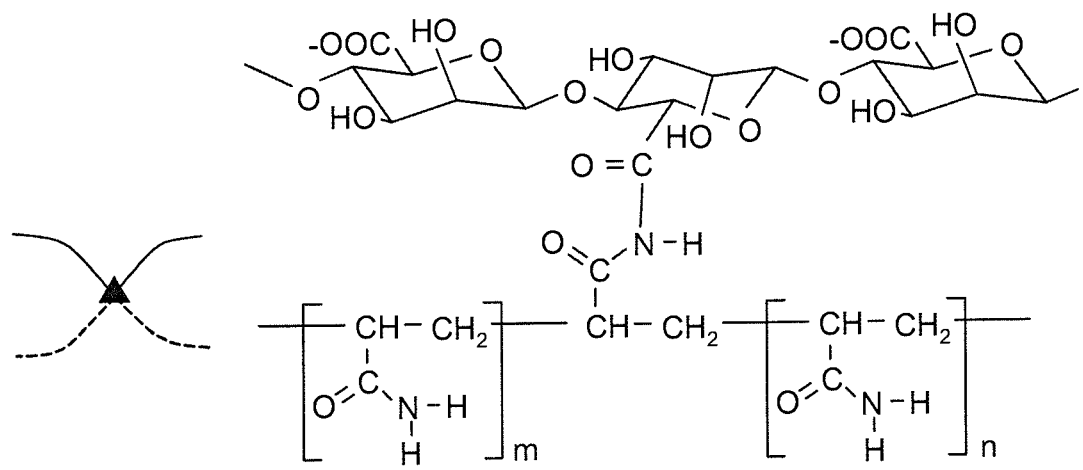

The effect of the initial crack length was investigated with various crack lengths. We prepared and tested samples of initial crack size $C/a_o$=0-0.93. The initial sample length $L_o$=5 mm, width $a_o$=75 mm, and thickness $b_o$=3 mm were fixed for these tests. Alginate-polyacrylamide hybrid gels with 1:8 polymer ratio, 0.0006 MBAA concentration, 0.1328 CaSO$_4$ concentration, and 86.4 wt. % water concentration were used for these tests. Stress-stretch curves were measured with a various crack length until the crack propagation occurred as shown in FIG. 25A. The onset crack propagation critical stretches were collected with various crack lengths and plotted in FIG. 25B. The critical stretches do not vary much by initial crack lengths in the range of $C/a_o < 0.8$. However, the critical stretch decreased to less than half of its value when the ligament length reaches less than 10% of the whole sample width. Fracture energy is calculated and plotted in FIG. 25C as a function of crack lengths. As a result, we obtained a consistent fracture energy within the range of $C/a_o < 0.8$.

Sample Size Effect

To ascertain that the fracture energy is independent of sample size, we prepared and tested samples of initial lengths $L_o = 2\text{-}20$ mm (FIG. 22A-B). The smallest sample, $L_o = 2$ mm was limited by our experimental setup. The initial sample width $a_o = 75$ mm, thickness $b_o = 3$ mm, and notch size $C \approx 0.5 a_o$ were fixed for these tests. While the critical stretch decreased with the sample size, the fracture energy remained nearly a constant. Even though the entire sample underwent inelastic deformation, the method yielded a valid test for fracture energy. The situation is similar to testing very ductile metals under large-scale yielding conditions as described above. This experiment indicates that the intrinsic length scale associated with fracture energy is below the minimum sample size used here, $L_o = 2$ mm. Alginate-polyacrylamide hybrid gels with 1:8 polymer ratio, 0.0006 MBAA concentration, 0.1328 $CaSO_4$ concentration, and 86.4 wt. % water concentration were used for these tests.

Example 3: Highly Stretchable and Tough Hydrogels

Extremely stretchable and tough hydrogels were made by mixing two types of crosslinked polymers: ionically crosslinked alginate and covalently crosslinked polyacrylamide (FIG. 27). An alginate chain consists of mannuronic acid (M unit) and guluronic acid (G unit), arranged in blocks rich in G units, blocks rich in M units, and blocks of alternating G and M units. In an aqueous solution, the G blocks on different alginate chains form ionic crosslinks through divalent cations (e.g., $Ca^{2+}$), resulting in a network in water—an alginate hydrogel. By contrast, in a polyacrylamide hydrogel, the polyacrylamide chains form a network by covalent crosslinks. Powders of alginate (FMC Biopolymer, LF 20/40) and acrylamide (Sigma, A8887) were dissolved in deionized water. Unless otherwise stated, the water content was fixed at 86 wt %. Ammonium persulfate (AP; Sigma, A9164) was added as a photo initiator for polyacrylamide, and N,N-methylenebisacrylamide (MBAA; Sigma, M7279) was added as the crosslinker for polyacrylamide. After degassing the solution in a vacuum chamber, N,N,N',N'-tetramethylethylenediamine (TEMED; Sigma, T7024), 0.0025 the weight of acrylamide, was added as the crosslinking accelerator for polyacrylamide. Calcium sulfate slurry ($CaSO4.2H2O$; Sigma, 31221) was added as the ionic crosslinker for alginate. The solution was poured into a glass mold, $75.0 \times 150.0 \times 3.0$ mm$^3$, covered with a 3-mm thick glass plate. The gel was cured in one step with ultraviolet light (Hoefer, UVC 500) for 1 hour, with 8 W power and 254 nm wavelength at 50° C. The gel was then left in a humid box for 1 day to stabilize the reactions. After curing, the gel was taken out of the humid box, and water on the surfaces of the gel was removed with $N_2$ gas for 1 minute.

Figure 1D:
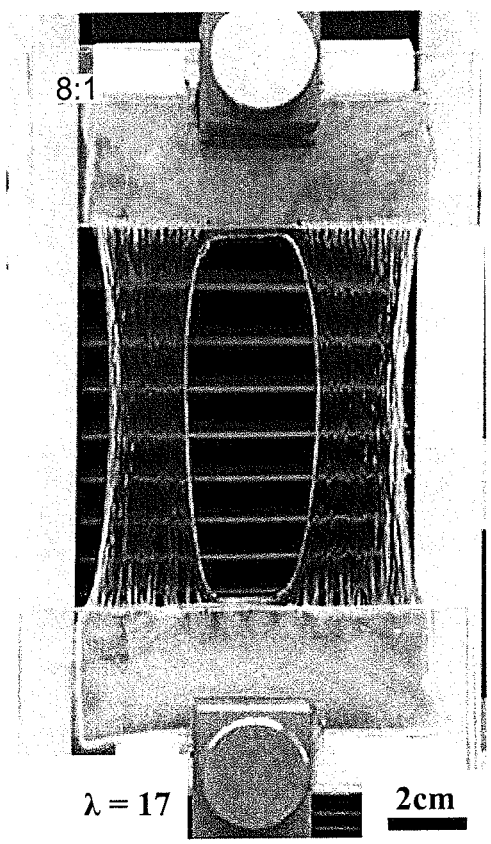

The gel was glued to two clamps made of polystyrene, resulting in specimens of $75.0 \times 5.0 \times 3.0$ mm$^3$. All mechanical tests were performed in air, at room temperature, using a tensile machine (Instron model 3342) with a 500-N load cell. In both loading and unloading, the rate of stretch was kept constant at 2 per minute. An alginate-polyacrylamide hybrid gel was stretched over 20 times its original length without rupture (FIG. 1A,B). The hybrid gel was also extremely notch-insensitive. When a notch was cut into the gel (FIG. 1C) and then pulled the gel to a stretch of 17, the notch was dramatically blunted and remained stable (FIG. 1D). At a critical applied stretch, a crack initiated at the front of the notch, and ran rapidly through the entire sample. Large, recoverable deformation was demonstrated by dropping a metal ball on a membrane of the gel fixed by circular clamps. Upon hitting the membrane, the ball stretched the membrane greatly and then bounced back. The membrane remained intact, vibrated, and recovered its initial flat configuration after the vibration was damped out.

Figure 28A:
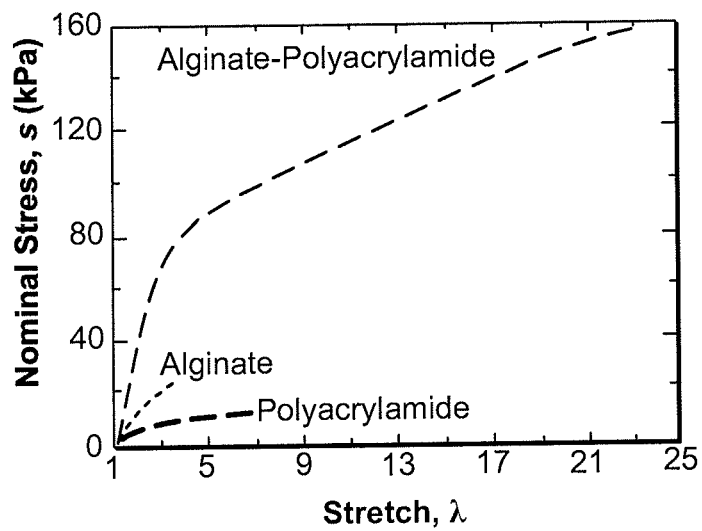
FIGS. 28A-F are line graphs showing the results of mechanical tests under various conditions. A, Stress-stretch curves of the three types of gels, each stretched to rupture. The nominal stress s is defined by the force applied on the deformed gel divided by the cross-sectional area of the undeformed gel. B, The gels were each loaded to a stretch of 1.2, just below the value that would rupture the alginate gel, and were then unloaded. C, Samples of the hybrid gel were subject to a cycle of loading and unloading of varying maximum stretch. D, After the first loading and unloading, one sample was reloaded immediately, and the other sample was reloaded after 1 day. E, Recovery of samples stored at 80° C. for different durations of time. F, The work of the second loading $W_{2\,nd}$ normalized by that of the first loading $W_{1\,st}$ was measured for samples stored for different periods of time at different temperatures. The alginate-to-acrylamide ratio was 1:8 for A and B, and was 1:6 for C—F. The covalent crosslinker, MBAA, was fixed at 0.0006 the weight of acrylamide for polyacrylamide gel and hybrid gel. The ionic crosslinker, $CaSO_4$, was fixed at 0.1328 the weight of alginate for alginate gel and hybrid gel.
Figure 28B:
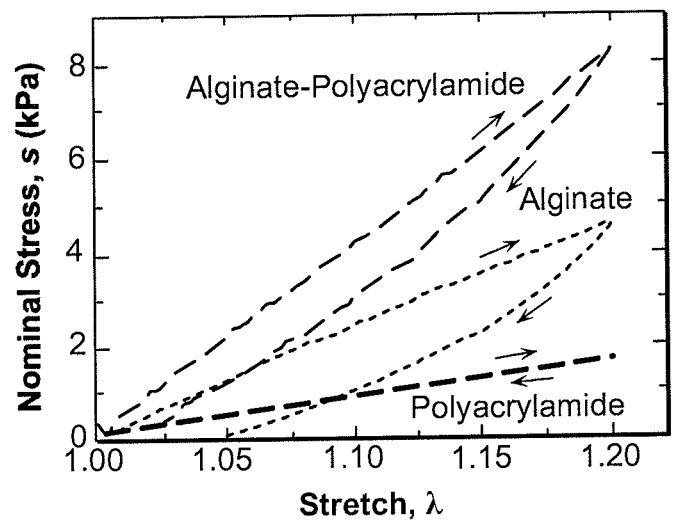
Figure 28C:
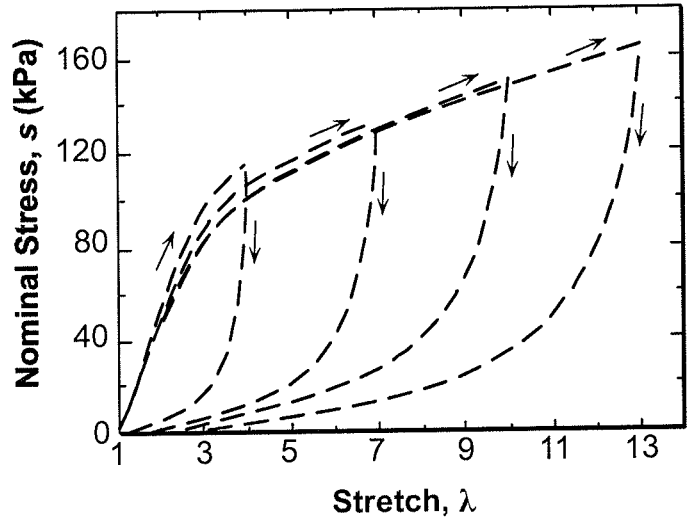

The extremely stretchable hybrid gels are even more remarkable when compared with their parents: the alginate gel and the polyacrylamide gel (FIGS. 28A-C). The amounts of alginate and acrylamide in the hybrid gels were kept the same as those in the alginate gel and polyacrylamide gel, respectively. When the stretch was small, the elastic modulus of the hybrid gel was 29 kPa, which was close to the sum of the elastic modulus of the alginate gel (17 kPa) and that of the polyacrylamide gel (8 kPa). The stress and the stretch at rupture were, respectively, 156 kPa and 23 for the hybrid gel, 3.7 kPa and 1.2 for the alginate gel, and 11 kPa and 6.6 for the polyacrylamide gel. That is, the properties at rupture of the hybrid gel far exceeded those of either of its parents.

Hybrid gels dissipate energy effectively, as shown by pronounced hysteresis. The area between the loading and unloading curves of a gel gave the energy dissipated per unit volume. The alginate gel exhibited pronounced hysteresis and retained significant permanent deformation after unloading. In contrast, the polyacrylamide gel showed negligible hysteresis, and the sample fully recovered its original length after unloading. The hybrid gel also showed pronounced hysteresis, but the permanent deformation after unloading was significantly smaller than that of the alginate gel. The pronounced hysteresis and relatively small permanent deformation of the hybrid gel were further demonstrated by loading several samples to large values of stretch before unloading.

Figure 28D:
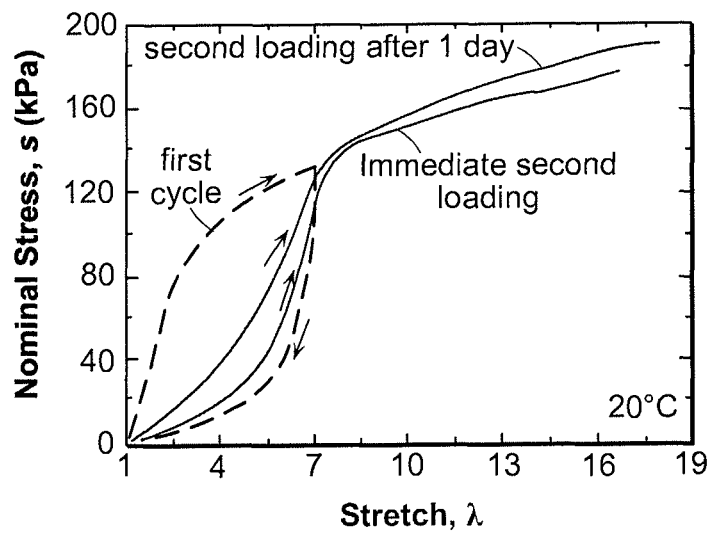
Figure 28E:
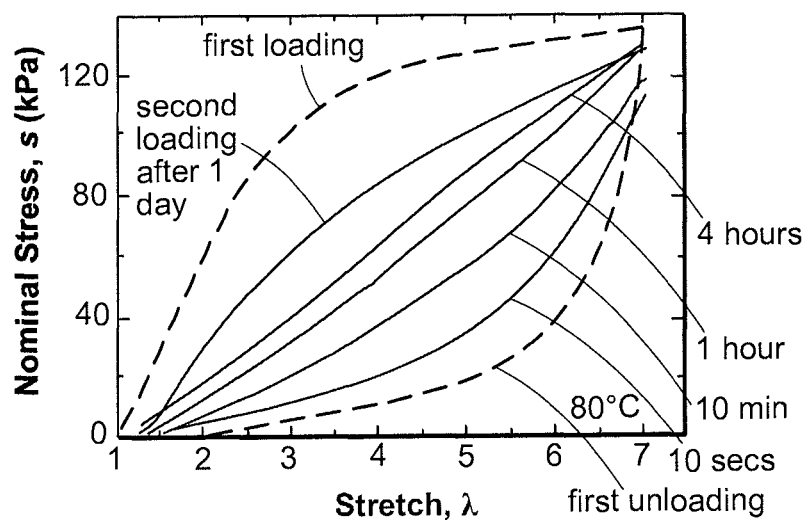
Figure 28F:
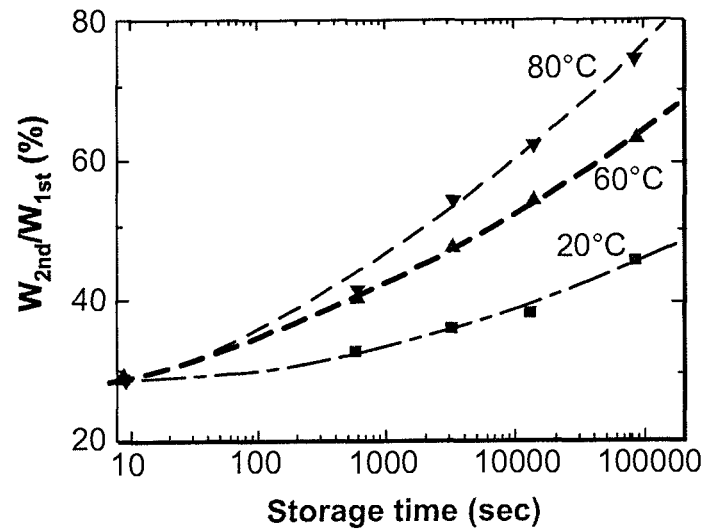

After the first loading and unloading, the hybrid gel was much weaker if the second loading was applied immediately, and recovered somewhat if the second loading was applied 1 day later (FIG. 28D). A sample of the hybrid gel was loaded to a stretch of 7, and then unloaded the gel to zero force. The sample was then sealed in a polyethylene bag and submerged in mineral oil to prevent water from evaporation, and stored in a bath of a fixed temperature for a certain period of time. The sample was taken out of the storage and its stress-stretch curve was measured again at room temperature. The internal damage was much better healed by storing the gel at an elevated temperature for some time before reloading (FIG. 28E). After storing at 80° C. for 1 day, the work on reloading was recovered to 74% of that of the first loading (FIG. 28F).

Figure 29A:
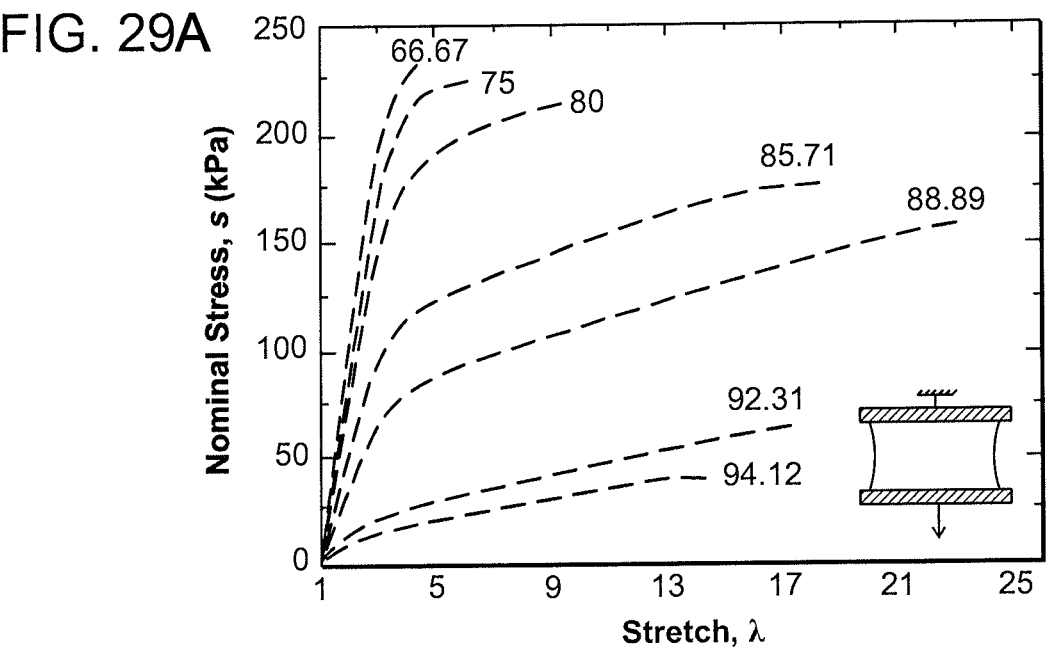
FIGS. 29A-D are line graphs showing that the composition greatly affects the behavior of the hybrid gel. A, Stress-strain curves of gels of various weight ratios of acrylamide and alginate. Each test was conducted by pulling an unnotched sample to rupture. B, Elastic moduli were calculated from stress-strain curves. C, Notched gels of various acrylamide-to-alginate ratios were pulled to rupture to measure the critical stretches. D, Fracture energy was plotted as a function of the acrylamide-to-alginate ratio. The covalent crosslinker, MBAA, was fixed at 0.0006 the weight of acrylamide. The ionic crosslinker, CaSO$_4$, was fixed at 0.1328 the weight of alginate. (Error bars, S.D.; n=4).
Figure 29B:
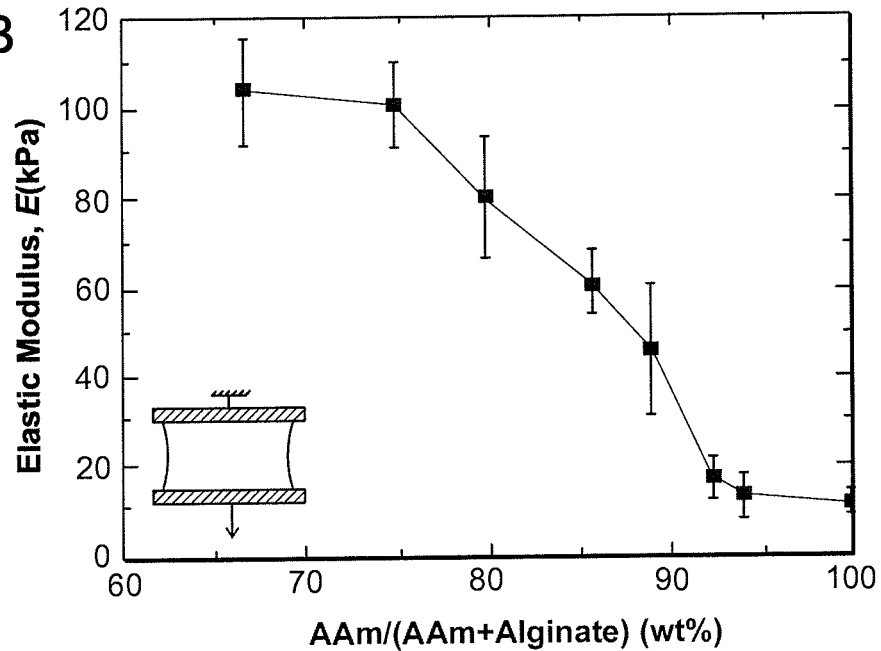
Figure 29C:
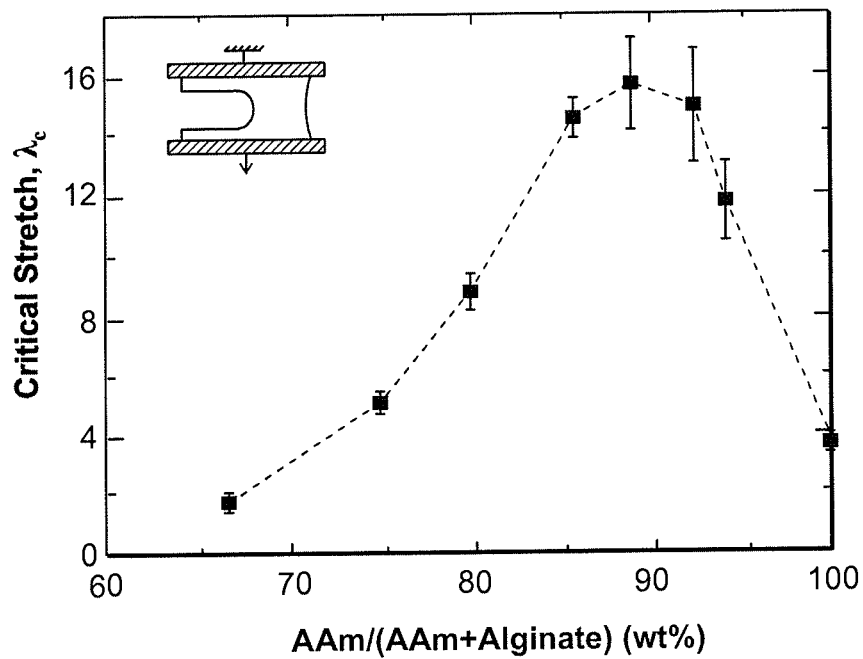
Figure 29D:
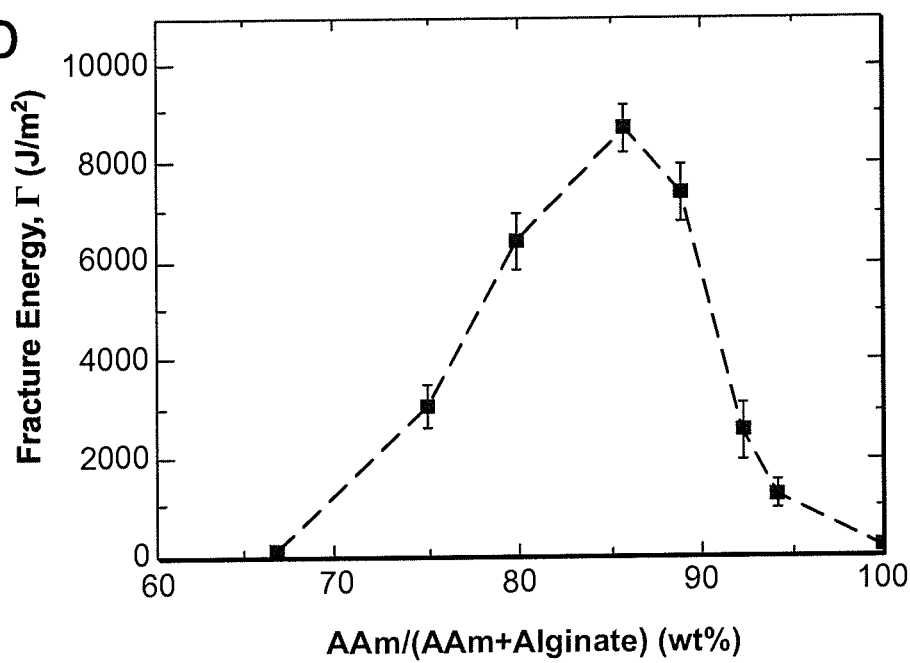

Gels of various proportions of alginate and acrylamide were prepared to study why the hybrids were much more stretchable and stronger than either of their parent compositions. When the proportion of acrylamide was increased, the elastic modulus of the hybrid gel was reduced (FIG. 29A). However, the critical stretch at rupture reached the maximum when acrylamide was 89 wt.-%. A similar trend was observed for samples with notches (FIG. 29C). The fracture energy reached a maximum value of 8700 J/m$^2$ when acrylamide was 86 wt.-% (FIG. 28D). The densities of ionic and covalent crosslinks also strongly affect the mechanical behavior of the hybrid gels, as well as that of pure alginate gels and pure polyacrylamide gels.

The mechanisms of deformation and energy dissipation are discussed below. When an unnotched hybrid gel is subject to a small stretch, the elastic modulus of the hybrid gel is nearly the sum of that of the alginate gel and that of the polyacrylamide gel. This behavior is further ascertained by viscoelastic moduli determined for the hybrid and pure gels. Thus, in the hybrid gel the alginate and the polyacrylamide chains both bear loads. Moreover, alginate is finely dispersed in the hybrid gel homogeneously, as demonstrated by using fluorescent alginate and by measuring local elastic modulus with atomic force microscopy. The load sharing of the two networks may be achieved by entanglements of the polymers, and by possible covalent crosslinks formed between the amine groups on polyacrylamide chains and the carboxyl groups on alginate chains. As the stretch increases, the alginate network unzips progressively, while the polyacrylamide network remains intact, so that the hybrid gel exhibits pronounced hysteresis and little permanent deformation. Since only the ionic crosslinks are broken, and the alginate chains themselves remain intact, the ionic crosslinks can reform, leading to the healing of the internal damage.

The giant fracture energy of the hybrid gel is remarkable, considering that its parents—the alginate gel and polyacrylamide gel—have fracture energies in the range of 10-250 J/m$^2$. The relatively low fracture energy of a hydrogel of a single network with covalent crosslinks is understood in terms of the Lake-Thomas model (Lake et al., 1967, Proc. R. Soc. A 300, 108-119). When the gel contains a notch and is stretched, the deformation is inhomogeneous: the network directly ahead the notch is stretched more than elsewhere. For the notch to turn into a running crack, only the chains directly ahead the notch needs to break. Once a chain breaks, the energy stored in the entire chain is dissipated. In the ionically crosslinked alginate, fracture proceeds by unzipping ionic crosslinks and pulling out chains. After one pair of G blocks unzip, the high stress shifts to the neighboring pair of G blocks and causes them to unzip also. For the notch in the alginate gel to turn into a running crack, only the alginate chains crossing the crack plane need to unzip, leaving the network elsewhere intact. In both polyacrylamide gel and alginate gel, rupture results from localized damage, leading to small fracture energies.

When a notched hybrid gel is stretched, the polyacrylamide network bridges the crack and stabilizes deformation, enabling the alginate network to unzip over a large region of the gel. The unzipping of the alginate network, in its turn, reduces the stress concentration of the polyacrylamide network ahead the notch. The model highlights the synergy of the two toughening mechanisms: crack bridging and background hysteresis.

The fracture energy of the alginate-polyacrylamide hybrid gel, however, is much larger than previously reported values of tough synthetic gels (100-1000 J/m$^2$), a finding which is attributed to how the alginate network unzips. Each alginate chain contains a large number of G blocks, many of which form ionic crosslinks with G blocks on other chains when enough Ca$^{++}$ ions are present. When the hybrid gel is stretched, the polyacrylamide network remains intact and stabilizes the deformation, while the alginate network unzips progressively, with closely spaced ionic crosslinks unzipping at a small stretch, followed by more and more widely spaced ionic crosslinks unzipping as the stretch increases.

Because of the large magnitude of the fracture energy and the pronounced blunting of the notches, a large number of experiments were run to determine the fracture energy, using three types of specimens, as well as changing the size of the specimens. The experiments showed that the measured fracture energy is independent of the shape and size of the specimens. The data indicate that the fracture energy of hydrogels can be dramatically enhanced by combining weak and strong crosslinks. The combination of relatively high stiffness, high toughness and recoverability of stiffness and toughness, along with an easy method of synthesis, make these materials an ideal candidate for tissue engineering as well as other clinical and non-clinical, e.g., industrial, uses.

Example 4: Biocompatibility/Degradation

In order to assess the potential of the hydrogel material for biomedical applications, in vitro cytotoxicity and biocompatibility were examined, as well as degradation of the material in a cell culture environment. As described in detail below, live/dead staining, a WST cytotoxicity assay, and proliferation study were performed to examine the biocompatibility. All assays were performed using the mouse mesenchymal stem cell line D1. Compression testing was performed to examine mechanical degradation over time in cell culture conditions.

Biocompatibility Tests

Two different schemes were used to examine biocompatibility: 1) cumulative, and 2) snapshot. The general paradigm is to condition cell culture media by soaking gels in the media for various time points and then assaying the biocompatibility of the gels.

Scheme 1: In this scheme, hybrid gels were prepared using the techniques described above in two different crosslinking densities. Polyacrylamide (PAAM) and alginate gels were also prepared as controls, using the same wt % polymer as in the hybrid gels. Before testing, these gels were washed 3× in serum-free DMEM (Lonza). At time zero, three circular gels (3 mm thick, 8 mm diameter) per time point were placed in 25 mL complete cell culture media (DMEM, 10% Fetal Bovine Serum, 1% penicillin/streptomycin) and were placed in cell culture conditions (37° C., 5% $CO_2$). At the time points of interest, the gels were removed from the media, which was then frozen. After all time points were completed, the media was thawed and used as the cell culture media for the assays to follow, described below. Hence, this scheme examined potential cumulative release or degradation.

Scheme 2: In this scheme, gels were prepared using the techniques described above. Polyacrylamide (PAAM) and alginate gels were also prepared as controls, using the same wt % polymer as in the hybrid gels. Before testing, these gels were washed 3× in serum-free DMEM (Lonza). At time zero, fifteen circular gels (3 mm thick, 8 mm diameter) per time point were placed in 35 mL complete cell culture media (DMEM, 10% Fetal Bovine Serum, 1% penicillin/streptomycin) and were placed in cell culture conditions (37° C., 5% $CO_2$). At the time points of interest, three gels were removed from the media, and were transferred to 25 mL fresh complete media for three days, which was then frozen. After all time points were completed, the media was thawed and used as the cell culture media for the assays to follow, described below. Hence, this scheme examined "snapshots" of potential cumulative release or degradation.

WST Assay

The WST Cell Proliferation Assay kit is used for quantification of cell proliferation and viability. The assay is based on the cleavage of the tetrazolium salt WST-1 to formazan by cellular mitochondrial dehydrogenases. Expansion in the number of viable cells results in an increase in the overall activity of the mitochondrial dehydrogenases in the sample. The augmentation in enzyme activity leads to the increase in the amount of formazan dye formed. The formazan dye produced by viable cells can be quantified by a multiwell spectrophotometer (microplate reader) by measuring the absorbance of the dye solution at 440 nm. The assay can be used for the measurement of cell proliferation in response to growth factors, cytokines, mitogens and nutrients. It can also be used for the analysis of cytotoxic compounds.

Figure 30:
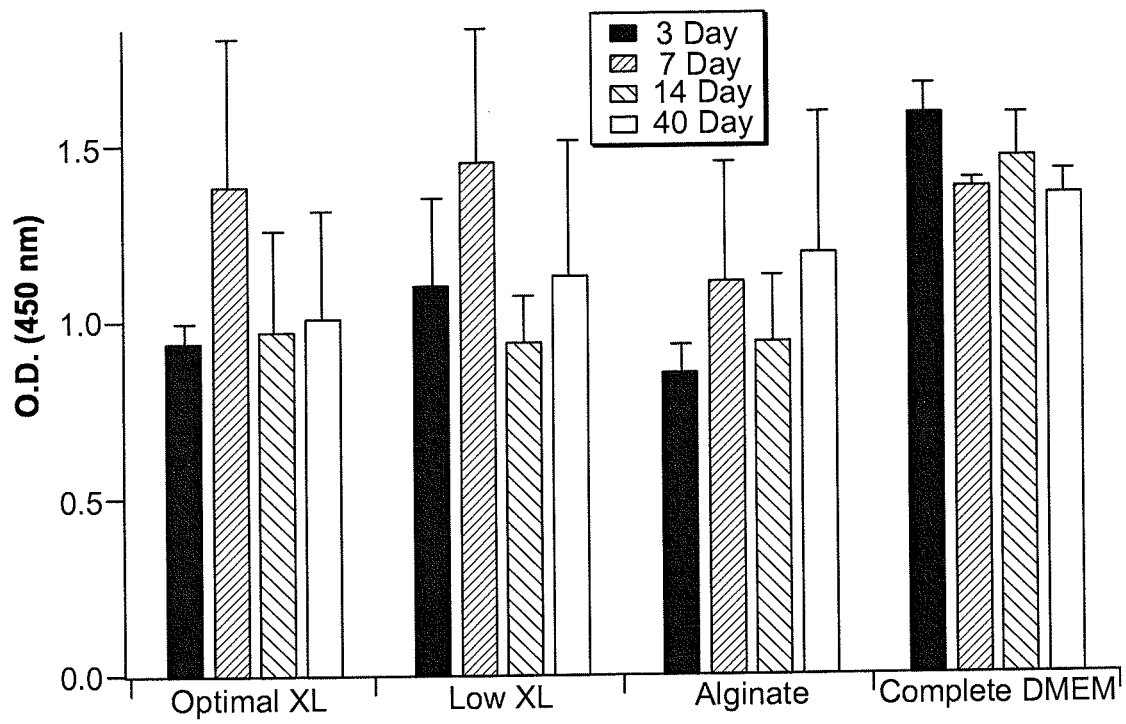
FIG. 30 is a bar chart showing the results of conditioning cell culture media by soaking gels in the media for various time points, and then performing a WST cytotoxicity assay to determine the effects of potential cumulative release or degradation of the gel.
Figure 31:
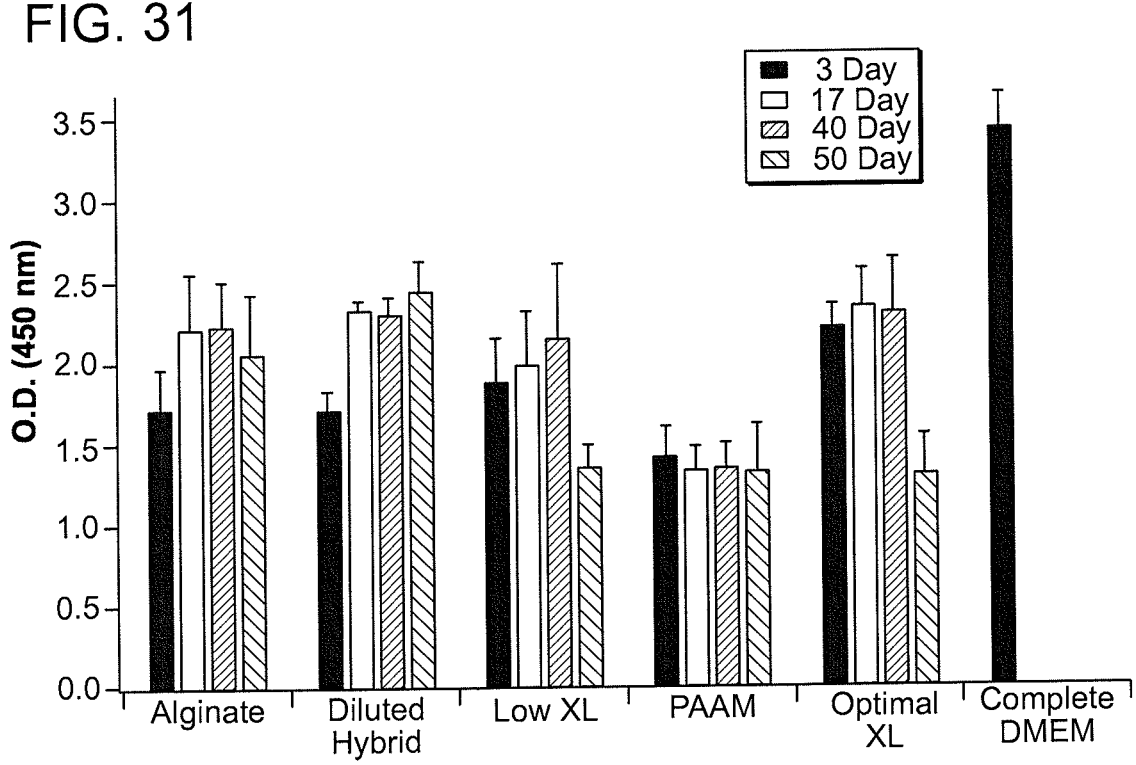
FIG. 31 is a bar chart showing the results of conditioning cell culture media by soaking gels in the media for various time points, and then performing a WST cytotoxicity assay to determine the effects of "snapshots" of potential cumulative release or degradation of the gel.

As the WST Assay measures a cell's mitochondrial activity and metabolic health, this assay determines cytotoxicity. For the conditioned media collected via both schemes described above, the WST assay (Millipore) was performed per the manufacturer's instructions after seeding 5000 D1 cells/well in 100 µL complete culture media for 8 hours before changing to 100 µL conditioned media for 72 hours prior to the assay. Subsequently, the plates were read measuring absorbance at 450 nm using a BioTek plate reader. Results for the WST Assay for scheme 1 and scheme 2 are shown in FIGS. 30 and 31, respectively. Little or no cytotoxicity was observed using IPN hydrogels with low and optimal crosslinking. As shown in FIGS. 30 and 31, the conditioned media was not cytotoxic to the cells examined. The cytotoxicity profile of the IPN hydrogels was similar to the profile of alginate, which is generally regarded as non-toxic and biocompatible.

Proliferation Assay

Figure 32:
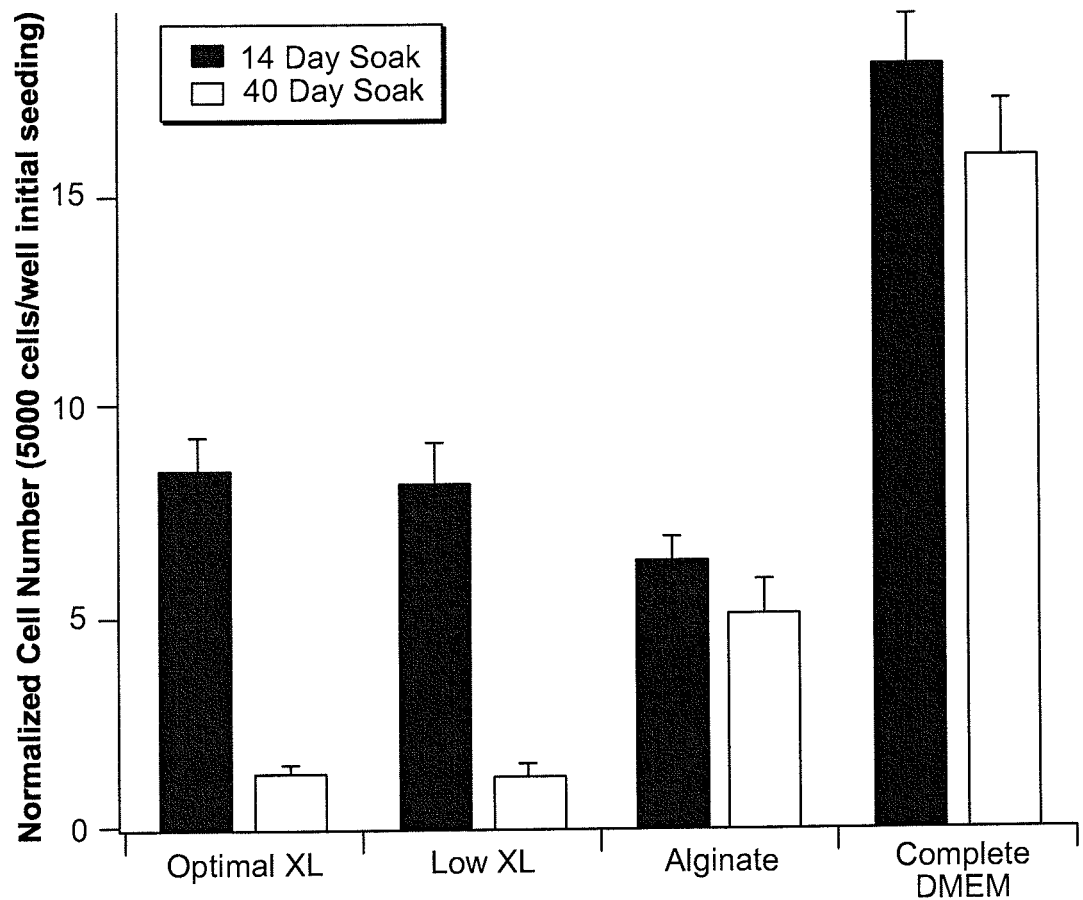
FIG. 32 is a bar chart showing the results of conditioning cell culture media by soaking gels in the media for various time points, and then performing a proliferation assay to determine the effects of potential cumulative release or degradation of the gel.
Figure 33:
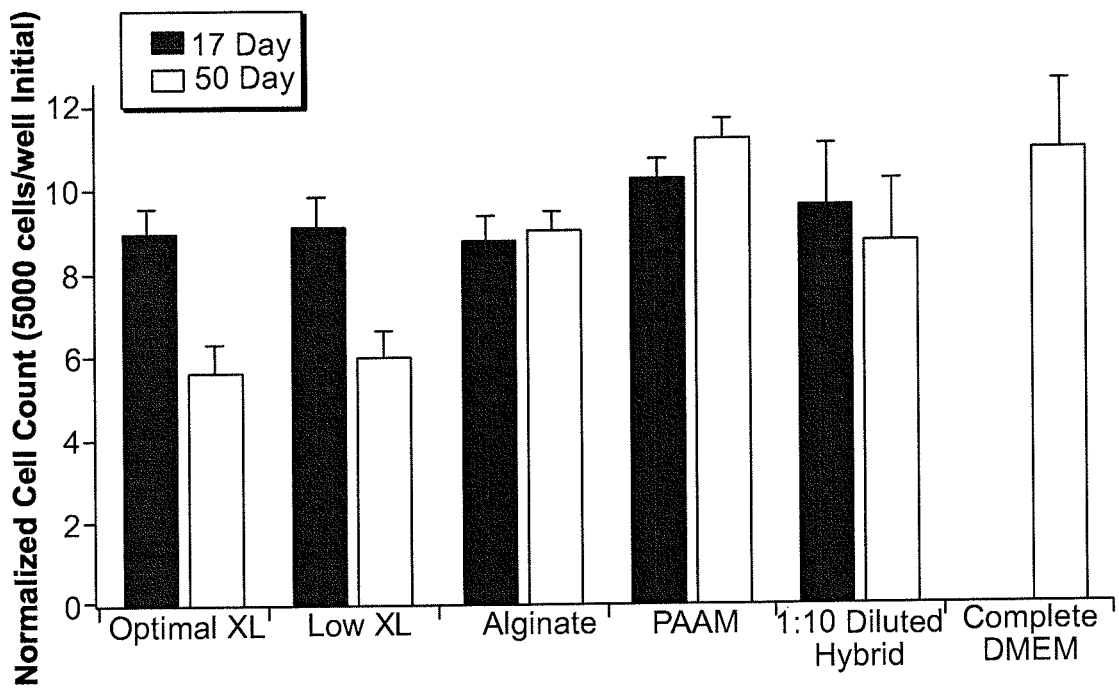
FIG. 33 is a bar chart showing the results of conditioning cell culture media by soaking gels in the media for various time points, and then performing a proliferation assay to determine the effects of "snapshots" of potential cumulative release or degradation of the gel.

In 24 well-plates, D1 cells were seeded at 5000 cells/well in 500 µL complete media and allowed to adhere for 6 hours in standard cell culture conditions. Media was changed to conditioned media from both schemes, and after 72 hours, cells were counted using a Coulter Counter (Beckman Coulter). Results for the Proliferation Assay for scheme 1 and scheme 2 are shown in FIGS. 32 and 33, respectively, and report the cell count normalized by the initial seeding number.

Live/Dead Staining

Figure 34:
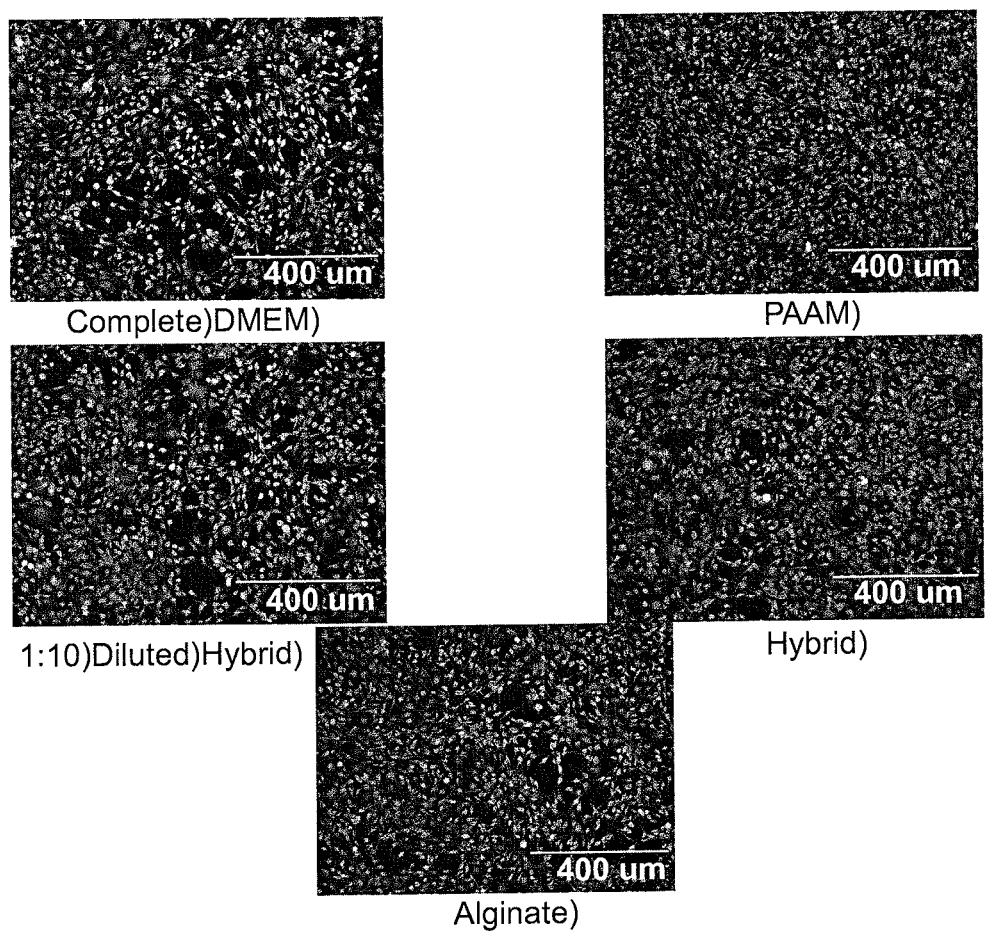
FIG. 34 is a series of photomicrographs showing the results of conditioning cell culture media by soaking gels in the media for 50 days, and then performing a live/dead staining assay to determine the effects of "snapshots" of potential cumulative release or degradation of the gel. Live cells appear green, while dead cells appear red.

For the 50 day time point in scheme 2, cells were cultured exactly as in the proliferation assay. However, instead of counting, live/dead staining was performed using the Live/Dead Kit (Life Technologies) per the manufacturer's instructions. Fluorescence images were acquired using 488 nm and 514 nm excitation channels. Results for the Live/Dead Images for are given in FIG. 34. As shown in FIG. 34, media conditioned with the hybrid gels was not more cytotoxic to cells than the control.

Thus, data from the live/dead staining, proliferation, and WST assays indicated that IPN hydrogels are biocompatible and suitable for clinical use.

Degradation/Compression Tests

Figure 35:
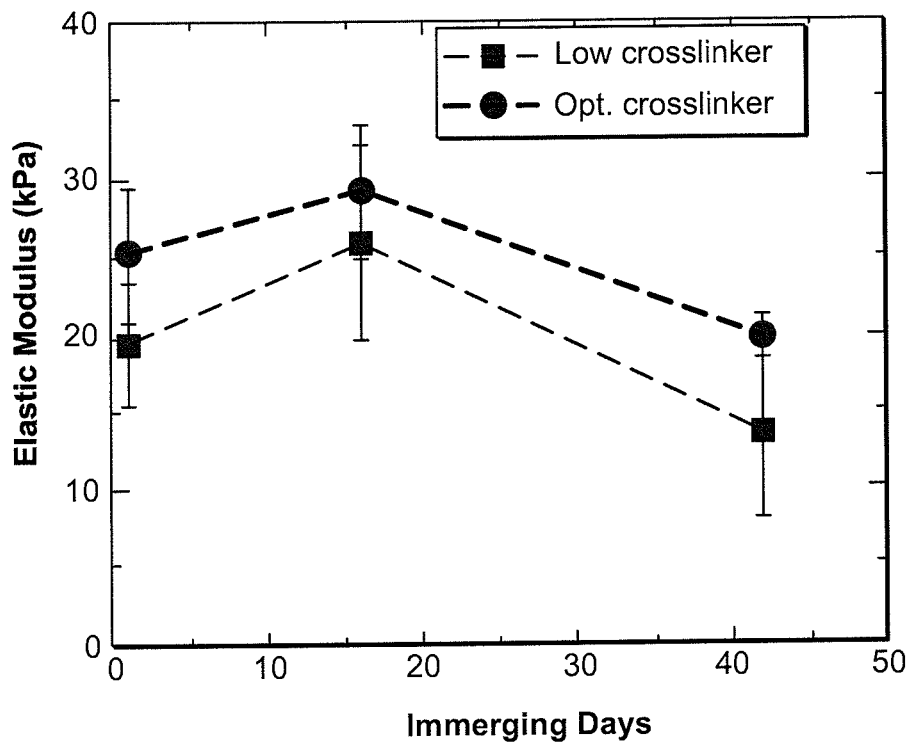
FIG. 35 is a line graph showing the results of conditioning cell culture media by soaking gels in the media for various time points, and then performing compression tests using a mechanical testing apparatus to determine Young's Modulus as a function of soaking time.

Gels were soaked for various times as described in Scheme 1. Upon removal from the media, gels were subjected to compression tests using a mechanical testing apparatus (Instron), with a 50N load cell and a compressive strain rate of 1 mm/min. From these tests, the Young's Modulus was calculated. Results for Young's Modulus as a function of soaking time are given in FIG. 35.

In many applications, the use of hydrogels has often been severely limited by their mechanical properties. For example, the poor mechanical stability of hydrogels used for cell encapsulation often leads to unintended cell release and death, and low toughness limits the durability of contact lenses. The tough hydrogel compositions described herein overcome many of the drawbacks of earlier hydrogels. Hydrogels of superior stiffness, toughness, stretchability and recoverability lead to improved performance in these applications, and open up new areas of application for this class of materials.

Effect of Gel Curing Temperature on Gel Fracture Toughness

Figure 36:
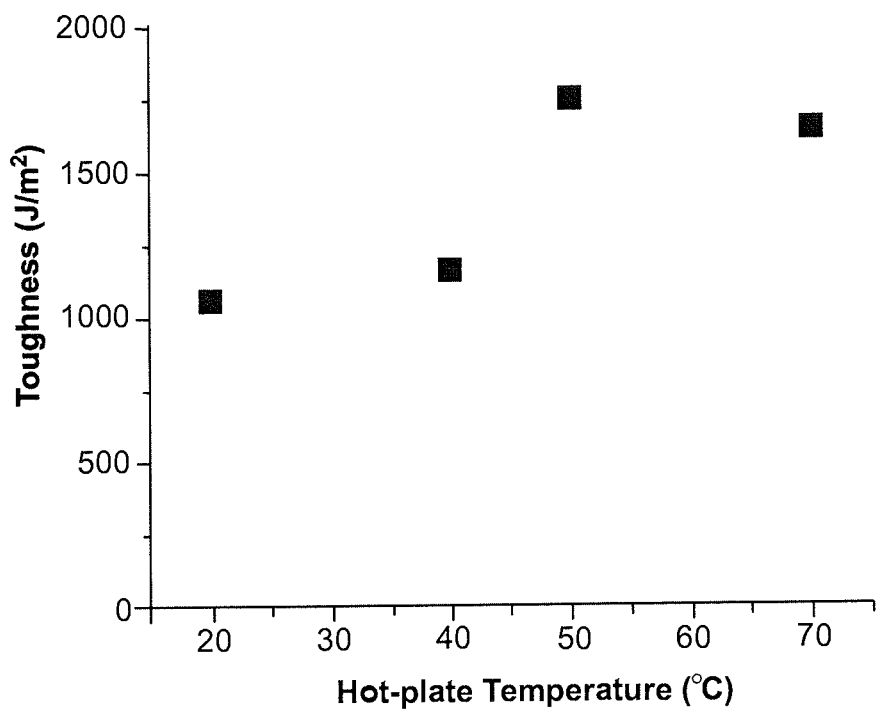
FIG. 36 is a dot plot showing the effect of temperature during gelling on hydrogel fracture toughness. The fracture toughness of polyacrylamide-alginate hybrid hydrogels was tested with various curing temperatures.

The fracture toughness of polyacrylamide-alginate hybrid hydrogels was examined with various curing temperatures (FIG. 36). Acrylamide-alginate water solutions were poured in 5 mm thick glass molds and placed on top of hot plate. The gels were cured by ultraviolet light for 1 hour with a fixed hot plate temperature. The weight ratio of alginate to acrylamide was fixed at 1:10, and the water content was fixed at 86 wt %. The ionic crosslinker, $CaSO_4$, was fixed at 0.2657 the weight of alginate. The covalent crosslinker, MBAA, was fixed at 0.0006 the weight of acrylamide. As shown in FIG. 36, a hot plate temperature of about 50° C. and about 70° C. resulted in a gel fracture toughness of about 1750 $J/m^2$ and 1625 $J/m^2$, respectively. Thus, allowing the hydrogels to cure at an increased temperature results in an increase in fracture toughness Chemical Bonds Between Two Networks One mechanism for the development of covalent chemical bonds between two networks involves linking between carboxylic acid (COOH) on alginate chains and amide ($NH_2$) on the acrylamide network (Sun et al., 2012 Nature, 6; 489(7414):133-6, incorporated herein by reference).

Figure 37:
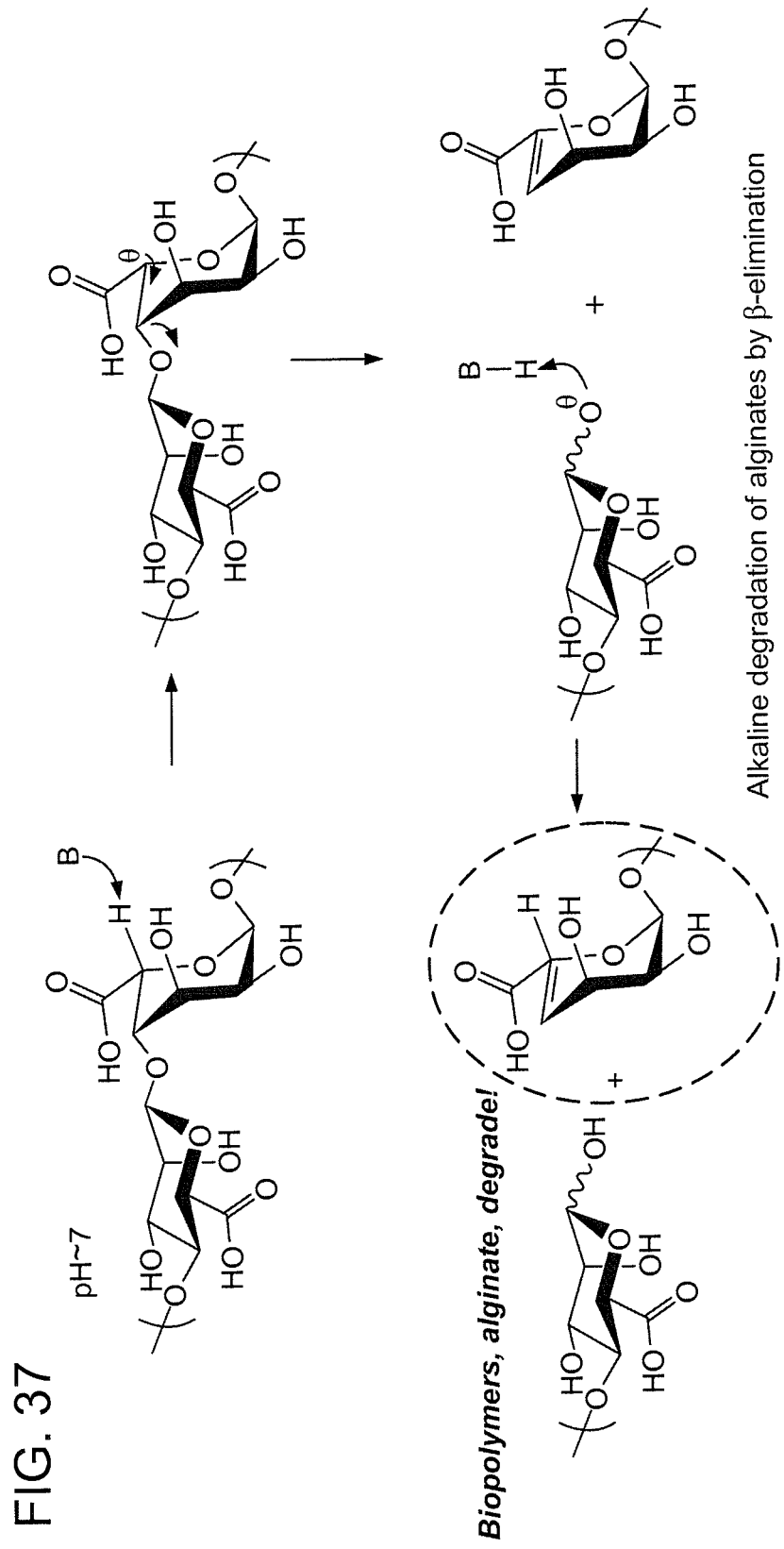
FIG. 37 is a schematic diagram showing a mechanism of chemical bond formation between two networks.
Figure 37:
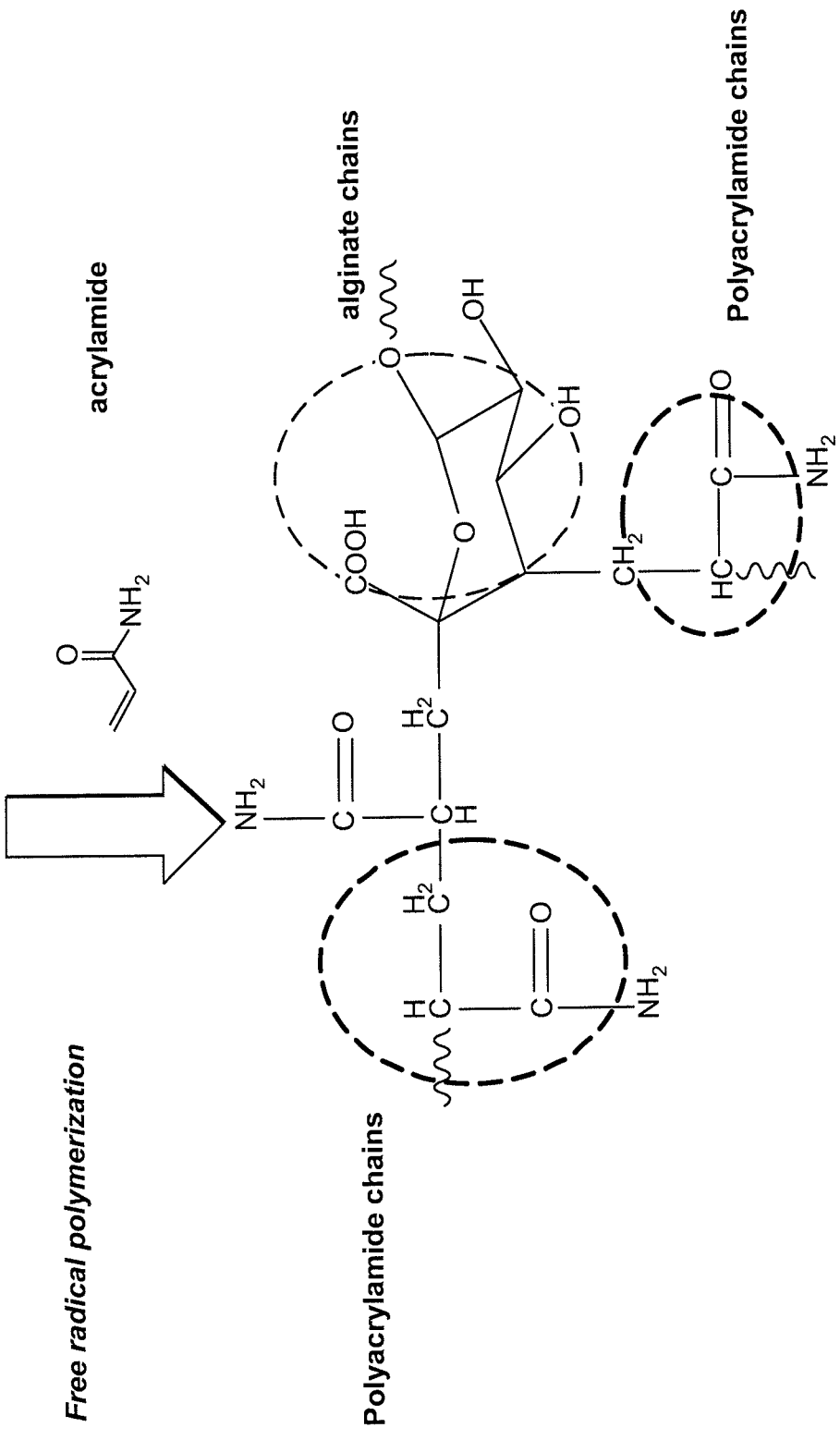

Another mechanism of covalent bond formation between two networks involves alginate degradation. At pH ~6.6, some alginate chains degrade by beta-elimination, producing shorter chains and unsaturated uronic units, which might have resonance forms and has been well-presented in literature (Tsujino I and Saito T, 1961 Nature, (9)192:970-1; Haug A and Smidsrød 0, 1965 Acta Chemica Scandinavica, 19: 341-351; Leo et al., 1990 Biotechnol Prog, 6 (1): 51-53, each of which is incorporated herein by reference). Under UV, unsaturated uronic units can react with acrylamide by free radical polymerization, thus forming chemical bonds between two networks (FIG. 37).

As described above, thermal treatment promotes covalent bond formation between the acrylamide network and the alginate network.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. An interpenetrating networks hydrogel comprising a first network and a second network, wherein:
    the first network comprises a covalently crosslinked polymer selected from the group consisting of polyacrylamide, poly(vinyl alcohol), poly(ethylene oxide) and its copolymers, polyethylene glycol (PEG), methacrylated PEG, and polyphosphazene; and
    the second network comprises an ionically crosslinked polymer selected from the group consisting of alginate, chitosan, and agarose; wherein the first network and the second network are covalently coupled;
    wherein the hydrogel has a Young's modulus value of at least 300 kPa.

2. The hydrogel of claim 1, wherein the first network comprises polyacrylamide or polyethylene glycol (PEG) and wherein the second network comprises alginate.

3. The hydrogel of claim 1, wherein the first network comprises a covalent crosslinking agent is selected from the group consisting of N,N-methylenebisacrylamide (MBAA), a methacrylate crosslinker, N,N'-dicyclohexylcarbodiimide (DCC), 1-ethyl-3-(3-dimethylaminopropyl)carbodiimide (ECC), N-hydroxysuccinimide, N-hydroxysulfosuccinimide, glutaraldehyde, and a transglutaminase.

4. The hydrogel of claim 1, wherein the hydrogel has a fracture toughness value of at least 10 J/m².

5. The hydrogel of claim 1, wherein the hydrogel has a stretch value (λ) of from 2 to 25.

6. The hydrogel of claim 1, wherein the second network comprises an ionic crosslinking agent is selected from the group consisting of $CaCl_2$, $CaSO_4$, $CaCO_3$, hyaluronic acid, and polylysine.

7. An interpenetrating networks hydrogel comprising a first network and a second network, wherein:
    the first network comprises a covalently crosslinked polymer selected from the group consisting of polyacrylamide, poly(vinyl alcohol), poly(ethylene oxide) and its copolymers, polyethylene glycol (PEG), methacrylated PEG, and polyphosphazene; and
    the second network comprises an ionically crosslinked polymer selected from the group consisting of alginate, chitosan, and agarose; and
    the hydrogel has a covalently crosslinked polymer/(covalently crosslinked polymer and ionically crosslinked polymer) ratio of between about 66.67 wt. % and 94.12 wt. % based on monomer weights, wherein the first network and the second network are covalently coupled.

8. The hydrogel of claim 7, wherein the first network comprises polyacrylamide or polyethylene glycol (PEG) and wherein the second network comprises alginate.

9. The hydrogel of claim 7, wherein the first network comprises a covalent crosslinking agent selected from the group consisting of N,N-methylenebisacrylamide (MBAA), a methacrylate crosslinker, N,N'-dicyclohexylcarbodiimide (DCC), 1-ethyl-3-(3-dimethylaminopropyl)carbodiimide (ECC), N-hydroxysuccinimide, N-hydroxysulfosuccinimide, glutaraldehyde, and a transglutaminase.

10. The hydrogel of claim 7, wherein the second network comprises an ionic crosslinking agent selected from the group consisting of $CaCl_2$, $CaSO_4$, $CaCO_3$, hyaluronic acid, and polylysine.

11. The hydrogel of claim 7, wherein the first network comprises a covalent crosslinking agent that is N,N-methylenebisacrylamide (MBAA) and the second network comprises an ionic crosslinking agent that is $CaSO_4$.

12. The hydrogel of claim 7, wherein the hydrogel has a covalently crosslinked polymer/(covalently crosslinked polymer and ionically crosslinked polymer) ratio of between about 80 wt. % and 92.31 wt. % based on monomer weights.

* * * * *

UNITED STATES PATENT AND TRADEMARK OFFICE
CERTIFICATE OF CORRECTION

PATENT NO. : 11,033,658 B2
APPLICATION NO. : 16/459907
DATED : June 15, 2021
INVENTOR(S) : Jeong-Yun Sun et al.

Page 1 of 1

It is certified that error appears in the above-identified patent and that said Letters Patent is hereby corrected as shown below:

In the Claims

In Claim 6, Column 35, Line number 30, please delete the term "is".

In Claim 7, Column 36, Line number 12, please replace the term "coupled." with the phrase
-- coupled, wherein the hydrogel has a Young's modulus value of at least 300 kPa. --.

Signed and Sealed this
Tenth Day of August, 2021

Drew Hirshfeld
*Performing the Functions and Duties of the
Under Secretary of Commerce for Intellectual Property and
Director of the United States Patent and Trademark Office*